United States Patent
Peedikakkal et al.

(10) Patent No.: US 11,850,580 B2
(45) Date of Patent: Dec. 26, 2023

(54) METHOD FOR STEREOSPECIFIC CYCLOADDITION REACTION

(71) Applicant: KING FAHD UNIVERSITY OF PETROLEUM AND MINERALS, Dhahran (SA)

(72) Inventors: Abdul Malik Peedikakkal, Dhahran (SA); Hasan Ali Al-Mohsin, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 17/822,447

(22) Filed: Aug. 26, 2022

(65) Prior Publication Data
US 2023/0041360 A1 Feb. 9, 2023

Related U.S. Application Data

(62) Division of application No. 16/596,071, filed on Oct. 8, 2019, now Pat. No. 11,471,866.
(Continued)

(51) Int. Cl.
*C07C 2/58* (2006.01)
*B01J 31/16* (2006.01)
(Continued)

(52) U.S. Cl.
CPC ......... *B01J 31/1616* (2013.01); *B01J 35/004* (2013.01); *B01J 37/031* (2013.01);
(Continued)

(58) Field of Classification Search
None
See application file for complete search history.

(56) References Cited

U.S. PATENT DOCUMENTS 9,782,745 B2 10/2017 Shimizu et al.
9,815,222 B2 11/2017 James et al.

FOREIGN PATENT DOCUMENTS

CN 102516274 B 10/2015
JP 5167122 B2 3/2013
(Continued)

OTHER PUBLICATIONS

Hasan Al-Mohsin, "Synthesis and Solid-State Photochemical [2+2] Cycloaddition Reaction of MOFs Containing 4,4'-bipyridylethylene", Thesis (Masters), College of Sciences, Chemistry Department http://eprints.kfupm.edu.sa/140731/, May 20, 2018, 1 pages (with English Abstact).
(Continued)

*Primary Examiner* — Yun Qian
(74) *Attorney, Agent, or Firm* — Oblon, McClelland, Maier & Neustadt, L.L.P.

(57) ABSTRACT

Metal-organic frameworks (MOFs) may have Zn(II), Pb(II), and/or Cd(II) as a central metal ion, a 4,4'-bipyridylethylene (bpe) ligand as a first ligand; and fumaric acid (fum) and/or oxalic acid (ox) as a second ligand, wherein the 4,4'-bipyridylethylene ligands are stacked in the MOF, and wherein a distance between two consecutive 4,4'-bipyridylethylene ligands is less than 5 Å. Cycloadditions, particularly photoinduced [2+2] cycloadditions may be catalyzed by such MOFs, and/or the conversion of photoinduced [2+2] cycloadditions in inventive MOFs may be increased by mechanical force, such as by grinding.

12 Claims, 38 Drawing Sheets

Related U.S. Application Data

(60) Provisional application No. 62/810,087, filed on Feb. 25, 2019.

(51) Int. Cl.
  *B01J 35/00*   (2006.01)
  *B01J 37/03*   (2006.01)

(52) U.S. Cl.
  CPC ............ *C07C 2/58* (2013.01); *B01J 2231/324* (2013.01); *B01J 2531/26* (2013.01); *B01J 2531/27* (2013.01); *B01J 2531/44* (2013.01); *C07C 2531/22* (2013.01)

(56) References Cited

FOREIGN PATENT DOCUMENTS

| KR | 10-2014-0098948 A | 8/2014 |
|---|---|---|
| KR | 10-2015-0007484 A | 1/2015 |

OTHER PUBLICATIONS

Lisa Batzdorf, et al., "Mechanochemical Synthesis of [Zn-3(C2O4)(3)(4,4'-bipy)(4)] and its Reorganization at High Temperatures", Zeitschrift Für Physikalische Chemie, vol. 228, No. 4-5, Jan. 2014, pp. 575-585 (Abstract only).

Xue Gao, et al., "Structure, Characterization and Photocatalytic Activity of a Series of Well-Established Covalent Heterojunction Coordination Polymers", Journal of Inorganic and Organometallic Polymers and Materials, vol. 25, Issue 5, Sep. 2015, pp. 1088-1102 (Abstract only).

Urko García-Couceiro, et al., "Rational Design of 2D Magnetic Metal-Organic Coordination Polymers Assembled from Oxalato and Dipyridyl Spacers", Crystal Growth & Design, vol. 6, No. 8, 2006, pp. 1839-1847.

"Advances in Solid-State Transformations of Coordination Bonds: From the Ball Mill to the Aging Chambers", Department of Chemistry, McGill University, htttsp://www.mdpi.com/1420-3049/22/1/144/htm, Jan. 17, 2017, 112 pages.

Garcia-Couceiro et al. Crystal Growth & Design, 6(8), 1839-1847 (Year: 2006).

US 11,850,580 B2

METHOD FOR STEREOSPECIFIC CYCLOADDITION REACTION

CROSS-REFERENCE TO RELATED APPLICATIONS

The present application is a Divisional of U.S. Application No. 16/596,071, now allowed, having a filing date of Oct, 8, 2019 and claims benefit of priority of U.S. Provisional Application No. 62/810,087 having a filing date of Feb. 25, 2019 which is incorporated herein by reference in its entirety.

STATEMENT REGARDING PRIOR DISCLOSURES BY THE INVENTOR(S)

Aspects of the application are described in the master's thesis of inventor, Hasan Ali Al-Mohsin, at King Fahd University of Petroleum and Minerals entitled "Synthesis and Solid-State Photochemical [2+2] Cycloaddition Reaction of MOFs Containing 4,4'-bipyridylethylene" (Al-Mohsin Thesis), submitted on April of 2018, an abstract of which was published on May 20, 2018. The Al-Mohsin Thesis is incorporated by reference herein in its entirety.

BACKGROUND OF THE INVENTION

Field of the Invention

The present disclosure relates to metal-organic frameworks (MOFs), particularly MOFs including a metal ion comprising Zn(II), Pb(II), and/or Cd(II) and 4,4'-bipyridylethylene (bpe), fumaric acid, and/or oxalic acid ligands, as well as photocatalysts comprising such MOFs and methods of making and using the MOFs.

Description of the Related Art

Metal-organic frameworks (MOFs) are a class of hybrid materials generally having a uniform and "infinite" structural network. MOFs are gaining interest amongst chemists and researchers due to their interesting properties and potential applications.

MOFs are well defined crystalline materials that include metal ions or metal ion clusters (known as nodes) bridged by organic ligands (known as linkers or spacers). The broad variety of MOF building blocks, metal ions/clusters and organic linkers, provides vast possibilities for chemical and topological structures, allowing for fine tuning of MOF properties. The structural topology of MOFs can be modified by the selection of metal ions and linkers. A linear linker, for instance, and octahedral nodes will produce a primitive cubic unit (PCU) topology. More than 20,000 MOFs have been reported in the literature and many topologies have been reported and studied in variety of applications. Linkers are critical part of MOFs design and can have linear, angular, trigonal, tetrahedral, and other types of geometries. The combination of certain type of geometries can produce a predicted geometry suitable for a specific application.

The ability to tailor MOF properties lends MOFs to numerous potential applications in both research and industry, e.g., as sensors and or catalysts. However, the performance and/or functionality of MOFs in each application is affected by the chemical structure of the organic linkers. Methods have been developed to alter MOF structures via organic linkers. The structure of the MOFs is generally modified by replacing the organic linkers at the start of the synthesis. However, linkers can be modified after the synthesis of MOFs by post-synthesis modification (PSM).

Post-synthesis modification (PSM) can allow the incorporation of organic linkers or other moieties into MOFs without affecting the topological structure. Such PSM-introduced moieties may even be otherwise incompatible with conventional solvothermal synthesis of the MOF, or may complicate or prevent the formation of the MOF. Some organic linkers are difficult to synthesize but may be easily formed within the MOF structure by PSM, such as cyclobutane derivatives. Recently developed methods of PSM reported include covalent PSM, dative PSM, and inorganic PSM.

Covalent PSM is the most studied method among PSM, involving modifying a covalent bond of linker ligands. Covalent PSM can be carried out by exposing an MOF to a reagent via thermal, photochemical, or electrochemical treatment. Solid-state photochemical [2+2] cycloaddition can be considered a type of covalent PSM and allows access to cyclobutane derivatives. Solid-state photochemical [2+2] cycloadditions can also be used to the modify the properties of photoreactive MOFs.

Aligning C=C olefinic bonds in a photoreactive MOF may present an attractive route to cyclic organic linkers and to modify MOF properties in the solid-state. Photochemical [2+2] cycloaddition in MOFs may be used to synthesize stereospecific cyclobutane ligands that are otherwise difficult to synthesize in solution. Photochemical [2+2] cycloaddition may also be exploited for pore modification, for photo-switching properties, and for enhancing adsorption of guest molecules.

Photo-switching has been employed to gain access to pore volume, as well as to lock guest molecules. Enhanced adsorption of guest molecules can free inaccessible internal volume, e.g., by isomerizing an azobenzene occupying the pore space from trans to cis configuration.

MOFs can be constructed in one step by self-assembly. Photochemical [2+2]cycloadditions within MOFs via post-synthesis modification (PSM) may then allow modification of MOFs for tuning properties, as well as increasing the dimensionality of MOFs, e.g., converting a one-dimensional coordination polymer to a two-dimensional polymer, then to a three-dimensional MOF, which may allow full synthetic control on MOF structures.

Although photochemical [2+2] cycloadditions in the solid-state are known, it has still been a challenge to stack a pair of C=C bonds in the crystal lattice by design. Certain efforts from the art towards solving known problems warrant comment.

U.S. Pat. No. 9,815,222 to James et al. (James) discloses a process for preparing a metal-organic compound or MOF comprising metal ion(s) and organic ligand(s), wherein the organic ligand can associate with the metal ion. James's method mixes a metal in ionic form and an organic ligand capable of associating with the metal in ionic form, under conditions of prolonged and sustained pressure and shear sufficient to synthesize a metal-organic compound. James does not specify any particular metal or ligand, but indicates that suitable metal ions include $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^{+}$, $Ir^{2+}$, $Ir^{+}$, $Ni^{2+}$, $Ni^{+}$, $Pd^{2+}$, $Pd^{+}$, $Pt^{2+}$, $Pt^{+}$, $Cu^{2+}$, $Cu^{+}$, $Ag^{+}$, $Au^{+}$, $Zn^{2+}$, $Cd^{2+}$, $Hg^{2+}$, $Al^{3+}$, $Ga^{3+}$, $In^{3+}$, $Tl^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^{+}$, $Sb^{5+}$, $Sb^{3+}$, $Sb^{+}$, $Bi^{5+}$, $B^{3+}$, and $Bi^{+}$, especially preferring $Cu^{2+}$, $Cu^{+}$, and $Zn^{2+}$. James mentions bidentate chelates including a large list of dicarboxylic acids and 2,2'-bipyridine, but does not mention 4,4'-bipyridylethylene or similar bidentate (hetero)aromatics bridged by an olefinic bond, nor particularly Pb chelates.

CN 102516274 B by Huang et al. (Huang) discloses catalytic MOF cadmium compounds, their preparation and use. Huang uses hot ionic liquid to synthesize central bridging trinuclear cadmium ion clusters with a carboxylic acid ligand in an MOFs. Huang's MOFs compounds may catalyze the oxidation of cyclohexene, with a selectivity of peroxide reaching ~96%. Huang's MOFs contain neither Pb nor Zn, nor 4,4'-bipyridylethylene, instead requiring $Cd_3F$ or $Cd_3F_2$ frameworks.

KR 10-2014-098948 A by Kim et al. (Kim I) discloses a crystal structure, fluorescence and transesterification catalysis characteristics of coordination polymers of zinc, malonate, and bipyridyl ligands. Kim I's coordination polymers can be used as a fluorescent material and in electronic displays, and catalyze transesterification and be reused at mild conditions. While Kim I discloses a zinc-organic frame works comprising 4,4'-bipyridylethylene, including [(Zn $(H_2O)(\mu$-malonate$)\}_2(\mu$-bpe$)](H_2O)(CH_3CN)$, Kim I does not disclose $\{(Hbpe)_2[Zn_2(ox)_3]\}_n.(H_2O).2.2(DMF)$, nor Pb-based MOFs, nor [2+2]cycloadditions.

DE 10 2005 023 856 A1 by Hesse et al. (Hesse), also published as JP 5167122 B2, discloses porous metal-organic frameworks of at least two organic compounds coordinated to a metal ion, their electrochemical production and use, esp. for gas storage and separation. Hesse discloses suitable metals as being from Groups Ia, IIa, IIIa, IVa to VIIIa, Ib, and VIb of the periodic table, especially Cu, Ni, Fe, Co, Zn, Mn, Ru, Mo, Cr, W, Rh, and Pd, and anions such as $Cu^{2+}$, $Cu^+$, $Ni^{2+}$, $Ni^+$, $Fe^{3+}$, $Fe^{2+}$, $Co^{3+}$, $Co^{2+}$, $Zn^{2+}$, $Mn^{3+}$, $Mn^{2+}$, $Ru^{3+}$, $Ru^{2+}$, $Mo^{3+}$, $Cr^{3+}$, $W^{3+}$, $Rh^{2+}$, $Rh^+$, $Pd^{2+}$, and Pd+ in Hesse's anode/cathode system. Hesse describes di, tri, and tetracarboxylic acids as ligands, but also (hetero)aromatics, including bipyridyl, but does not describe 4,4'-bipyridylethylene, nor its combination with oxalic or malonic acid.

KR 10-2015-0007484 A by Kim et al. (Kim II) discloses a zinc-metal organic framework (Zn-MOF) with a two-dimensional (2D) structure of $[Zn(glu)(\mu$-bpe$).2(H_2O)]_n$ connected by glutaric acid and bipyridine ligands. Kim II's Zn-MOF can be used as a selective carbon dioxide adsorbent or a heterogeneous transesterification catalyst. Kim II does not use both a bpe and an oxalate or malonate ligand, nor does Kim II use Pb, or describe [2+2] cycloadditions.

U.S. Pat. No. 9,782,745 to Shimizu et al. (Shimizu) discloses a metal-organic framework (MOF) materials useful for adsorbing $CO_2$, having pores and comprising zinc ions, oxalate, and a cycloazocarbyl compound, such as imidazolates, triazolates, and tetrazolates, preferably 1,2,4-triazolate. Shimizu describes 1H-1,2,4-triazolate-1-carboxamidine, 3-amino-1,2,4-triazolate, imidazolate, 4-fluoroimidazolate, 2-methyl-imidazolate, and 1,2,3,4-tetrazolate, but Shimizu fails to describe 4,4'-bipyridylethylene, or lead, or [2+2] cycloadditions.

*Molecules* 2017, 22(1), 144 by Mottillo et al. (Mottillo) discloses a review of forming coordination bonds in functional metal-organic materials, such as coordination polymers and metal-organic frameworks (MOFs) to metallodrugs. Mottillo describes making coordination bonds via solid-state coordination chemistry for quantitative yields, enhanced stoichiometric and topological selectivity, access to a wider range of precursors, and to molecules and materials not readily accessible in solution or solvothermally. Mottillo discloses 1D coordination polymers, including $Zn(fum).4H_2O$ and $Zn(fum).5H_2O$, and pillared MOFs from milling ZnO, fumaric acid, and 4,4'-bipyridine or bpe. Mottillo does not disclose $\{(Hbpe)_2[Zn_2(ox)_3]\}_n.(H_2O).2.2$ (DMF), $[Pb_4(ox)_3(bpe)_4(H_2O)_4]_n.(NO_3)_2$, or $[Pb(bpe)(fum)]_n.0.25(H_2O)$.

*Zeitschr. Phys. Chem.* 2014, 228(4-5), 575-585 by Troebs et al. (Troebs) discloses synthesizing a metal organic layered structure catena-(bis($\mu_2$-4,4'-bipyridine)-tris($\mu_2$-oxalato)-bis (4,4'-bipyridine)-tri-zinc(ii)), i.e., $[Zn_3(ox)_3(4,4'$-bipy$)_4]$, mechanochemically by three different routes. Troebs describes synthesizing $[Zn_3(ox)_3(4,4'$-bipy$)_4]$ by: i) simultaneously neat grinding of $Zn(OAc)_2.2(H_2O)$, oxalic acid dihydrate, and 4,4'bipyridine, and ii) grinding two compounds and adding the third afterwards, independent of the sequence. Troebs describes that the monoclinic structure of $[Zn_3(ox)_3(4,4'$-bipy$)_4]$ rearranges reversibly to a higher ordered orthorhombic structure, $[Zn(ox)(4,4'$-bipy$)]$, at high temperatures. Troebs does not disclose 4,4'-bipyridylethylene, nor MOFs using Pb, nor $\{(Hbpe)_2[Zn_2(ox)_3]\}_n.(H_2O).2.2(DMF)$, $[Pb_4(ox)_3(bpe)_4(H_2O)_4]n.(NO_3)_2$, or [Pb (bpe)fum)$]_n.0.25(H_2O)$.

*J. Inorg. Organometal. Polym. Mater.* 2015, 25(5), 1088-1102 by Gao et al. (Gao) discloses coordination polymers $\{Co(HCOO)_2(4,4'$-bipy$))\}_n$, $\{[Ni(4,4'$-bipy$)(OH)_2(H_2O)_2]$. $suc.2H_2O\}_n$, $\{(Ni(HCOO)_2(4,4'$-bipy$))\}_n$, $\{Zn(HCOO)_2(4, 4'$-bipy$)\}_n$, $\{Cu(HCOO)_2(4,4'$-bipy$)\}_n$, and $\{[Cu(ox)(2,2'$-bipy$)].2H_2O\}_n$, suc meaning succinic acid, based on pyridine derivatives and carboxylates as ligands, and their photocatalytic and heterojunction activity. Gao discloses no Pb-containing MOFs, nor 4,4'-bipyridylethylene or olefin-linked aromatic bidentate ligands.

*Crystal Growth & Des.* 2006, 6(8), 1839-1847 by Garcia-Couceiro et al. (Garcia) discloses using 1,2-bis(4-pyridyl) ethane (bpa) and 1,2-bis(4-pyridyl)ethylene (bpe) as spacers to design of 2D compounds of molecular formulas $[M(\mu$-ox$)(\mu$-bpa$)]_n$ (M(II)=Zn (1), Ni (2), Mn (3), Fe (4), or Cu (5)) and $[M(\mu$-ox$)(\mu$-bpe$)]_n$ (M(II)=Zn (6), Ni (7), Co (8), Fe (9), or Cu (10)). Garcia's compounds were synthesized by diffusion and hydrothermally, yielding hexa-coordinated metal atoms to four oxygen atoms of two bridging oxalates and two nitrogen atoms of two bidentate dipyridyl molecules to afford 2D rectangular grid-type networks of infinite $[M(\mu$-ox$)]n$ chains cross-linked by organic spacers. Garcia may disclose $[Zn(II)(\mu$-ox$)(\mu$-bpe$)]_n$, $[Ni(II)(\mu$-ox$)(\mu$-bpe$)]_n$, $[Co(II)(\mu$-ox$)(\mu$-bpe$)]_n$, $[Fe(II)(\mu$-ox$)(\mu$-bpe$)]_n$, and $[Cu(II) (\mu$-ox$)(\mu$-bpe$)]_n$ MOFs. However, the alignment of ligands in Garcia's MOFs is criss-crossed and the distance between their C=C olefinic bonds is more than 5.377 Å, which renders these MOFs photochemically inactive.

Of the several known structures of bpe-ox Mn-based MOFs, all but one, $[Mn_2(\mu$-ox$)_2(\mu$-bpe$)(bpe)_2]_n$ reported in *Inorg. Chem.* 2010, 49(24), 11346-11361 (Garcia II), are photochemically inactive, possibly because ligand alignment is out of phase and/or the distance between the olefinic bonds is excessive. $[Mn_2(\mu$-ox$)_2(\mu$-bpe$)(bpe)_2]_n$ has a broken ladder-like 2D sheet structure with an infinite alignment of C=C olefinic bonds within a 4.2 Å distance. However, $[Mn_2(\mu$-ox$)_2(\mu$-bpe$)(bpe)_2]_n$ includes a paramagnetic metal ion, and Garcia II does not describe Zn(II) or Pb(II)-based MOFs. Only two known bpe-fum based MOFs, $[Cd_2(bpe)_2(fum)_2]$ and $[Zn(bpe)(fum)].0.25H_2O$, have been reported to be photochemically reactive, for example, based on the alignment of olefinic C=C bonds of bpe within the right structural conditions, though no MOFs with bpe-fum linkers and a lead (Pb) metal ion have been reported.

In light of the above, a need remains for photocatalysts and/or sensors comprising new MOFs, particularly based on Pb and/or Zn using oxalates and/or fumarates and 4,4'- bipyridylethylene, methods of conducting and/or enhancing photocatalysis, particularly [2+2]cycloadditions, and methods of making such MOFs.

SUMMARY OF THE INVENTION

Aspects of the invention provide metal-organic frameworks (MOFs), comprising: Zn(II), Pb(II), and/or Cd(II) as a metal ion; a 4,4'-bipyridylethylene (bpe) ligand as a first ligand; and fumaric acid (fum) and/or oxalic acid (ox) as a second ligand, wherein the 4,4'-bipyridylethylene are stacked in the MOF, and wherein a distance between two consecutive 4,4'-bipyridylethylene is less than 5 Angstroms. MOFs within the scope of the invention may be modified with any permutation of the features described herein, particularly the following.

The metal ion may preferably comprise Pb(I), or a first and a second Zn(II), or a first, second, third, and fourth Pb(II). The second ligand may comprise a first, second, and third oxalic acid. The first ligand may be protonated.

The first and second ligand and the metal ion may be $\{(Hbpe)_2[Zn_2(ox)_3]\}_n$ and/or the MOF may have the formula $\{(Hbpe)_2[Zn_2(ox)_3]\}_n \cdot (H_2O) \cdot 2.2(DMF)$ (1).

The first and second ligand and the metal ion may be $[Pb_4(ox)_3(bpe)_4(H_2O)_4]_n$ and/or the MOF may have the formula $[Pb_4(ox)_3(bpe)_4(H_2O)_4]_n \cdot (NO_3)_2$ (2).

The first and second ligand and the metal ion may be $[Pb(bpe)(fum)]_n$ and/or the MOF may have the formula $[Pb(bpe)(fum)]_n \cdot 0.25(H_2O)$ (3).

Aspects of the invention include photocatalysts comprising any permutation of the inventive MOF(s) described herein. The photocatalyst(s) may preferably be suitable to catalyze a [2+2] cycloaddition to form a cyclobutane.

Aspects of the invention comprise sensors comprising any permutation of the inventive MOF(s) described herein.

Aspects of the invention provide methods of increasing the conversion of a [2+2]cycloaddition, the method comprising: grinding any permutation of the inventive MOF(s) described herein, preferably containing Cd and/or have the formula $[Cd(bpe)_{1.5}(NO_3)_2(H_2O)]_n$, to obtain a ground MOF; and irradiating the ground MOF with UV light.

Aspects of the invention include methods of synthesizing any permutation of the inventive MOF(s) described herein, which methods may comprise: dissolving the metal salt and/or the 4,4'-bipyridylethylene (bpe) to form solution A; dissolving the second ligand in a solvent to form solution B; and mixing the solution A and the solution B to form the MOF, wherein a molar ratio of the metal ion to the first ligand to the second ligand is in a range of from 1:2.5 to 3.5:1.25 to 1.75. The MOF may preferably be isolated as a precipitate.

Aspects of the invention comprise methods of synthesizing a four-membered carbon cycle, the method comprising: irradiating any permutation of the inventive MOF(s) described herein with UV light to form the four-membered carbon cycle.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
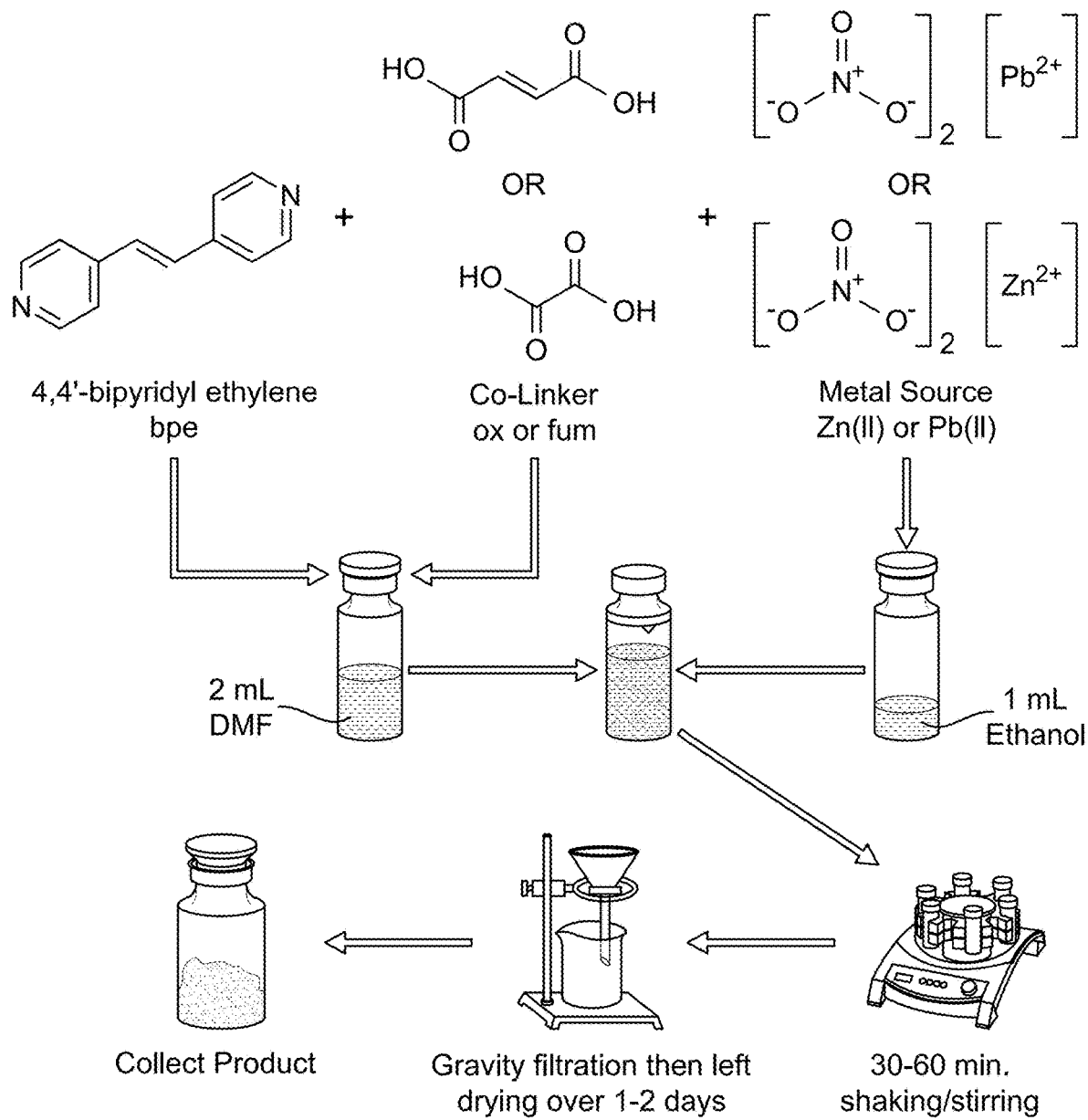
FIG. 1 shows a pictorial representation of the syntheses of the three exemplary MOFs, compound (1), i.e., $\{(Hbpe)_2$ $[Zn_2(ox)_3]\}_n \cdot (H_2O) \cdot 2.2(DMF)$, compound (2), i.e., $[Pb_4(ox)_3(bpe)_4(H_2O)_4]_n \cdot (NO_3)_2$, and compound (3), i.e., $[Pb(bpe)(fum)]_n \cdot 0.25(H_2O)$.

Aspects of the invention provide metal-organic frameworks (MOFs), which may comprise: 1, 2, 3, 4, 5, or more Zn(II), Pb(II), and/or Cd(II) as a metal ion, or may consist (essentially) of these metals, i.e., containing no amount of further metal distorting the crystal lattice such that the aligned olefinic bonds are beyond 5 Å and/or cannot be mechanically forced (e.g., by grinding) back within 5 Å; a 4,4'-bipyridylethylene (bpe) ligand as a first ligand; and fumaric acid (fum) and/or oxalic acid (ox) as a second ligand, wherein the 4,4'-bipyridylethylene ligands are stacked in the MOF, and wherein a distance between two consecutive 4,4'-bipyridylethylene (or analog) ligands is less than or no more than 5, 4.95, 4.9, 4.85, 4.8, 4.75, 4.7, 4.65, 4.6, 4.55, 4.5, 4.45, 4.4, 4.35, 4.3, 4.25, 4.2, 4.15, 4.1, 4.05, or 4 Å (or less) and/or at least 1.5, 1.75, 2, 2.25, 2.5, 2.75, 3, 3.1, 3.2, 3.3, 3.4, or 3.5 Å, particularly at the olefin. The first and second ligands may be substituted, as described below, whereby the bipyridylethylene ligand should generally maintain its [2+2]cycloaddition activity and the substituents do not distort the crystal lattice such that the aligned olefinic bonds are beyond 5 Å and/or cannot be mechanically forced (e.g., by grinding) back within 5 Å. For example, the 4,4'-bipyridylethylene ligand may be independently substituted at the 2, 3, 5, or 6 position on one or both of the pyridyl rings, and/or mono or disubstituted (nongeminally) across the olefinic bond. The fumaric acid (or maleic acid, if cis-isomerized) may likewise be mono or disubstituted, across the C=C bond. Unsubstituted analogs may be preferred if for nothing more than lower cost.

The metal ion may preferably comprise or consist (essentially) of Pb(II), optionally only one Pb(II), or a first and a second Zn(II), i.e., at least two Zn(II) atoms in its repeating structure, or a first, second, third, and fourth Pb(II), i.e., at least three or four Pb(II) in its repeating structure. Inventive MOFs may preferably combine bpe, oxalic acid, and Pb(II), but no further non-solvating coordinating components. Inventive MOFs may preferably combine bpe, fumaric (or maleic) acid, and Pb(II), but no further non-solvating coordinating components. Inventive MOFs may preferably combine bpe, oxalic acid, and Zn(II)—or two Zn(II), but no further non-solvating coordinating components. Inventive MOFs are generally hydrates and/or nitrates, but may also coordinate (or exclude) further solvent molecules, such as DMF or any solvent(s) described below. The second ligand may comprise a first, second, and third oxalic acid, i.e., at least three oxalates/oxalic acids in its repeating structure. The first ligand, preferably an unsubstituted bpe, may be protonated, preferably monoprotonated.

The first and second ligand and the metal ion may be $\{(Hbpe)_2[Zn_2(ox)_3]\}_n$, i.e., the MOF may contain such a core as its repeat element, occupying at least 75, 80, 85, 90, 92.5, 95, 97.5, 98, 99, 99.1, 99.5, or 99.9 wt. % of the repeat unit, for example, and/or the MOF may have the formula $\{(Hbpe)_2[Zn_2(ox)_3]\}_n \cdot (H_2O) \cdot 2.2(DMF)$ (1), occupying at least 75, 80, 85, 90, 92.5, 95, 97.5, 98, 99, 99.1, 99.5, or 99.9 wt. % of the repeat unit.

The first and second ligand and the metal ion may be $[Pb_4(ox)_3(bpe)_4(H_2O)_4]_n$, i.e., the MOF may contain such a core as its repeat element, occupying at least 75, 80, 85, 90, 92.5, 95, 97.5, 98, 99, 99.1, 99.5, or 99.9 wt. % of the repeat unit, for example, and/or the MOF may have the formula $[Pb_4(ox)_3(bpe)_4(H_2O)_4]_n \cdot (NO_3)_2$ (2), occupying at least 75, 80, 85, 90, 92.5, 95, 97.5, 98, 99, 99.1, 99.5, or 99.9 wt. % of the repeat unit.

The first and second ligand and the metal ion may be $[Pb(bpe)fum)]_n$, i.e., the MOF may contain such a core as its repeat element, occupying at least 75, 80, 85, 90, 92.5, 95, 97.5, 98, 99, 99.1, 99.5, or 99.9 wt. % of the repeat unit, for example, and/or the MOF may have the formula $[Pb(bpe)fum)]_n \cdot 0.25(H_2O)$ (3), occupying at least 75, 80, 85, 90, 92.5, 95, 97.5, 98, 99, 99.1, 99.5, or 99.9 wt. % of the repeat unit.

Aspects of the invention include photocatalysts and/or sensors comprising any permutation of the inventive MOF(s) described herein. The photocatalyst(s) may preferably be suitable to catalyze a [2+2] cycloaddition to form a cyclobutane. Inventive sensors and/or photocatalysts may be responsive to UV and/or visible light, even exclusively, or to light in a range of from 10 to 1000 nm, e.g., at least 10, 25, 50, 75, 100, 125, 150, 175, 200, 225, 250, 275, 300, 325, 350, 375, 400, 425, 450, 475, or 500 nm and/or no more than 1000, 950, 900, 850, 800, 750, 700, 600, 550, 500, 450, 400, 350, 300, 250, 225, or 200 nm. The sensor may implement a reversible cycloaddition reaction and/or measure UV and/or thermal load.

Aspects of the invention provide methods of increasing the conversion of a [2+2]cycloaddition, e.g., by at least 10, 15, 20, 25, 30, 33, 35, 40, 45, 50, 55, 60, 70, 80, 90, or 100% or any range with these endpoints. Such methods may comprise grinding any permutation of the inventive MOF(s) described herein, preferably containing Cd and/or bpe and/or having the formula $[Cd(bpe)_{1.5}(NO_3)_2(H_2O)]_n$, to obtain a ground MOF; and irradiating the ground MOF with UV (or visible) light in any range described above.

Aspects of the invention include methods of synthesizing any permutation of the inventive MOF(s) described herein, which methods may comprise: dissolving the metal salt and/or the 4,4'-bipyridylethylene (bpe) to form solution A; dissolving the second ligand in a solvent to form solution B; and mixing the solution A and the solution B to form the MOF, wherein a molar ratio of the metal ion to the first ligand to the second ligand is in a range of from 1:2.5 to 3.5 (e.g., at least 2.5, 2.55, 2.6, 2.65, 2.75, 2.8, 2.85, 2.9, 2.95, or 3 and/or up to 3.5, 3.45, 3.4, 3.35, 3.3, 3.25, 3.2, 3.15, 3.1, 3.05, or 3): 1.25 to 1.75 (e.g., at least 1.25, 1.3, 1.33, 1.35, 1.4, 1.45, 1.5, or 1.55 and/or up to 1.75, 1.7, 1.67, 1.65, 1.6, 1.55, 1.5, or 1.45). The MOF may preferably be isolated as a precipitate, e.g., as a granular solid, which may be filtered. The MOF may preferably be recrystallizable, e.g., in organic solvent(s) or some combination of the solvents listed below.

Aspects of the invention comprise methods of synthesizing a four-member, e.g., C4, carbon cycle, the method comprising: irradiating any permutation of the inventive MOF(s) described herein with UV light to form the four-membered carbon cycle.

Aspects of the invention comprise photoreactive MOFs that can stack a pair of C=C olefinic bonds of 4,4'-bipyridylethylene (bpe) with less than 4.2 Å distance in crystal lattice for solid-state photochemical [2+2] cycloaddition reaction, while using fumaric acid (fum) and/or oxalic acid (ox) as co-linkers and Cd(II), Pb(II), and/or Zn(II) as metal ion nodes.

Aspects of the invention include MOFs that are suitable for use in sensors, optical switches, and/or photolithography, due to their variable metal centers and ligands, high surface area, and variable (reversible) stability. The photoreactivity of inventive MOFs may be tuned based on the photochemical [2+2] cycloaddition reaction of olefinic C=C bonds in the solid-state. Aspects of the invention provide photochemical [2+2] cycloaddition reactions in solid state, particularly for the synthesis of cyclobutane derivatives, with at least 75, 77.5, 80, 82.5, 85, 87.5, 88, 89, 90, up to 100% yield, and/or solvent-free.

Inventive MOFs may exclude $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^+$, $Ir^{2+}$, $Ir^+$, $Ni^{2+}$, $Ni^+$, $Pd^{2+}$, $Pd^+$, $Pt^{2+}$, $Pt^+$, $Cu^{2+}$, $Cu^+$, $Ag^+$, $Au^+$, $Zn^{2+}$, $Cd^{2+}$, $Hg^{2+}$, $Al^{3+}$, $Ga^{3+}$, $In^{3+}$, $Ti^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^+$, $Sb^{5+}$, $Sb^{3+}$, $Sb^+$, $Bi^{5+}$, $B^{3+}$, and/or $Bi^+$, or contain no more than UV detectable traces thereof, or may comprise no more than 15, 10, 7.5, 5, 4, 3, 2.5, 2, 1, 0.5, 0.1, 0.01, 0.001, 0.0001, or 0.00001 wt. %, relative to the total weight of metals/metalloids in the MOF, of any or all of these. Inventive MOFs may exclude certain ligands, including aromatic carboxylates (esp. aromatic diacids such as phthalates), aliphatic (di)amines such as methylamine, ethylamine, ethylenediamine, etc., amino acids, phenolics, $F^-$, $Cl^-$, $Br^-$, $I^-$, $OH^-$, $CN^-$, $CO$, $NH_3$, $SCN^-$, $N_3^-$, $CH_3CN$, $C_5H_5N$, $NO_2^-$, acetate, citrate, EDTA, and/or $S^{2-}$, or contain no more than UV detectable traces thereof, or may comprise no more than 15, 10, 7.5, 5, 4, 3, 2.5, 2, 1, 0.5, 0.1, 0.01, 0.001, 0.0001, or 0.00001 wt. %, relative to the total weight of metals/metalloids in the MOF, of any or all of these. Inventive materials may comprise no more than 40, 33, 25, 20, 15, 10, 7.5, 5, 4, 3, 2, 1, or 0.5 wt. %, relative to the total weight of metals/metalloids in the MOF, of Cu, Ni, Fe, Co, Zn, Mn, Ru, Mo, Cr, W, Rh, and/or Pd.

Inventive MOFs can be prepared without ionic liquids and it is tolerable that inventive MOFs are catalytically inactive for oxidation and/or transesterification.

Aspects of the invention provide solid-state photochemical [2+2] cycloadditions with inventive MOFs, particularly having stacked pairs of C=C bonds in their crystal lattice. Aspects of the invention synthesize optionally photoreactive MOFs that can stack a pair of C=C olefinic bonds, e.g., of 4,4'-bipyridylethylene (bpe) or analogs thereof, with less than 5.0, 4.9, 4.8, 4.7, 4.6, 4.5, 4.4, 4.3, 4.2, 4.1, 4.0, 3.9, or less Å distance in crystal lattice, generally suitable for solid-state photochemical [2+2] cycloadditions, particularly using fumaric acid (fum) and/or oxalic acid (ox) as co-linkers, below, and Cd(II), Pb(II) and/or Zn(II) as metal ion nodes. The 4,4'-bipyridylethylene (bpe) ligands may be substituted by 1, 2, 3, or 4 substituents on one or more aryl groups, for example, F, methyl, $CF_3$, ethyl, propyl, isopropyl, cyclopropyl, butyl, t-butyl, hydroxy, methoxy, ethoxy, and/or carboxylate. The substituents of the ethylene groups in bpe or fum may be 1 or 2 of any of the aforementioned groups, particularly methyl and F.

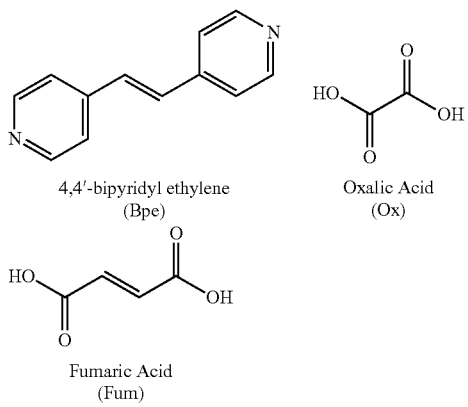

4,4'-bipyridyl ethylene
(Bpe)

Oxalic Acid
(Ox)

Fumaric Acid
(Fum)

Aspects of the invention involve tuning the photoreactivity of the MOFs, particularly with regard to photodimerization reactions, and optionally driving the yield, % conversion, and/or stereoselectivity, e.g., of cyclobutane conversion.

Inventive syntheses of (photoreactive) MOFs may be conducted via a parallel alignment of the C=C double bonds of 4,4'-bipyridylethylene (bpe), using fumaric acid (fum) and/or oxalic acid (ox) as co-linkers, and Cd(II), Zn(II), and/or Pb(II) as metal ions. The photoirradiative efficacy of inventive MOFs in crystal may be monitored by $^1$H-NMR spectroscopy. Aspects of the invention provide specific light sensitive materials and/or sensors. Aspects of the invention employ mixed systems with bpe-ox linkers as photochemical catalysts.

Aspects of the invention provide inducing, optionally aided by mechanical forces, such as grinding, MOFs, complexes, and/or organic salts containing aligned olefinic double bonds of bpe ligands to undergo photochemical [2+2] cycloaddition. Aspects of the invention comprise storing gas(es) and/or gas storage devices comprising porous MOFs, including compounds (1), (2), and/or MOF(s) of analogous lattice structure. Aspects of the invention include single crystals of compound (1), (2), and/or (3), and methods of crystallizing the same, particularly from (organic) solvents, such as pyridine, N,N-dimethylformamide (DMF), N,N-dimethylacetamide, N-methyl pyrrolidone (NMP), hexamethylphosphoramide (HMPA), dimethyl sulfoxide (DMSO), acetonitrile, tetrahydrofuran (THF), 1,4-dioxane, dichloromethane, chloroform, carbon tetrachloride, dichloroethane, acetone, ethyl acetate, pet ether, pentane, hexane(s), cyclohexane, decane(s), decalin, THF dioxane, benzene, toluene, xylene(s), o-dichlorobenzene, diethyl ether, methyl t-butyl ether, diisopropyl ether, ethylene glycol, methanol, ethanol, isopropanol, propanol, n-butanol, and/or water. Inventive materials may exhibit photoluminescence suitable, e.g., for sensors applications.

Pb(II) can maintain a high coordination number, but has been thought to risk different topological structure to be self-assembled, while fumaric acid containing MOFs are not commonly photoreactive.

Although several methods have been utilized to force partially photodimerizing systems to reach 100% conversion, such as desolvation, dehydration, and mechanical forces, as described in Chem. Comm. 2008, 42, 5277, and Chem. Eur. J. 2008, 14(17), 5329-5334, each of which is incorporated by reference herein in its entirety, no reference describing the use of forceful methods has attempted such methods on ladder-like structures. An aspect of the invention allows the unexpectedly successful use of such methods of force and/or (internal) molecular movements, generally induced mechanically, to align two ladder structures and obtain pseudo-infinite ligand (e.g., bpe) olefinic alignments.

If the two adjacent ladder structures can be aligned successfully, the MOF topology will be converted to an approximated two-dimensional sheet. The photodimerization in (photoreactive) two-dimensional sheet MOFs can result in modification of the photoreactive organic linkers and structural transformation. Structural transformation of inventive MOFs via photodimerization can convert 1D→2D or 2D→3D depending on the topological structure of the MOF.

EXAMPLES

Chemicals: Chemicals were purchased commercially and used as received unless indicated otherwise. Fumaric acid (fum), oxalic acid (ox), and 4,4'-bipyridylethylene (bpe), were used as exemplary organic linkers for photoreactive MOFs, while $Zn(NO_3)_2 \cdot 6H_2O$ and $Pb(NO_3)_2$ were used as exemplary metal sources.

Synthesis of Metal-Organic Frameworks

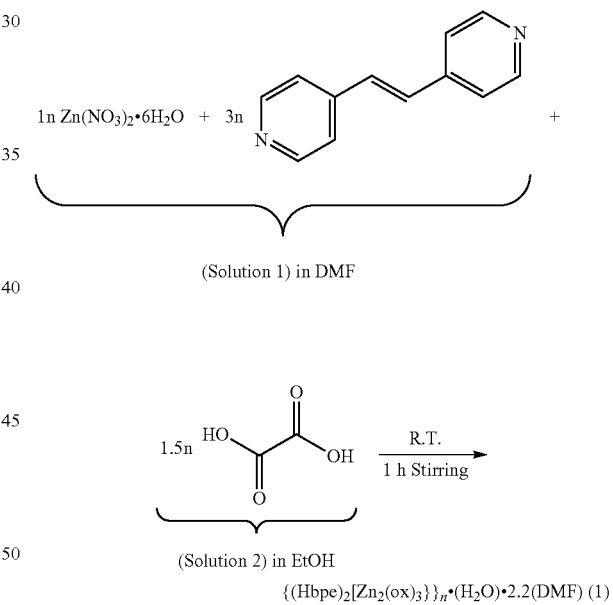

(Solution 1) in DMF (Solution 2) in EtOH

{(Hbpe)$_2$[Zn$_2$(ox)$_3$]}$_n$·(H$_2$O)·2.2(DMF) (1)

Synthesis of {(Hbpe)$_2$[Zn$_2$(ox)$_3$]}$_n$·(H$_2$O)·2.2(DMF) (1): In a 20-mL vial, 20 mg (0.067 mmol) of zinc(II) nitrate hexahydrate, $Zn(NO_3)_2 \cdot 6H_2O$, and 36 mg (0.20 mmol) of 4,4'-bipyridylethylene (bpe) were dissolved in 2 mL of dimethylformamide (DMF). In another 20-mL vial, 12 mg (0.10 mmol) of oxalic acid dihydrate (ox) were dissolved in 1 mL of ethanol. The two solutions were then mixed at room temperature and an orange-ish white fine powder rapidly formed. The vial containing the solvents and the orange-ish white fine powder was placed on a shaker for 1 hour. The powder product was gravity filtered with filter paper, washed three times with DMF and three times with ethanol, and left to dry over 24 hour, yielding 23.4 mg (90%) of MOF (1).

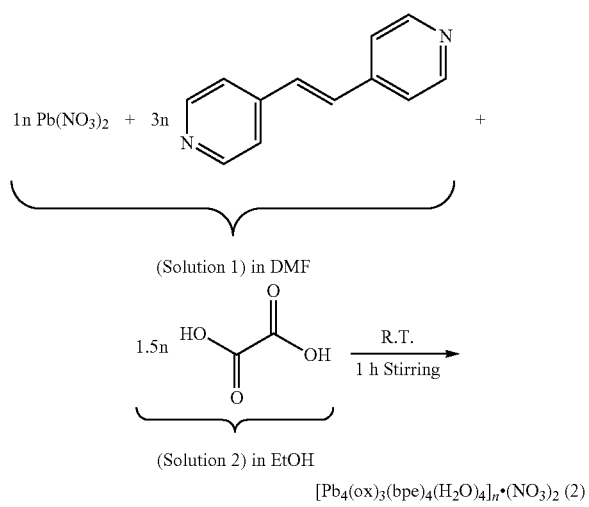

(Solution 1) in DMF (Solution 2) in EtOH

[Pb$_4$(ox)$_3$(bpe)$_4$(H$_2$O)$_4$]$_n$·(NO$_3$)$_2$ (2)

Synthesis of [Pb$_4$(ox)$_3$(bpe)$_4$(H$_2$O)$_4$]$_n$·(NO$_3$)$_2$(2): In 2 mL of DMF, 20 mg (0.060 mmol) of Pb(NO$_3$)$_2$ and 36 mg (0.20 mmol) of 4,4'-bipyridylethylene (bpe) were dissolved. The solution was mixed at room temperature with another solution of 12 mg (0.10 mmol) of oxalic acid (ox) dissolved in 1 mL of ethanol. A pinkish white fine powder rapidly formed. The mixture containing the solvents and the pinkish white fine powder was placed on a shaker for 1 hour. The powder product was filtered, washed three times with DMF and three times with ethanol, then left to dry over 24 hours. The yield was 25.8 mg (85%) of MOF (2).

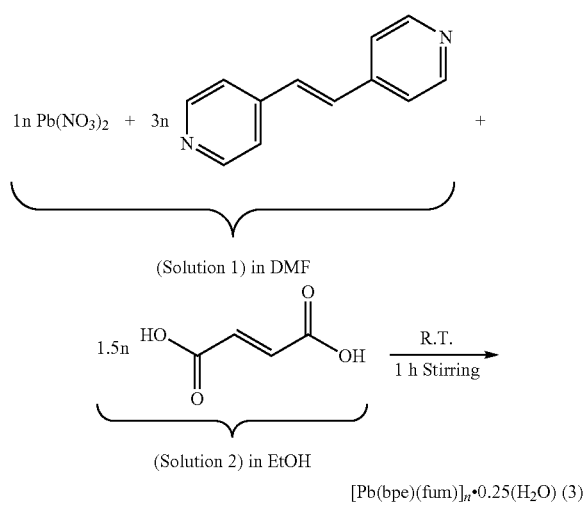

(Solution 1) in DMF (Solution 2) in EtOH

[Pb(bpe)(fum)]$_n$·0.25(H$_2$O) (3)

Synthesis of [Pb(bpe)(fum)]$_n$·0.25(H$_2$O) (3): In a small vial, a 20 mg (0.060 mmol) of Pb(NO$_3$)$_2$ and 36 mg (0.20 mmol) of 4,4'-bipyridylethylene (bpe) were dissolved in 2 mL of dimethylformamide (DMF). In another small vial, a solution of 12 mg (0.10 mmol) of fumaric acid (fum) was dissolved in 1 mL of ethanol. The two solutions were mixed at room temperature and a pale pink powder rapidly formed. The mixture containing the solvents and the pale pink powder was stirred for 1 hour. The product was then slowly filtered, washed three times with DMF and three times with ethanol, and then left to dry over 24 hour. The yield of the reaction was 20.9 mg (72%) of MOF (3).

The syntheses of the three exemplary MOFs is pictorially summarized in FIG. 1.

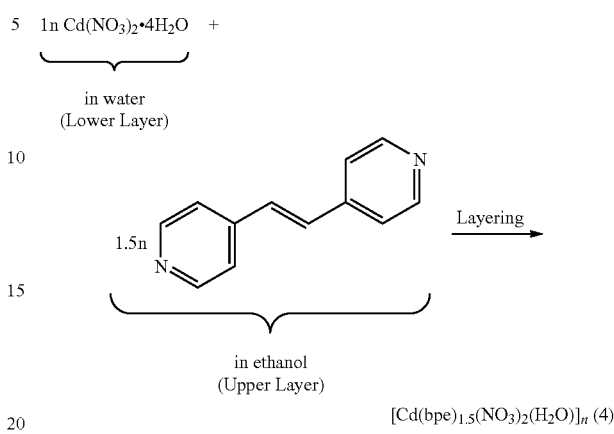

in water (Lower Layer)

in ethanol (Upper Layer)

[Cd(bpe)$_{1.5}$(NO$_3$)$_2$(H$_2$O)]$_n$ (4)

Synthesis of [Cd(bpe)$_{1.5}$(NO$_3$)$_2$(H$_2$O)]$_n$ (4): The cadmium MOF was synthesized by a layering technique based on the procedure reported in *Inorg. Chem.* 1999, 38(13), 3056-3060, which is incorporated by reference herein in its entirety, with slight modification. A solution of 13 mg (0.075 mmol) of 4,4'-bipyridylethylene (bpe) dissolved in 0.5 mL of ethanol was slowly layered over 0.5 mL of aqueous solution of Cd(NO$_3$)$_2$·4H$_2$O (15 mg, 0.050 mmol). Colorless crystals formed within a few days, then the crystals were taken out, and dried in air. The yield was 18 mg (69%) of MOF (4).

Sample Characterization

Fourier-transform Infrared (FT-IR) Spectroscopy: The FT-IR spectra were measured on a Perkin Elmer 16F PC FT-IR Spectrometer using KBr salt as filler in pellets form. The measurements were taken within the standard range of 400 to 4000 cm$^{-1}$. The samples were prepared by mixing 1 mg of sample with 100 mg of KBr and grounded to fine powder, which was then pressed into a pellet. The pellet was then mounted on a holder and inserted in the FT-IR spectrometer for measurements.

$^1$H-Nuclear Magnetic Resonance (NMR) Spectroscopy: The $^1$H-NMR spectra have been obtained by a JEOL JNM-LA500 spectrometer. About 4 to 5 mg of each sample were placed in NMR tube. Then, 1 to 2 mL of deuterated dimethyl sulfoxide (DMSO-d$_6$) solvent was added. The samples were shaken vigorously to dissolve the sample MOF. Sonication was used to help digesting the samples. The NMR tube was placed in the NMR spectrometer and measurements were taken. All other conditions were standard conditions. The $^1$H-NMR spectra were utilized to monitor the formation of cyclobutane derivatives during the course of the photochemical [2+2] cycloaddition reactions under different experimental conditions. The yield of UV irradiation experiments is reported as % conversion of bpe by integrating the relative area under the peaks of both bpe and the cyclobutane derivatives.

Solid-state photochemical [2+2] cycloadditions provide structural information on compounds (1) to (3), evidencing by NMR that aligned C═C olefinic double bonds are actually present within the structures of these compounds. Furthermore, the percent (%) conversion of compounds (1) and (2) indicates that compounds (1) and (2) may have infinite alignment of bpe ligands, due to matching the theoretical (%) conversions known in the art.

Powder X-Ray Diffraction (PXRD): The PXRD patterns were obtained by a Rigaku MiniFlex H diffractometer. A monochromator of CuKα1 (1.5406 Å) was used at 30 kV and 15 mA during patterns collection. The patterns obtained were recorded in the range of 2 to 900 (2θ) by continuous scanning. The scanning conditions were 1.0°/minute scanning speed and 0.02° step size. For irradiation, the fine product powder was mounted into the PXRD diffractometer sample holder by back pressing.

Elemental Analysis (CHN): The weight percent of carbon, hydrogen and nitrogen was determined by an elemental analyzer. The data were collected on a Perkin Elmer EA-2400 elemental analyzer operating under CHN mode. Around 1 mg of sample was used for each measurement, and each sample was packed tightly in a small tin container weighing 1 mg. The sample was then placed in the instrument and measurements were taken.

Elemental analysis (CHN) data obtained for compounds (1) to (4) are shown in Table 1. The results compare well to calculated elemental analysis (CHN) of reported compounds that have their powder patterns compared with synthesized compounds.

TABLE 1

Elemental analysis (CHN) data before and after UV irradiation.

| Compound | C % | H % | N % |
|---|---|---|---|
| $\{(Hbpe)_2[Zn_2(ox)_3]\}_n \cdot (H_2O) \cdot 2.2(DMF)$ (1) (Before UV irradiation) | 46.45 | 3.79 | 10.73 |
| $\{(Hbpe)_2[Zn_2(ox)_3]\}_n \cdot (H_2O) \cdot 2.2(DMF)$ (1) (calculated) | 46.76 | 4.22 | 9.24 |
| $\{(Hbpe)_2[Zn_2(ox)_3]\}_n \cdot (H_2O) \cdot 2.2(DMF)$ (1) (after UV irradiation) | 46.10 | 2.6 | 11.7 |
| $[Pb_4(ox)_3(bpe)_4(H_2O)_4]_n \cdot (NO_3)_2$ (2) (before UV irradiation) | 30.35 | 0.99 | 7.11 |
| $[Pb_4(ox)_3(bpe)_4(H_2O)_4]_n \cdot (NO_3)_2$ (2) (calculated) | 30.28 | 2.26 | 7.85 |
| $[Pb_4(ox)_3(bpe)_4(H_2O)_4]_n \cdot (NO_3)_2$ (2) (after UV irradiation) | 25.49 | 0.73 | 7.62 |
| $[Pb(bpe)(fum)]_n \cdot 0.25(H_2O)$ (3) (before UV irradiation) | 56.09 | 3.28 | 8.44 |
| $[Pb(bpe)(fum)]_n \cdot 0.25(H_2O)$ (3) (calculated) | 38.17 | 2.4 | 5.56 |
| $[Pb(bpe)(fum)]_n \cdot 0.25(H_2O)$ (3) (after UV irradiation) | 60.69 | 3.14 | 9.41 |
| $[Cd(bpe)_{1.5}(NO_3)_2(H_2O)]_n$ (4) (experimentally determined) | 40.9 | 3.34 | 13.06 |
| $[Cd(bpe)_{1.5}(NO_3)_2(H_2O)]_n$ (4) (calculated) | 40.96 | 3.25 | 13.27 |

Apart from compound (4), which was successfully reproduced with experimental elemental analysis results in a match with calculated values with a maximum difference of 0.05%, the maximum difference in compound (2) is less than 1.5% in hydrogen, or hydrogen and nitrogen for compound (1). Such differences may be due to defects in the MOF structure, and non-constant chemical species at the edges of the infinite MOF structure.

The slight change between before and after UV irradiation may be explained by the change in water or solvent content due to UV irradiation. The significant change in compound 3, which was UV irradiated for 50 hours for elemental analysis (CHN), despite reaching full conversion after only 5 hours of UV irradiation, may be due to excess UV irradiation changing some structural features within the lattice structure, such as losses of coordinated ligands.

Thermogravimetric Analysis (TGA): The thermogravimetric analysis (TGA) was done with a TA SDT 2960 thermal analyzer. The experiments conditions were set to ramp from room temperature to 600° C. at a rate of 5° C./min under nitrogen atmosphere at a flow rate of 50 mL/min. About 3 to 5 mg samples were used, each exemplary compound (1) to (4) sample being prepared just prior the TGA experiment to minimize moisture exposure.

Ultraviolet (UV) Irradiation: UV irradiation was performed by a Luzchem LZC-DEV photoreactor. About 4 to 5 mg of each sample was placed between two glass slides and placed on its side edge for irradiation. Both sides were irradiated simultaneously using the side lamps of the photoreactor. Each compound was UV irradiated for 5, 10, 15, 30, and 50 hours for NMR studies. Two more samples of each exemplary compound were UV irradiated for 50 hours for FT-IR and elemental analysis (CHN). The single crystal of compound (4) was placed on a slide of glass, then UV irradiated from the top UV lamps for 5, 20, and 50 hours for single crystals photoreactivity studies with NMR. Another batch of single crystal samples were irradiated for 50 hours for TGA. Powder samples of compound (4) were obtained by manual grinding of its single crystals for 10 minutes using a mortar and pestle, then the powder samples were exposed to UV irradiation for 5, 10, 20, 30, and 50 hours. A further batch of ground crystals samples (10 and 20 minute grinding period) were UV irradiated for 50 hours, then used for TGA.

Referring now to the drawings, wherein like reference numerals designate identical or corresponding parts throughout the several views.

FIG. 1 shows a pictorial representation of the syntheses of the three exemplary MOFs, $\{(Hbpe)_2[Zn_2(ox)_3]\}_n \cdot (H_2O) \cdot 2.2(DMF)$, $[Pb_4(ox)_3(bpe)_4(H_2O)_4]_n \cdot (NO_3)_2$, and $[Pb(bpe)(fum)]_n \cdot 0.25(H_2O)$.

Photodimerization Studies

Figure 2A:
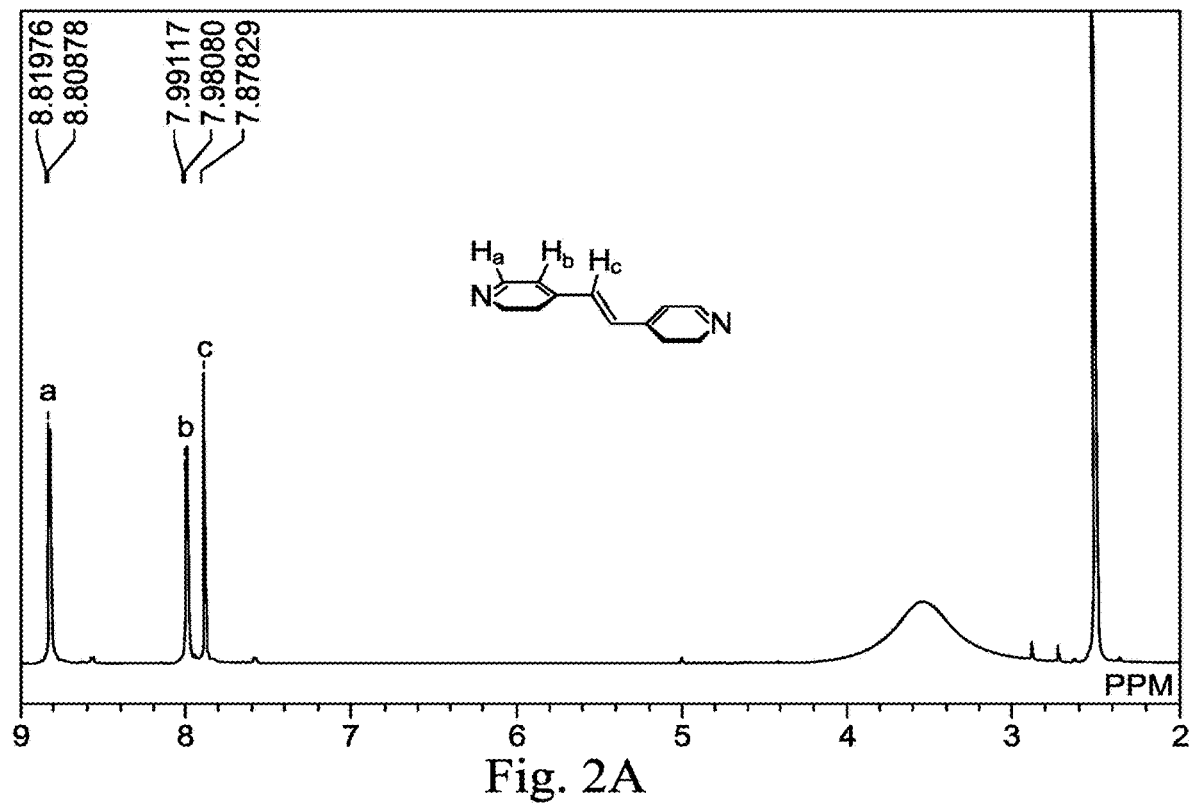
FIG. 2A shows the $^1$H-NMR spectrum in DMSO-$d_6$ of compound (1), $\{(Hbpe)_2[Zn_2(ox)_3]\}_n \cdot (H_2O) \cdot 2.2(DMF)$, before UV irradiation.

Compounds (1) to (3): The photoreactivity of exemplary compounds (1) to (3) was studied by monitoring photochemical [2+2] cycloadditions by $^1$H-NMR spectroscopy. Each compound was analyzed with $^1$H-NMR spectroscopy before and after UV irradiation to determine if the compounds are photochemically active or not. FIG. 2 to 4 show $^1$H-NMR spectra of each compound before and after UV irradiation.

Figure 2B:
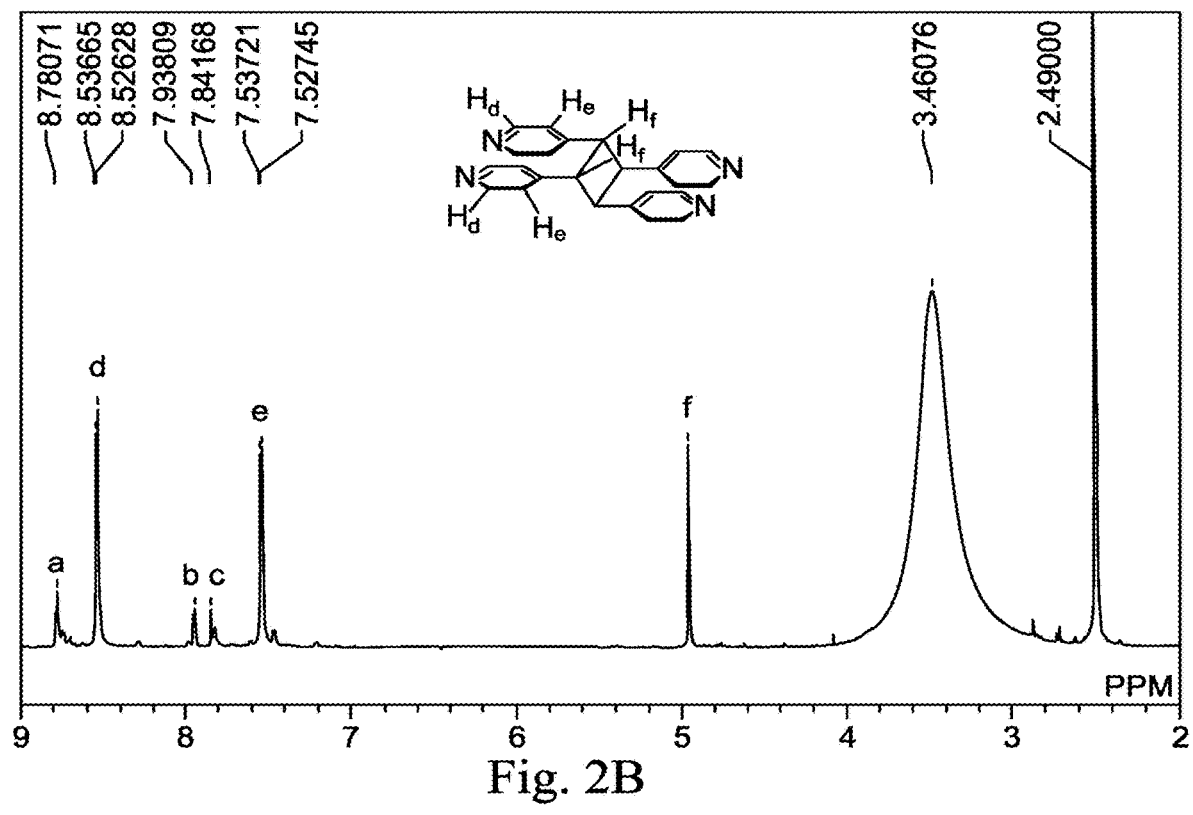
FIG. 2B shows the $^1$H-NMR spectrum in DMSO-$d_6$ of compound (1) after 30 hours of UV irradiation (DMSO-$d_6$)
Figure 3A:
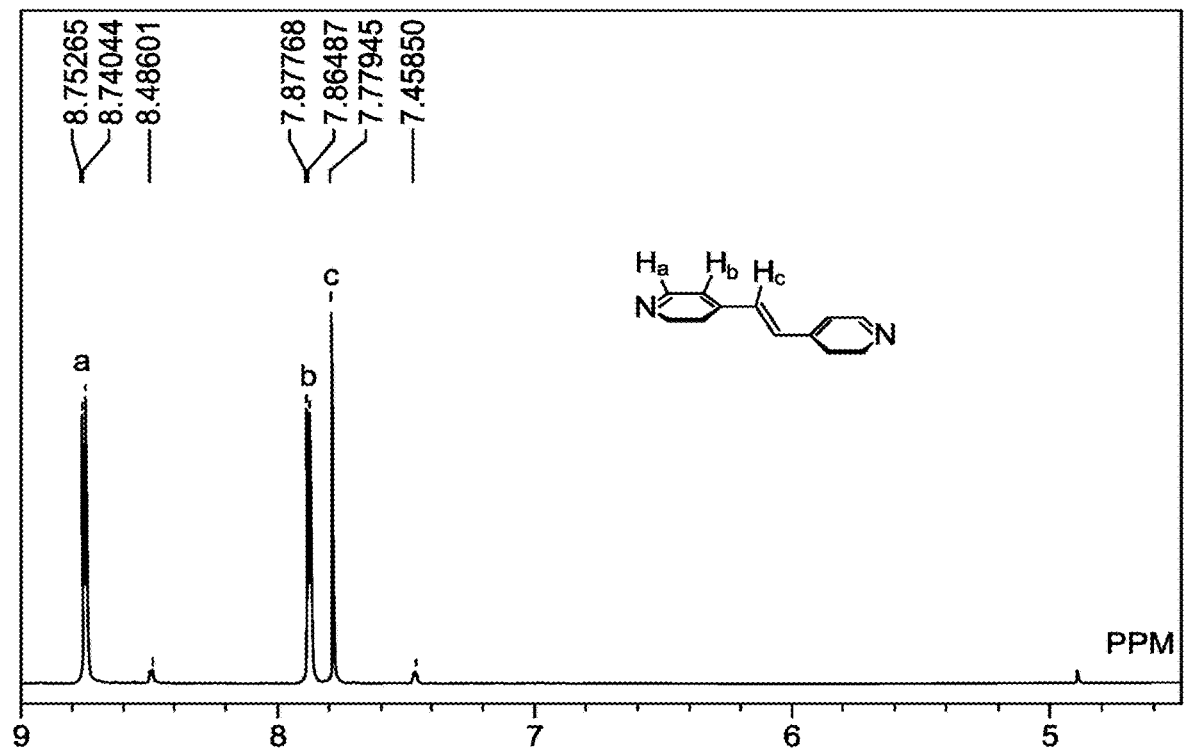
FIG. 3A shows the $^1$H-NMR spectrum in DMSO-$d_6$ of compound (2), $[Pb_4(ox)_3(bpe)_4(H_2O)_4]_n \cdot (NO_3)_2$, before UV irradiation.
Figure 3B:
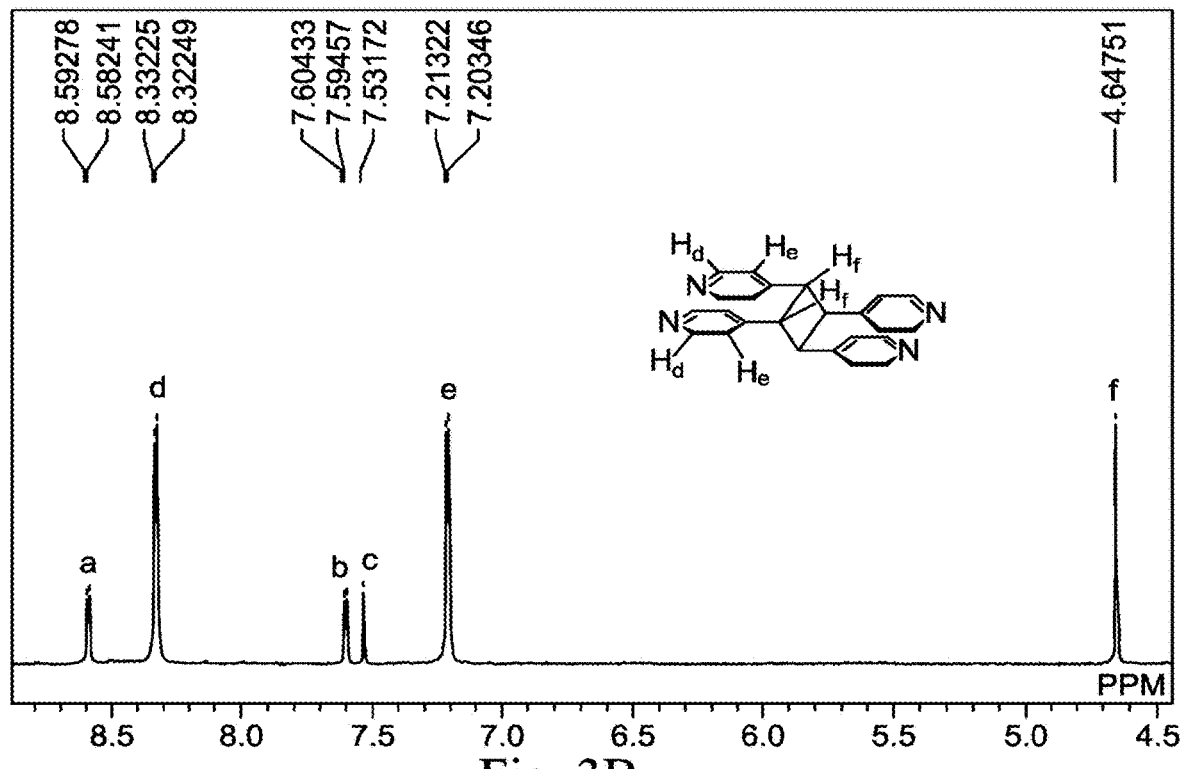
FIG. 3B shows the $^1$H-NMR spectrum in DMSO-$d_6$ of compound (2) after 30 hours of UV irradiation.
Figure 4A:
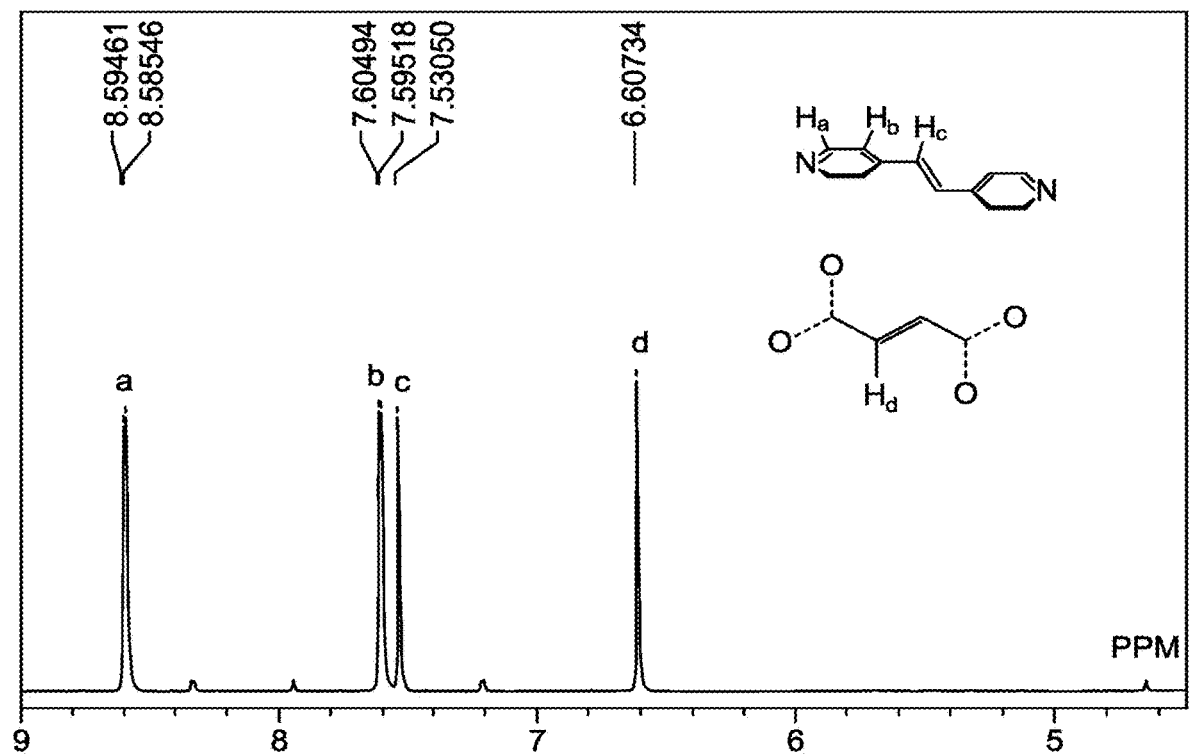
FIG. 4A shows the $^1$H-NMR spectrum in DMSO-$d_6$ of compound (3), $[Pb(bpe)(fum)]_n \cdot 0.25(H_2O)$, before UV irradiation.
Figure 4B:
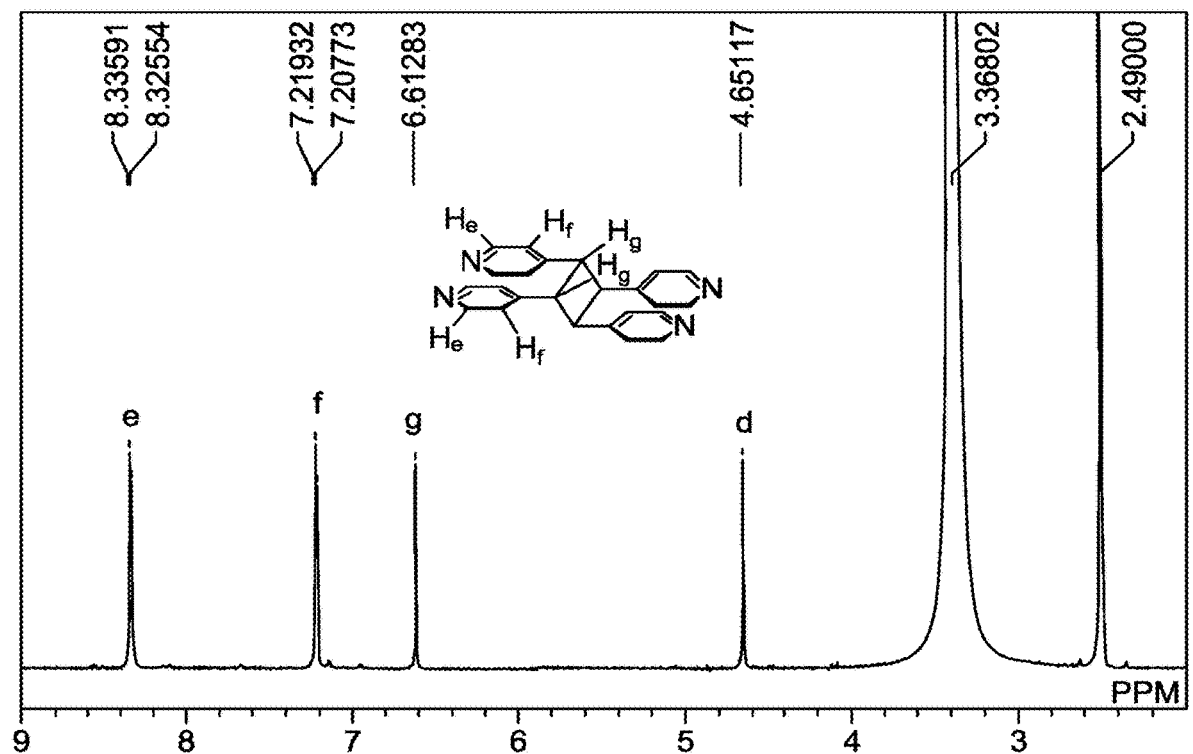
FIG. 4B shows the $^1$H-NMR spectrum in DMSO-$d_6$ of compound (3) after 5 hours of UV irradiation.

After UV irradiation, the $^1$H-NMR spectra of compounds (1) and (2), seen in FIGS. 2B and 3B, show the decrease in intensity of a, b, and c signals, belonging to photochemically unreacted bpe, and the appearance of d, e, and f signals, belonging to the photochemical [2+2] cycloaddition reaction product, rctt-tetrakis(4-pyridyl)cyclobutane (tpcb). However, in the case of compound (3), after UV irradiation $^1$H-NMR spectrum in FIG. 4B shows complete disappearance of bpe signals, i.e., a, b, and c signals in FIG. 4A, which indicates complete conversion of bpe ligands within compound (3) to the rctt-tetrakis(4-pyridyl)cyclobutane (tpcb) product.

The $^1$H-NMR spectra of the MOFs of exemplary compounds (1) to (3) are photoreactive and undergo photochemical [2+2] cycloaddition reaction in the solid-state. However, a further assessment of the photochemical behavior of these MOFs would be informative, particularly regarding the achievement of maximum bpe conversion.

Figure 5:
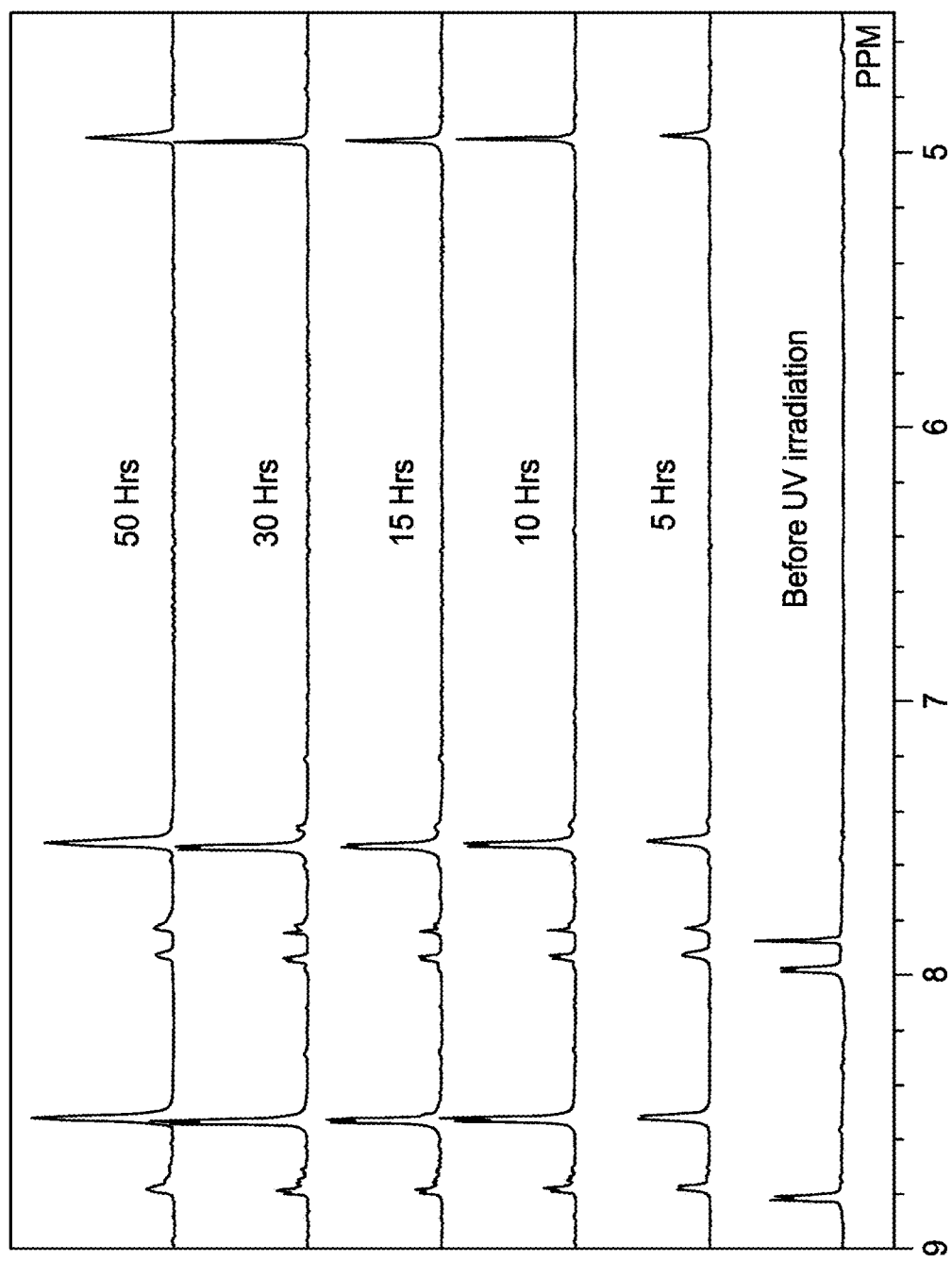
FIG. 5 shows the $^1$H-NMR spectrum in DMSO-$d_6$ of compound (1), $\{(Hbpe)_2[Zn_2(ox)_3]\}_n \cdot (H_2O)_n \cdot 2.2(DMF)$, after UV irradiation for time intervals of 5, 10, 15, 30, and 50 hours, to assess maximum bpe conversion.
Figure 6:
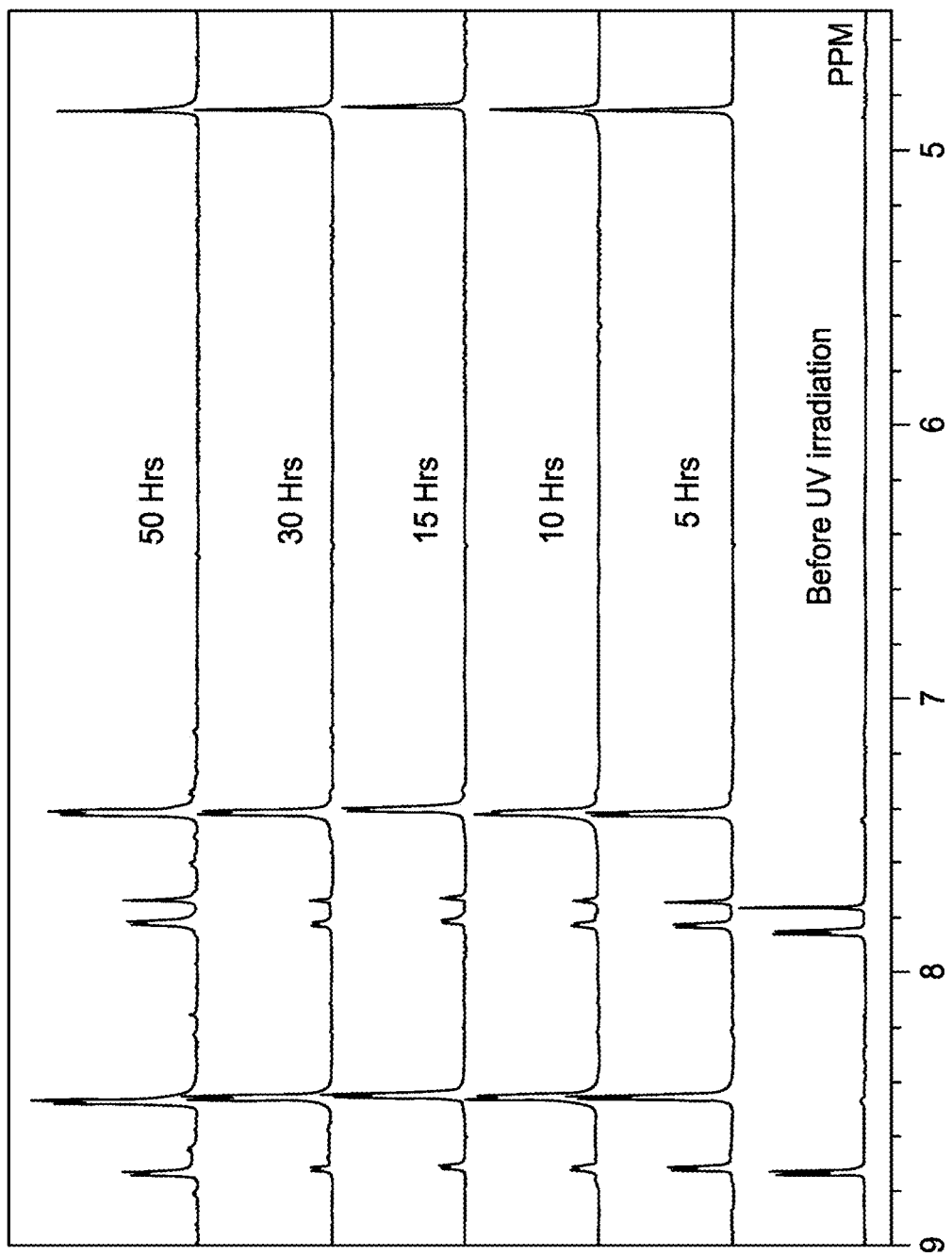
FIG. 6 shows the $^1$H-NMR spectrum in DMSO-$d_6$ of compound (2), $[Pb_4(ox)_3(bpe)_4(H_2O)_4]_n \cdot (NO_3)_2$, after UV irradiation for time intervals of 5, 10, 15, 30, and 50 hours, to assess maximum bpe conversion.

In order to assess maximum bpe conversion, compounds (1) and (2) were UV irradiated for time intervals of 5, 10, 15, 30, and 50 hours, then $^1$H-NMR spectra were recorded. FIG. 5 and FIG. 6 show the $^1$H-NMR spectra of each compound for 5, 10, 15, 30, and 50 hours. The percentage conversion by UV irradiation was calculated from the obtained $^1$H-NMR spectra of compounds (1) and (2) by integrating the relative peaks areas for both bpe and rctt-tpcb as shown in FIG. 7A to 8E. FIG. 7A to 7E show $^1$H-NMR spectra in DMSO-$d_6$ of compound (1) after 5, 10, 15, 30, and 50 hours (maximum conversion) of UV irradiation. FIG. 8A to 8E show ¹H-NMR spectra in DMSO-d₆ of compound (2) after 5, 10, 15, 30 (maximum conversion), and 50 hours of UV irradiation. Table 2, below, summarizes the percent conversion of bpe to rctt-tpcb in each UV irradiated sample for compounds (1) and (2).

TABLE 2

Exposure time and % conversion calculation for compounds (1) and (2) based on ¹H-NMR spectroscopy.

| Compound Identity | Time of exposure, h | rctt isomer, % | Unreacted bpe, % | Bpe peaks total area | rctt isomer peaks total area | Total area of both |
|---|---|---|---|---|---|---|
| 1 | 5 | 68.75 | 31.25 | 2.5 | 5.5 | 8.0 |
|   | 10 | 83.00 | 17.00 | 0.4 | 2.2 | 2.6 |
|   | 15 | 85.50 | 14.50 | 1.9 | 11.2 | 13.1 |
|   | 30 | 87.14 | 12.86 | 1.8 | 12.2 | 14.0 |
|   | 50 | 89.04 | 10.96 | 1.7 | 13.4 | 15.1 |
| 2 | 5 | 71.20 | 28.80 | 2.7 | 6.6 | 9.2 |
|   | 10 | 84.23 | 15.77 | 2.4 | 12.6 | 14.9 |
|   | 15 | 88.15 | 11.85 | 2.4 | 17.6 | 20.0 |
|   | 30 | 88.43 | 11.57 | 2.5 | 19.1 | 21.6 |
|   | 50 | 79.91 | 20.09 | 2.2 | 8.6 | 10.7 |

Figure 9:
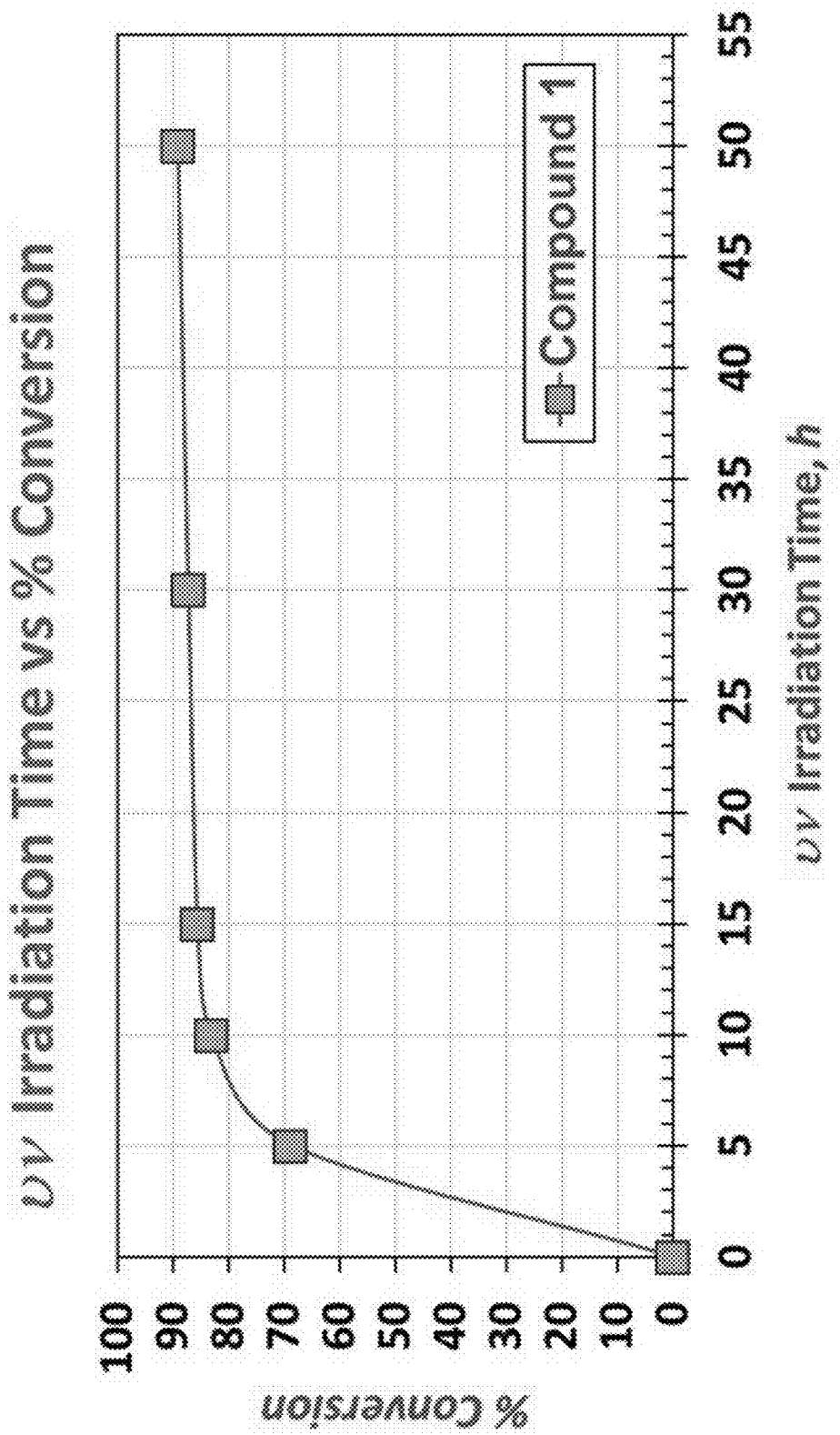
FIG. 9 shows a plot of the percent (%) conversion of bpe to rctt-tpcb over time under UV irradiation using compound (1)
Figure 10:
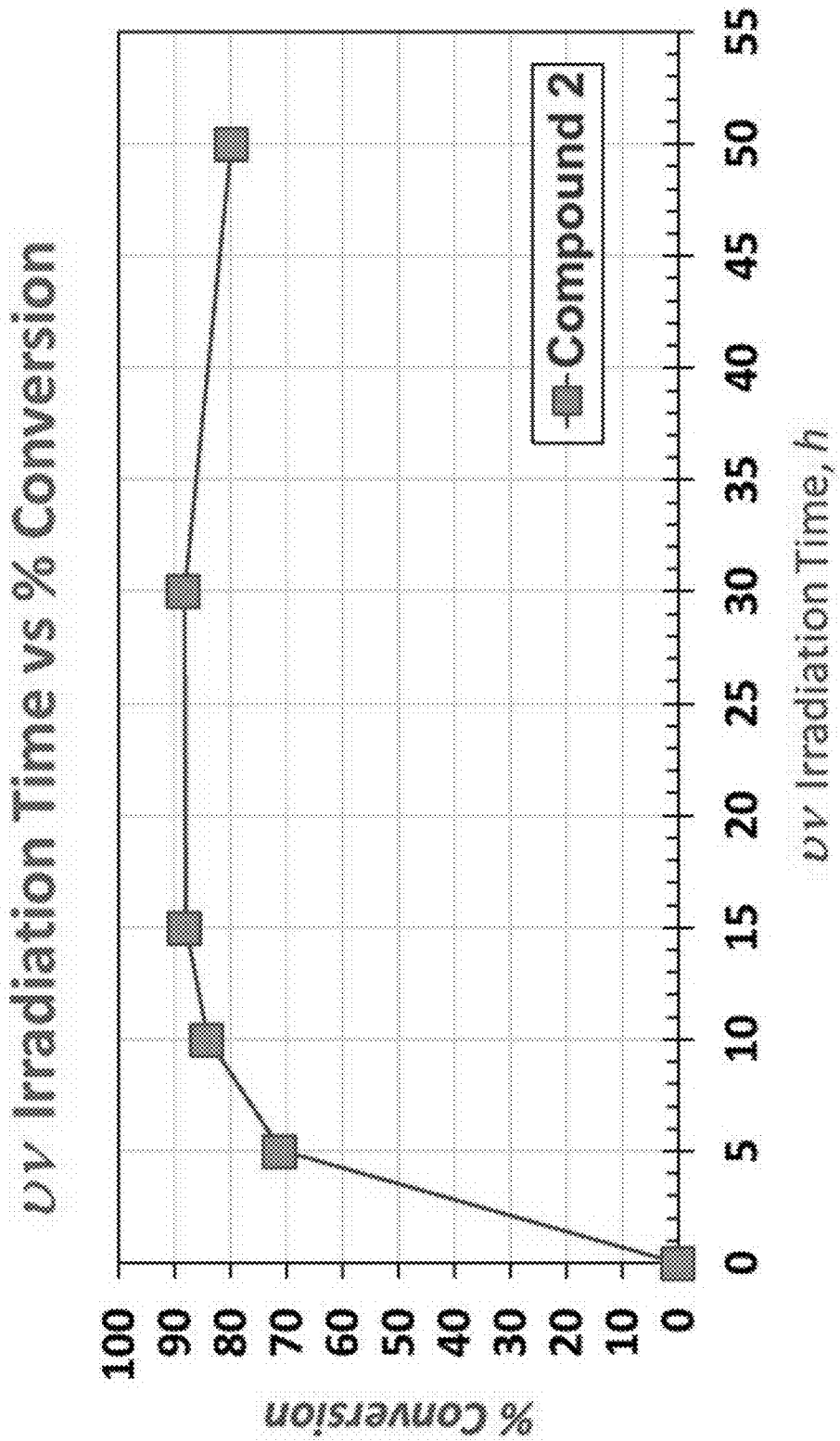
FIG. 10 shows a plot of the percent (%) conversion of bpe to rctt-tpcb over time under UV irradiation for compound (2)

The data of Table 2 provides an insight into the photochemical behavior of compounds (1) and (2). A graph of this data is seen in FIG. 9 for compound (1) and in FIG. 10 for compound (2), plotting the percent (%) conversion against time in each case.

Figure 7A:
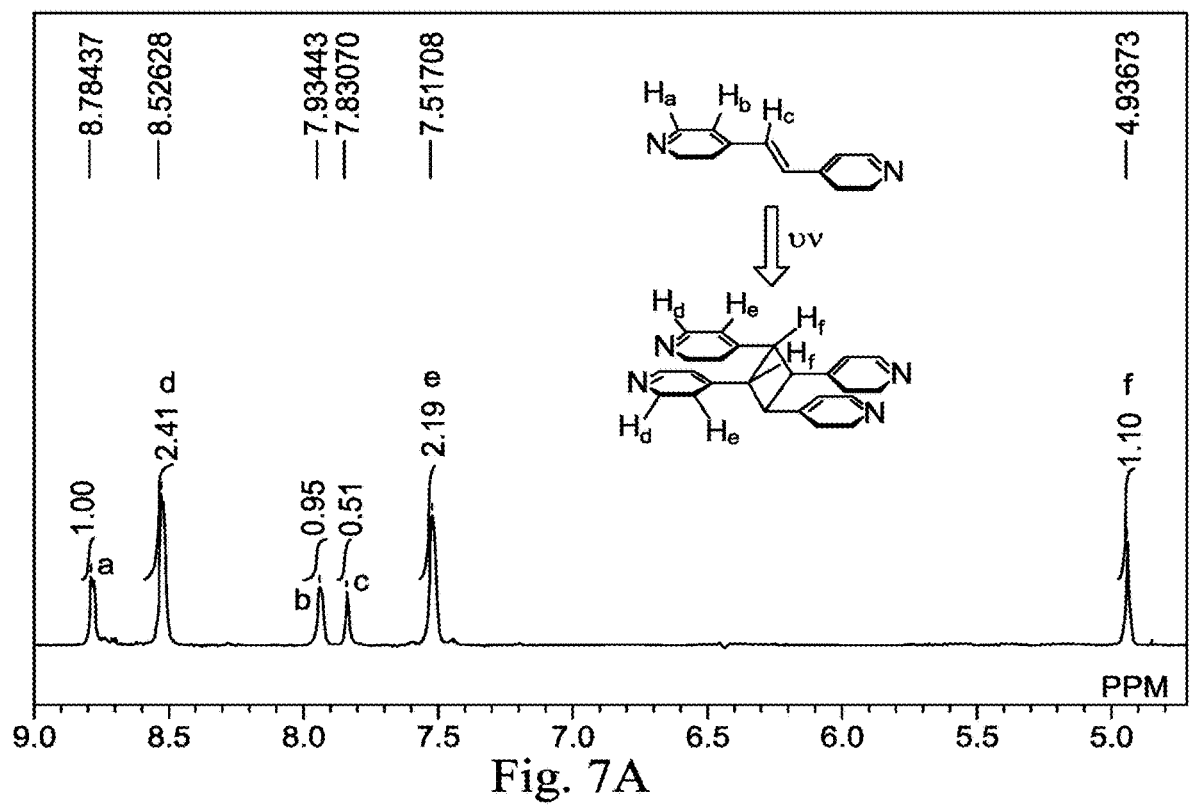
FIG. 7A shows an $^1$H-NMR spectrum in DMSO-$d_6$ of compound (1), $\{(Hbpe)_2[Zn_2(ox)_3]\}_n \cdot (H_2O) \cdot 2.2(DMF)$, after 5 hours of UV irradiation.
Figure 7B:
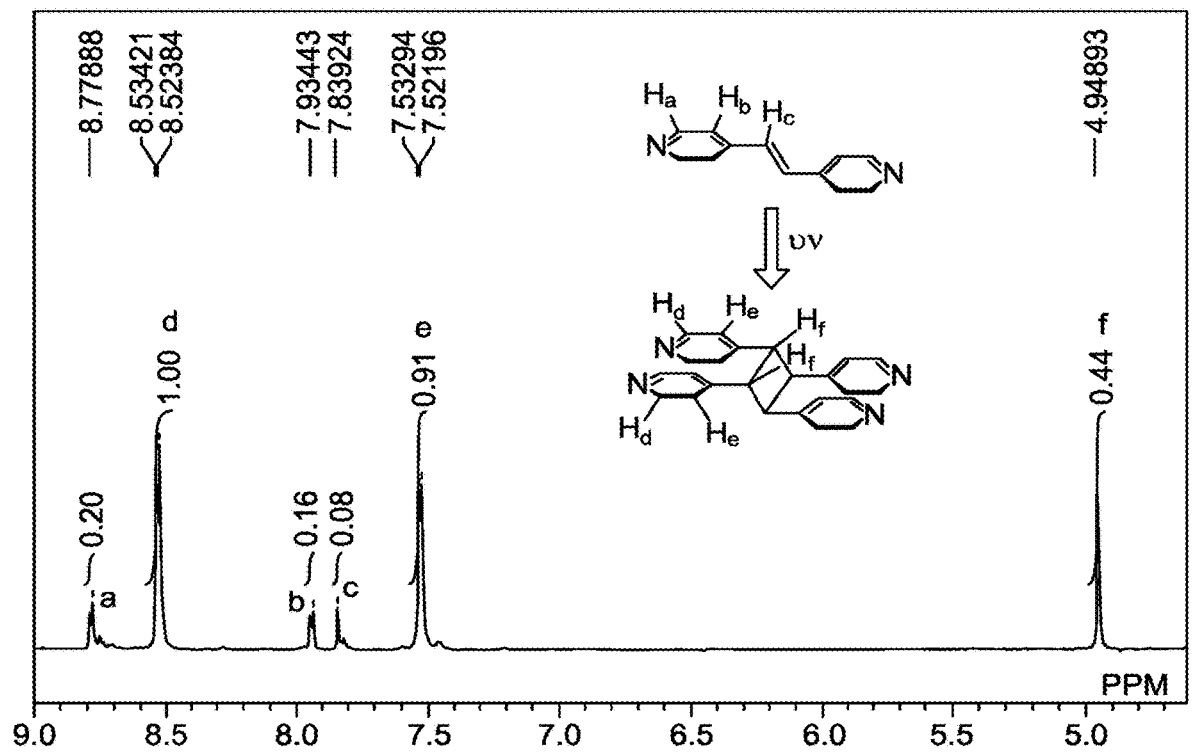
FIG. 7B shows an $^1$H-NMR spectrum in DMSO-$d_6$ of compound (1) after 10 hours of UV irradiation.
Figure 7C:
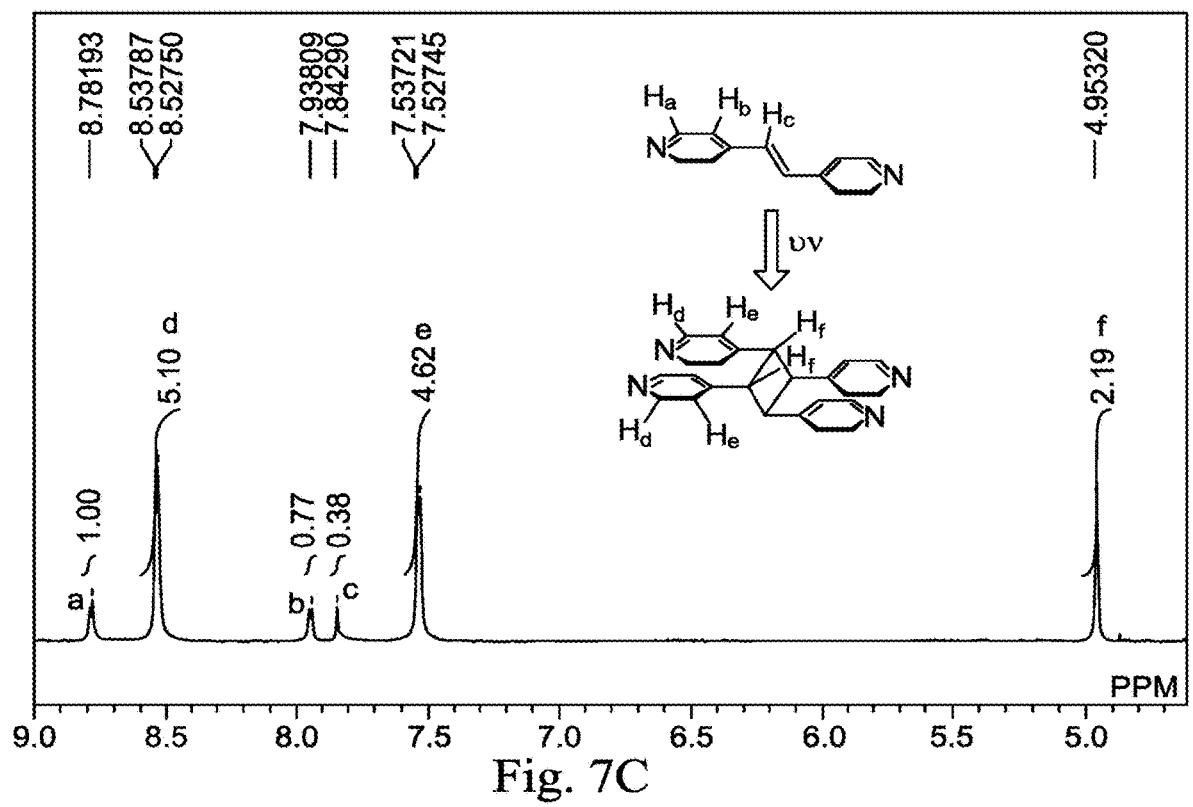
FIG. 7C shows an $^1$H-NMR spectrum in DMSO-$d_6$ of compound (1) after 15 hours of UV irradiation.
Figure 7D:
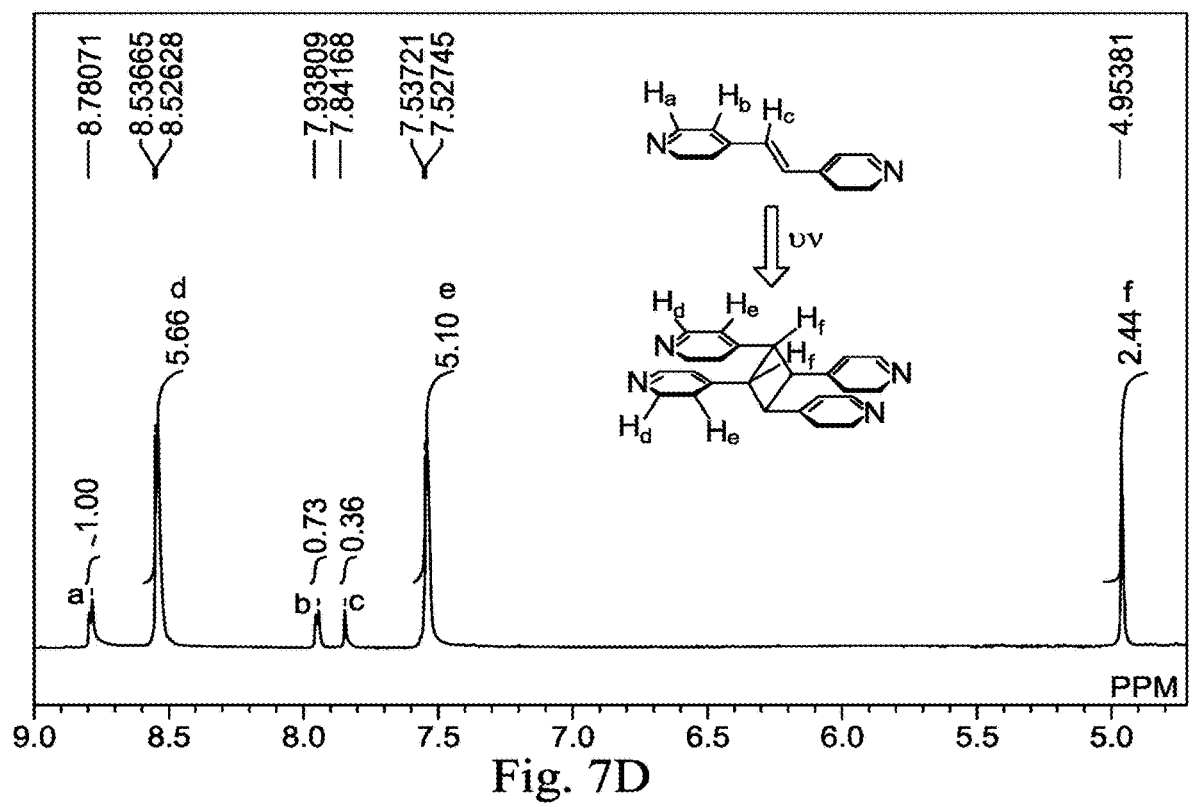
FIG. 7D shows an $^1$H-NMR spectrum in DMSO-$d_6$ of compound (1) after 30 hours of UV irradiation.
Figure 7E:
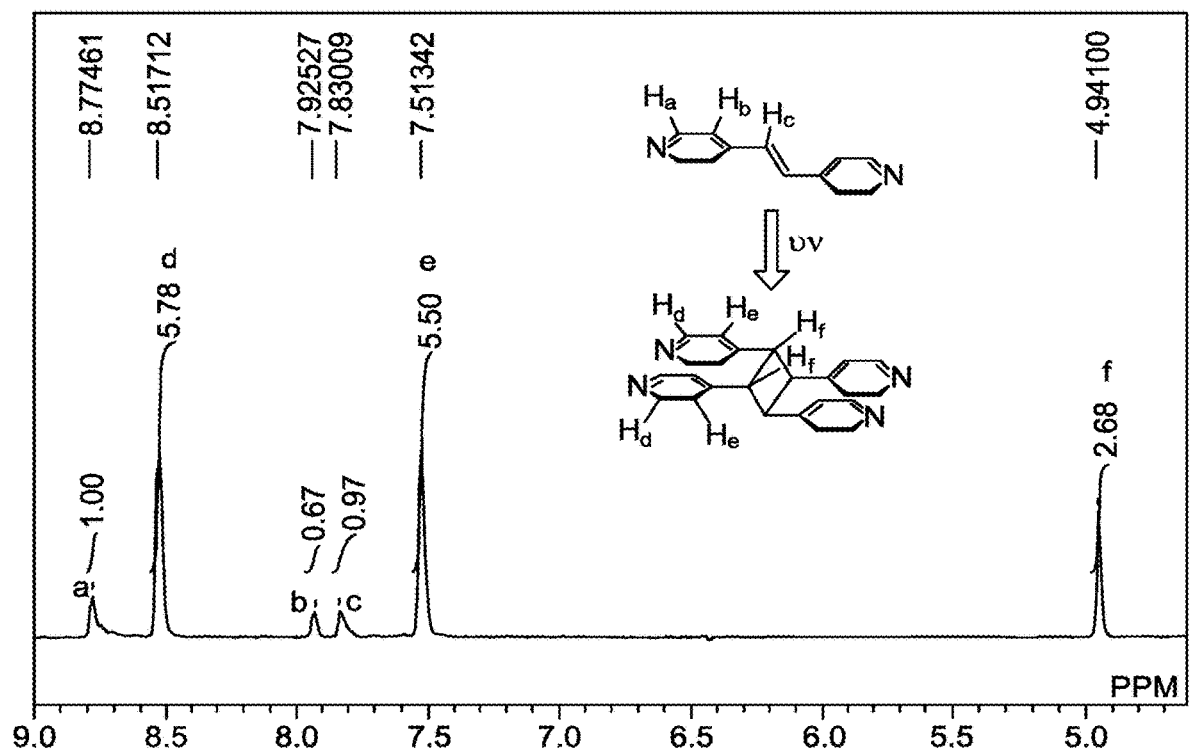
FIG. 7E shows an $^1$H-NMR spectrum in DMSO-$d_6$ of compound (1) after 50 hours of UV irradiation indicating maximum conversion.

The calculated maximum percent conversion for exemplary compound (1) was found to be around 89%, as indicated in Table 2, e.g., at least 75, 77.5, 80, 82.5, 85, 87.5, 88, 89, 90, 91, 92, 93, 94, 95% or more and/or up to 99, 97.5, 95, 94, 93, 92, 91, 90, 89, or 88%, which was achieved after 50 hours of UV irradiation in the solid-state. As seen in FIG. 7E, the maximum percent conversion of compound (1) is substantially achieved after 10 hours of UV irradiation, because the conversion curve rises only slowly after 10 hours, i.e., at least 83, 84, 85, 86, or 87% conversion is achieved after 10 hours of UV irradiation. The difference in percent conversion between 10 and 50 hours of UV irradiated samples of compound (1) may be no more than 10, 8, 6, 4, or 2% of the total conversion achievable, as shown in Table 2 despite the 5-fold increased UV irradiation time. The maximum percent conversion may be reached within 15, 25, 35, 45, 50, 55, or 60 minutes of UV irradiation.

Figure 8A:
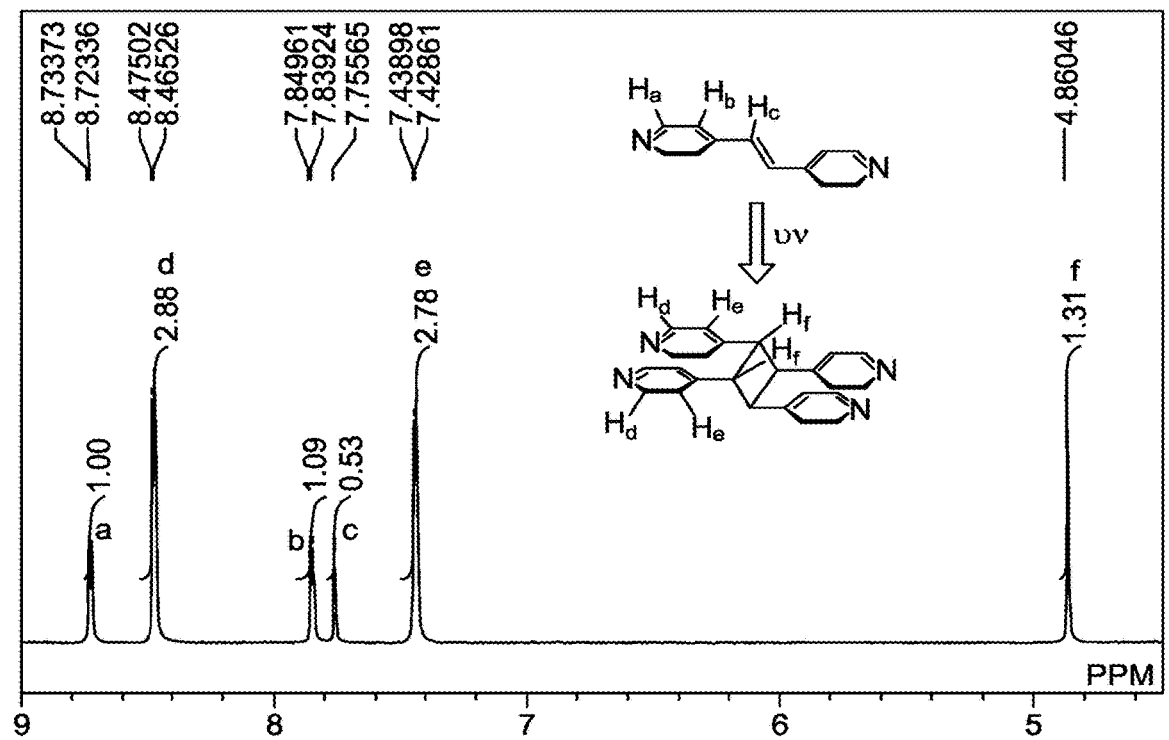
FIG. 8A shows an $^1$H-NMR spectrum in DMSO-$d_6$ of compound (2), $[Pb_4(ox)_3(bpe)_4(H_2O)_4]_n \cdot (NO_3)_2$, after 5 hours of UV irradiation.
Figure 8B:
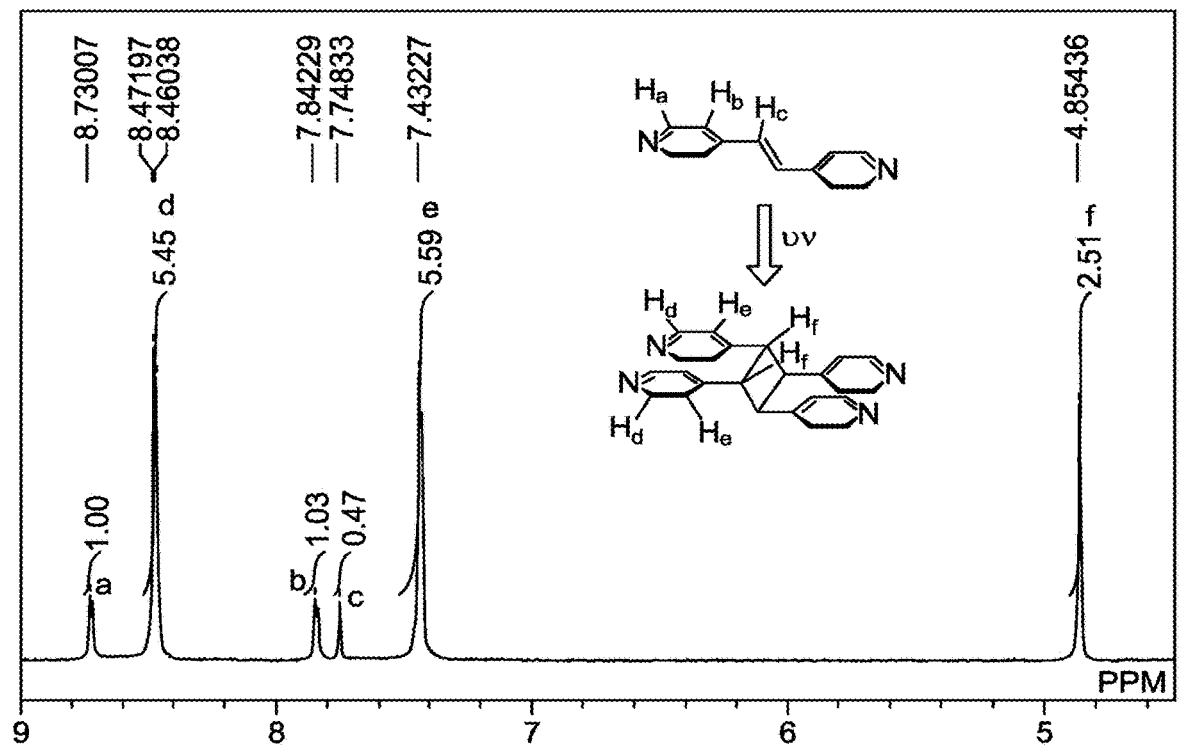
FIG. 8B shows an $^1$H-NMR spectrum in DMSO-$d_6$ of compound (2) after 10 hours of UV irradiation.
Figure 8C:
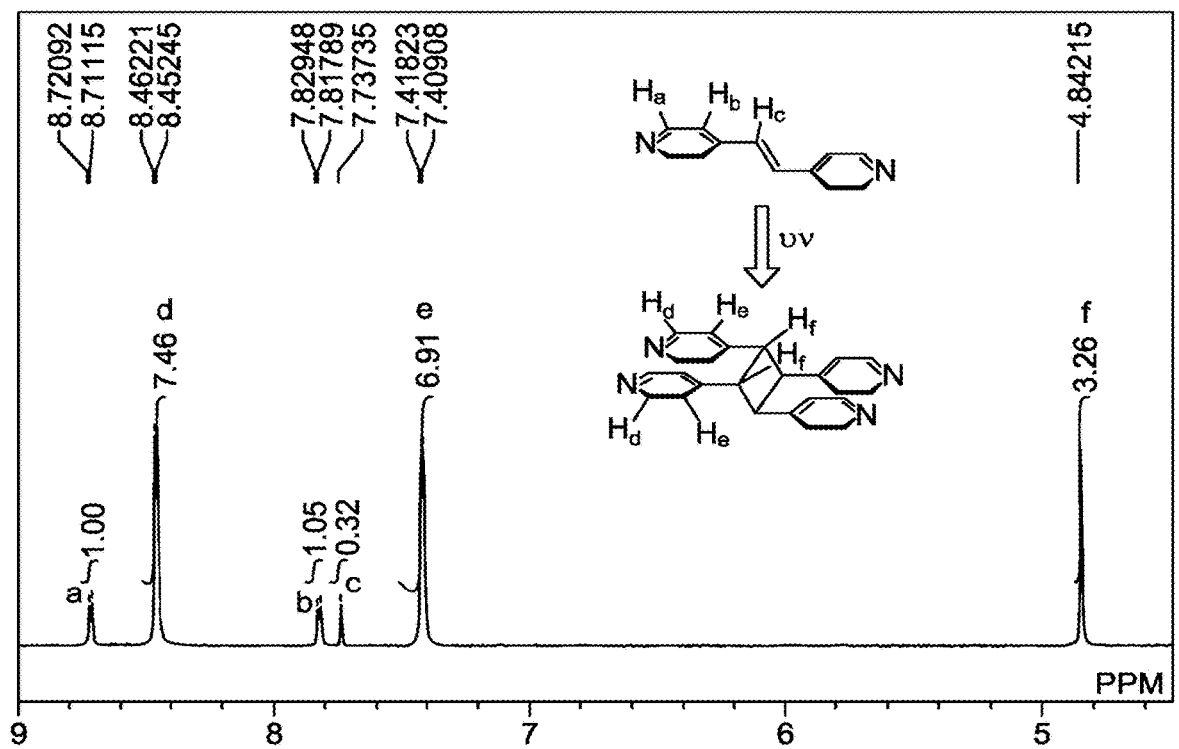
FIG. 8C shows an $^1$H-NMR spectrum in DMSO-$d_6$ of compound (2) after 15 hours of UV irradiation.
Figure 8D:
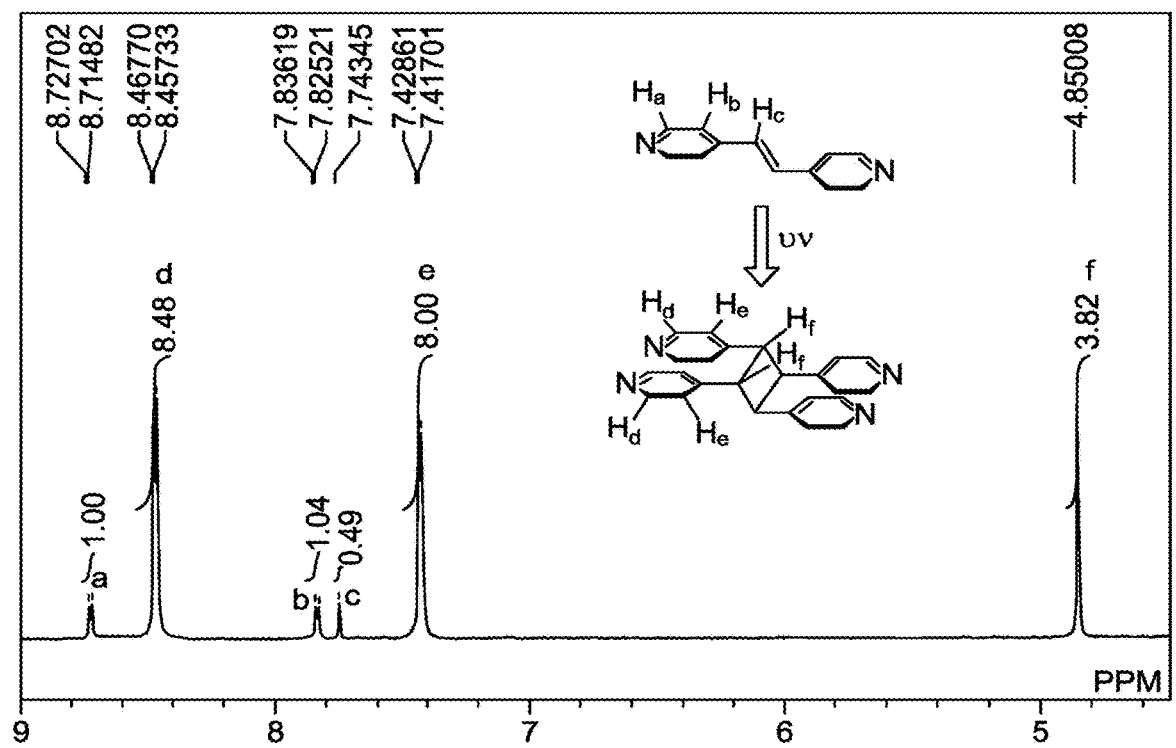
FIG. 8D shows an $^1$H-NMR spectrum in DMSO-$d_6$ of compound (2) after 30 hours of UV irradiation indicating maximum conversion.
Figure 8E:
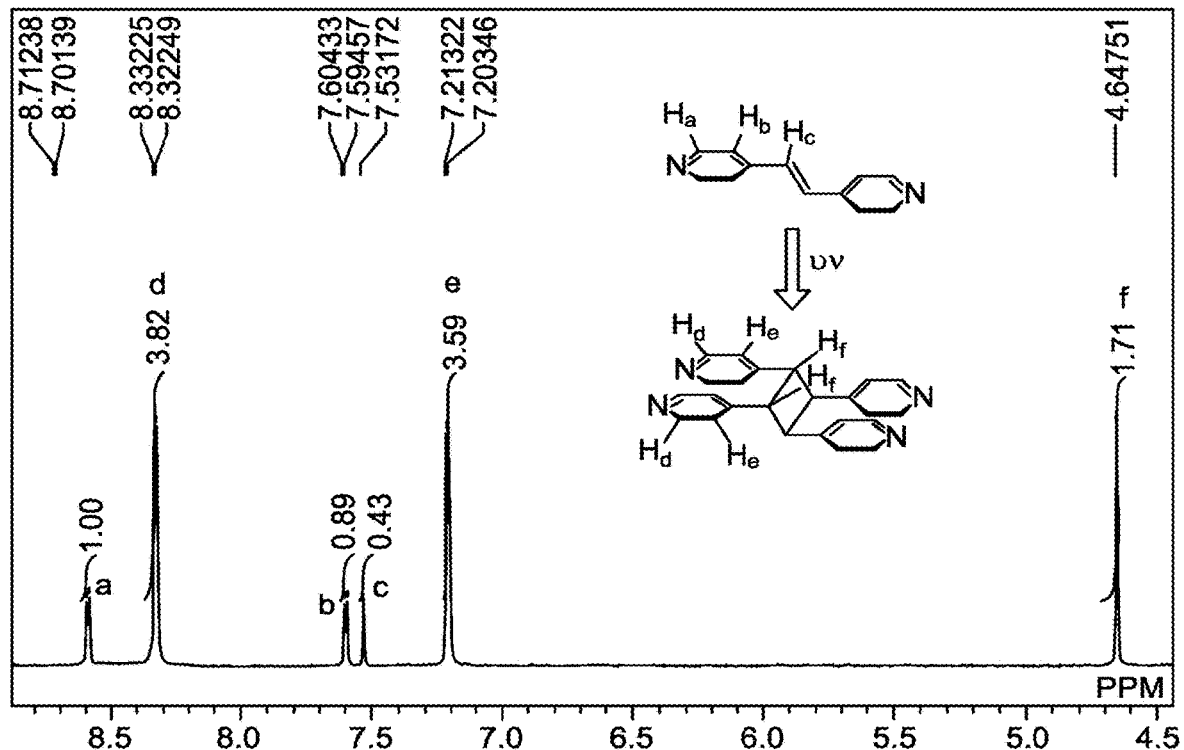
FIG. 8E shows an $^1$H-NMR spectrum in DMSO-$d_6$ of compound (2) after 50 hours of UV irradiation.

A maximum conversion of bpe in exemplary compound (2) may be, for example, 88% and/or at least 80, 82.5, 85, 86, 87, 88, 89, 90, or 91% and/or up to 95, 92.5, 91, 90, 89, or 87.5%, from photochemical reaction to produce an rctt-tpcb isomer within 15 hours of UV irradiation as indicated in Table 2 and FIG. 8C. The maximum photochemical conversion of bpe to rctt-tpcb for both compounds (1) and (2) may be comparably high, compound (2) may achieve its maximum conversion faster than compound (1). For example, 10, 12, 14, 15, 16, or 17.5 hours of UV irradiation may be sufficient for compound (2) to achieve its maximum conversion, while up to triple the time, e.g., 30, 35, 40, 45, 50, 55, or 60 hours, may be required for compound (1) to achieve its maximum conversion. In addition, the percent conversion of bpe to rctt-tpcb in compound (2) may remain constant (e.g., within 5, 2.5, 2, 1, 0.5 or 0.1% of constant) after UV irradiation time exceeding the maximum conversion, for example, from 15 to 30 hours, or 17.5 to 35 hours. After a stable period following reaching the maximum, the percent conversion may decrease (e.g., due to reverse reaction and/or decomposition) upon further UV irradiation time after the constant period, as shown in Table 2 and FIG. 10.

Accordingly, aspects of the invention pay provide sensitizer and/or catalyst MOFs with reversible photochemical properties, particularly wherein photochemical [2+2]cycloadditions can be reversed under specific conditions (such as prolonged UV irradiation, e.g., at least 40, 45, 50, 55, 60, 75, or 90 minutes, and/or threshold photonic loads, and/or thermal loads). Inventive materials may thus be suitable as photo-switches, sensors, and/or in optical data storage. Prolonged UV irradiation of inventive compounds, particularly exemplary compound (2), may trigger reversible reactions without requiring any thermal treatment.

Different photochemical behavior of inventive MOFs, e.g., differences between compounds (1) and (2), may be steered by lattice structure differences, i.e., the photochemical behavior of inventive compounds may be modified by the selection of ligands and/or substituents, which may affect the crystalline packing. The photochemical product of compound (2) formed faster experimentally than compound (1), yet compound (2)'s cyclized product reverted to bpe, unlike compound (1) under the same conditions. The observed reversibility may alternatively or additionally indicate that the photochemical product is less stable in compound (2) than it is in compound (1), which may be due to a less ideal misalignment of bpe ligands within compound (2), as discussed below regarding PXRD analysis. Crystalline misalignment may induce a slight strain on rctt-tpcb that allows it to undergo the reversible photochemical reaction. Alternatively or additionally, MOFs needing comparatively longer times to reach maximum conversion, such as compound (1), may require more and/or larger steps of internal molecular motion, as discussed below regarding PXRD analysis section, before undergoing the photochemical [2+2] cycloaddition reaction. The photochemical product of compound (2) may be more kinetically favored than that of compound (1), and/or the photochemical product of compound (1) may be thermodynamically favored over that of compound (2).

Figure 11A:
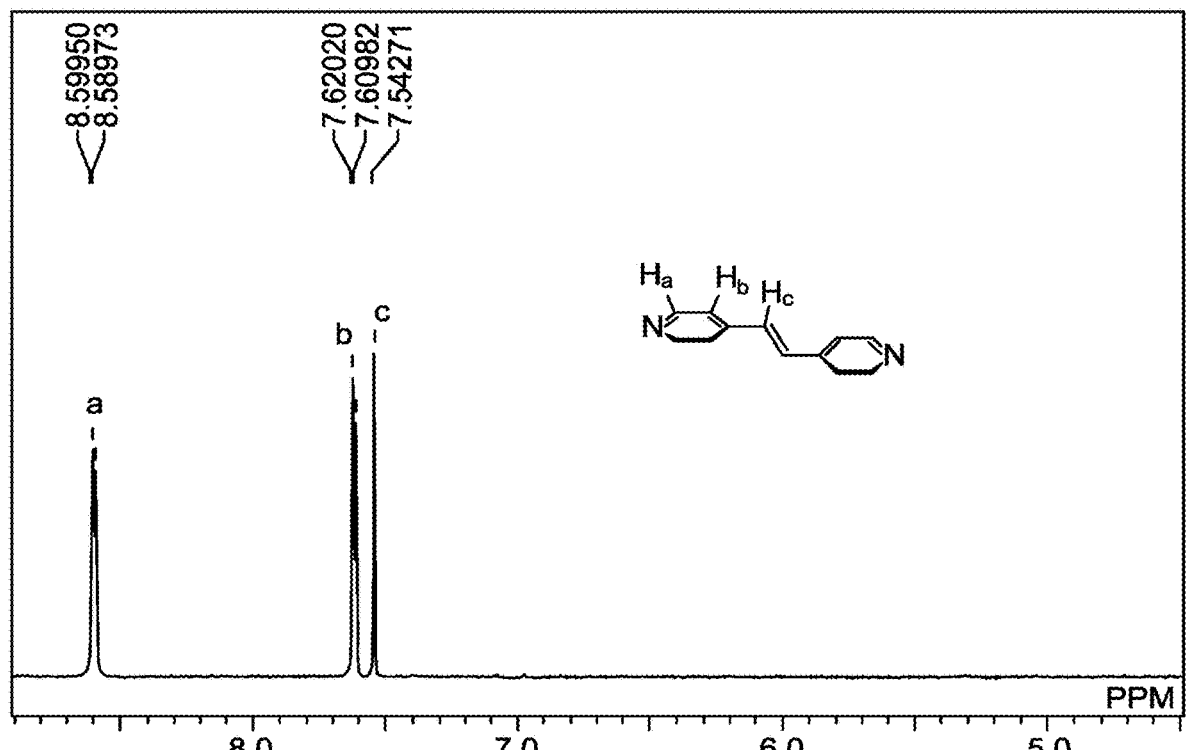
FIG. 11A shows an $^1$H-NMR spectrum in DMSO-$d_6$ of compound (4), $[Cd(bpe)_{1.5}(NO_3)_2(H_2O)]_n$, crystals before UV irradiation.

Compound (4)—Single Crystal Photodimerization: The photoreactivity of compound (4), [Cd(bpe)$_{1.5}$(NO$_3$)$_2$ (H$_2$O)]$_n$, to photochemical [2+2] cycloaddition can be followed by ¹H-NMR spectroscopy. The MOF from compound (4) can be produced in single crystal form by modified layering method as described in *Inorg. Chem.* 1999, 38(13), 3056-3060. FIG. 11A shows an ¹H-NMR spectrum of these crystals from compound (4) before UV irradiation. Based on the reported structure reproduced in FIG. 11B, the maximum expected percent conversion was believed to be about 67%. Crystals of were UV irradiated for 5, 20, and 50 hours, to investigate the photochemical behavior of the MOF, whereby the percent conversion was calculated by integrating the relative peaks areas of bpe and rctt-tpcb in the obtained ¹H-NMR spectra as shown in FIG. 12A to 12C.

Figure 12A:
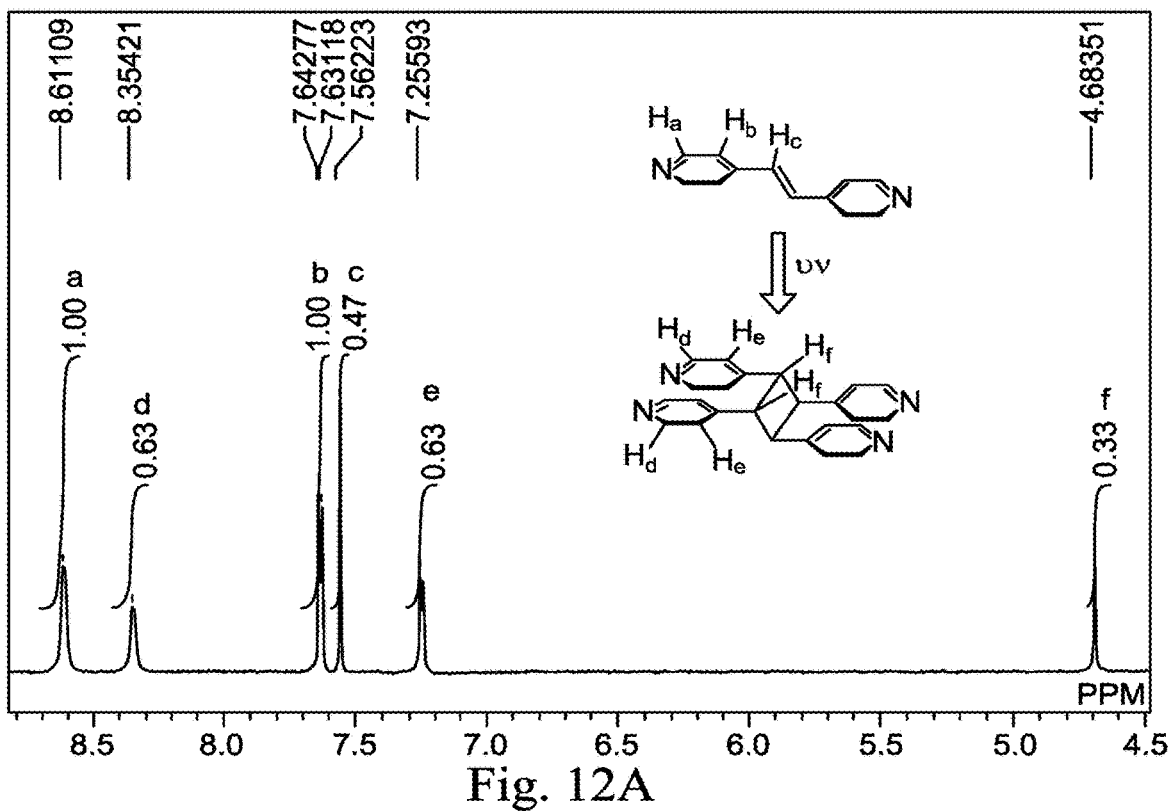
FIG. 12A shows an $^1$H-NMR spectrum in DMSO-$d_6$ of compound (4) crystals after 5 hours of UV irradiation.
Figure 12B:
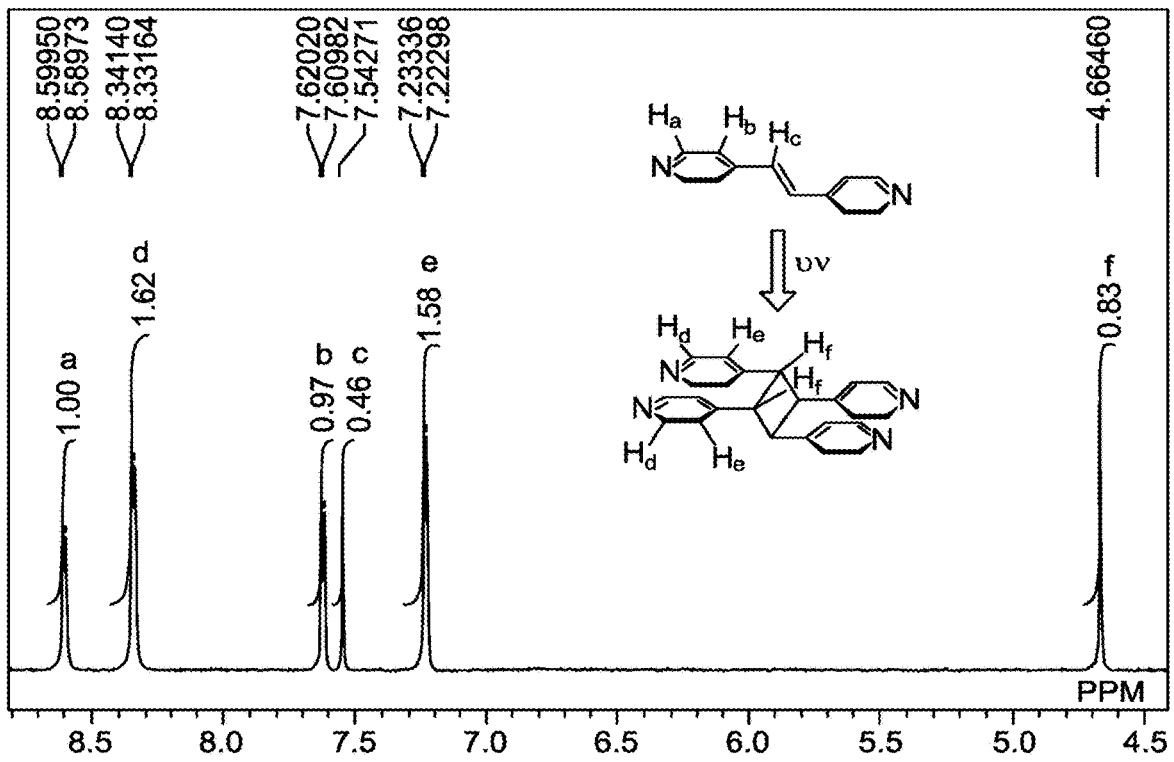
FIG. 12B shows an $^1$H-NMR spectrum in DMSO-$d_6$ of compound (4) crystals after 20 hours of UV irradiation (DMSO-$d_6$)
Figure 12C:
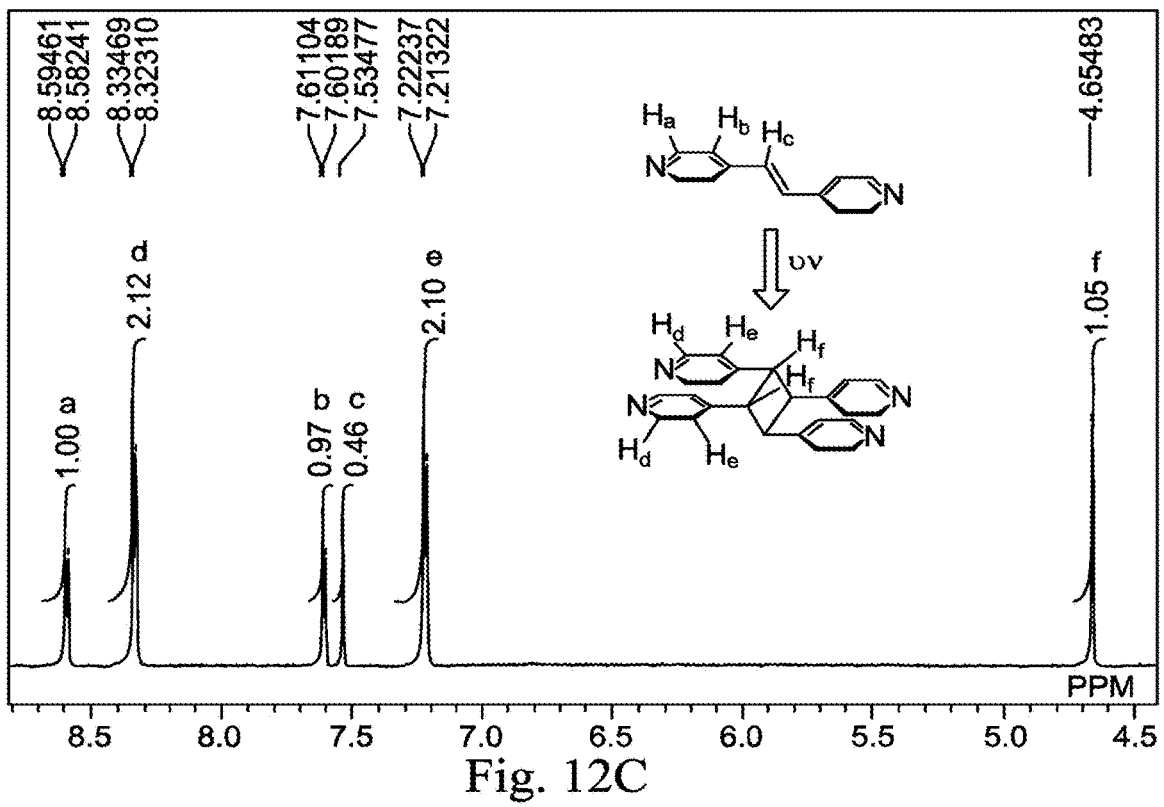
FIG. 12C shows an ¹H-NMR spectrum in DMSO-d₆ of compound (4) crystals after 50 hours of UV irradiation (DMSO-d₆)
Figure 13A:
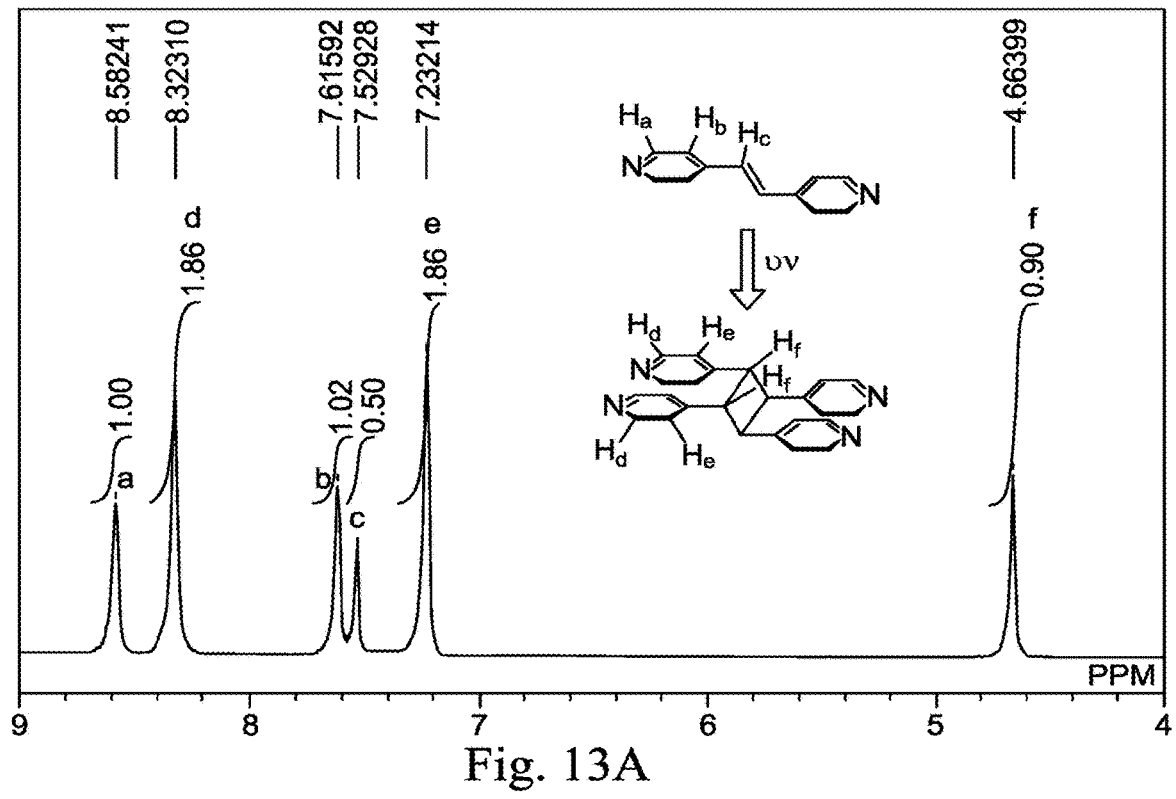
FIG. 13A shows an ¹H-NMR spectrum in DMSO-d₆ of a powder sample of ground crystals of compound (4) after 5 hours of UV irradiation.
Figure 13B:
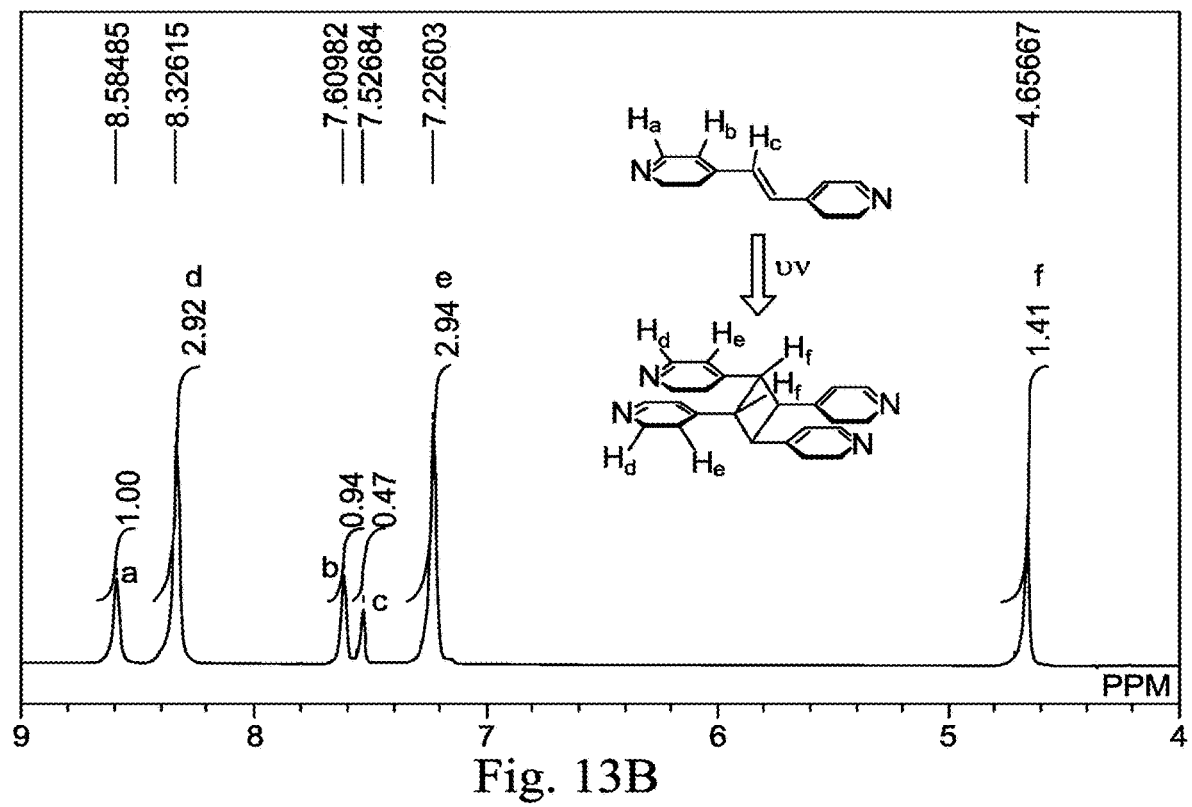
FIG. 13B shows an ¹H-NMR spectrum in DMSO-d₆ of a powder sample of ground crystals of compound (4) after 10 hours of UV irradiation.
Figure 13C:
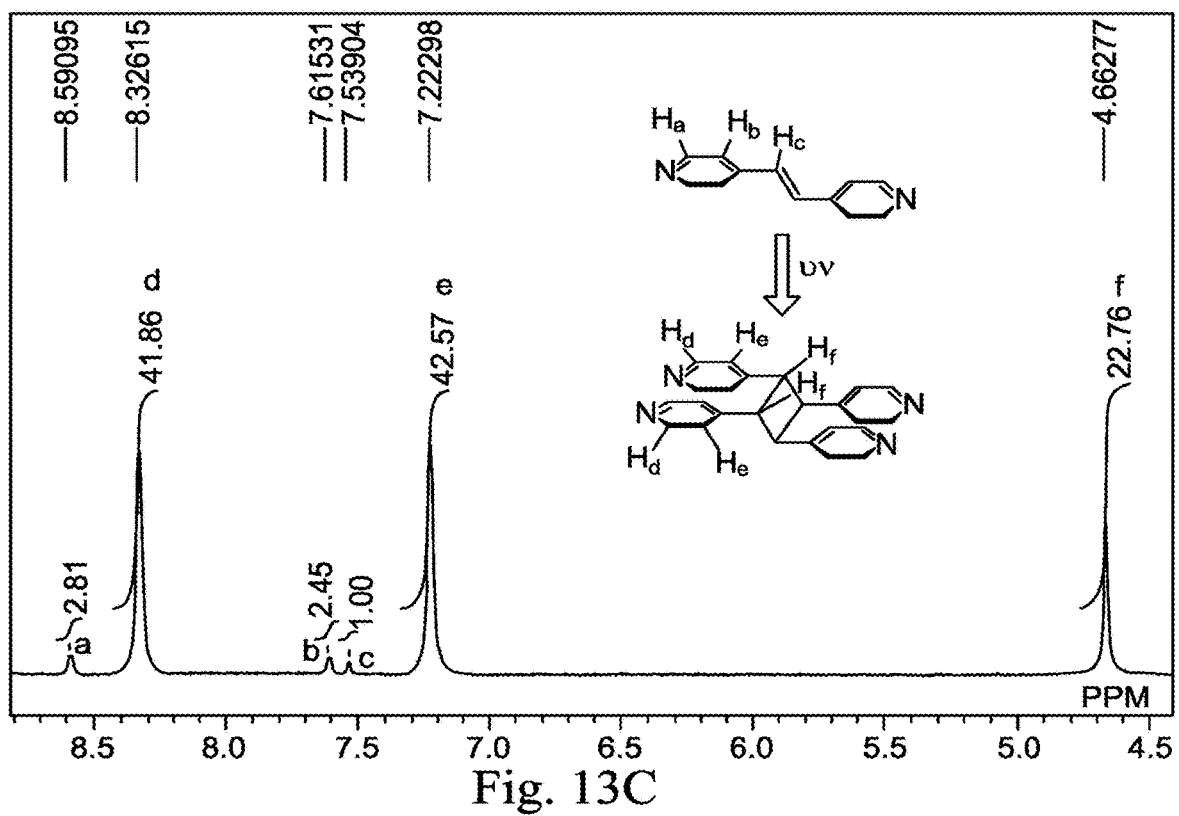
FIG. 13C shows an ¹H-NMR spectrum in DMSO-d₆ of a powder sample of ground crystals of compound (4) after 20 hours of UV irradiation.
Figure 13D:
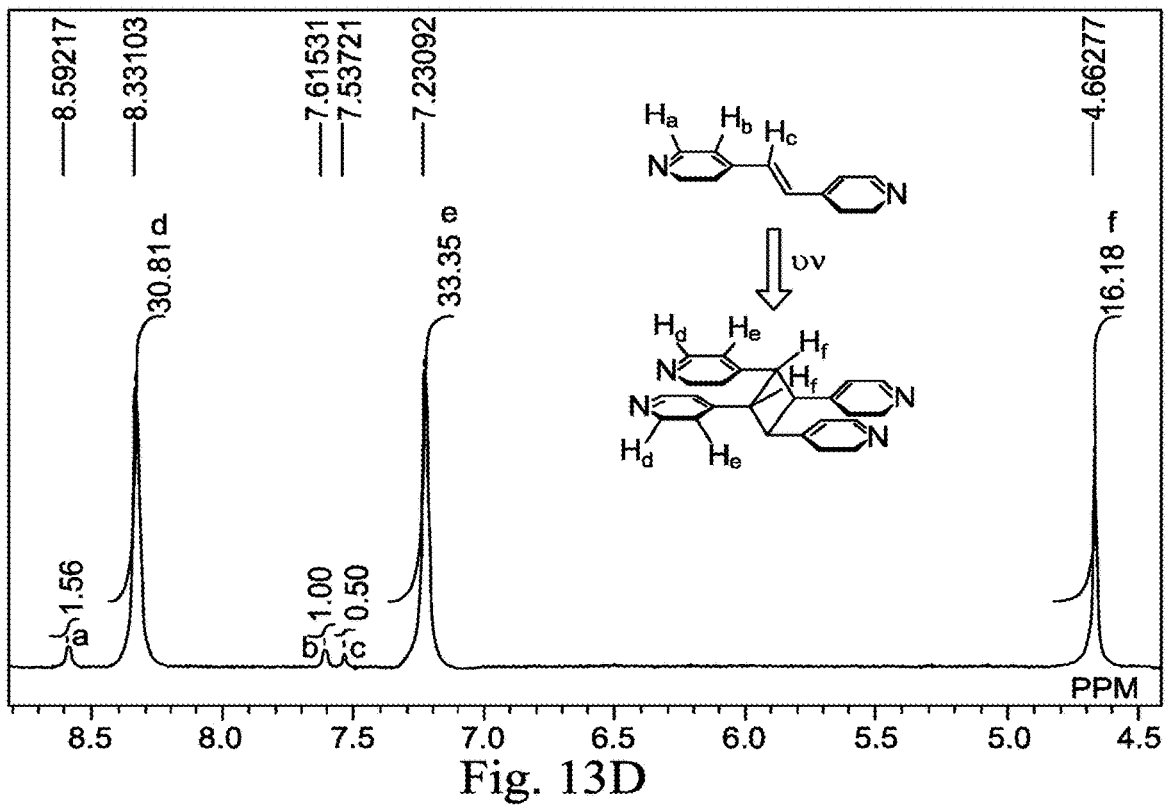
FIG. 13D shows an ¹H-NMR spectrum in DMSO-d₆ of a powder sample of ground crystals of compound (4) after 30 hours of UV irradiation.
Figure 13E:
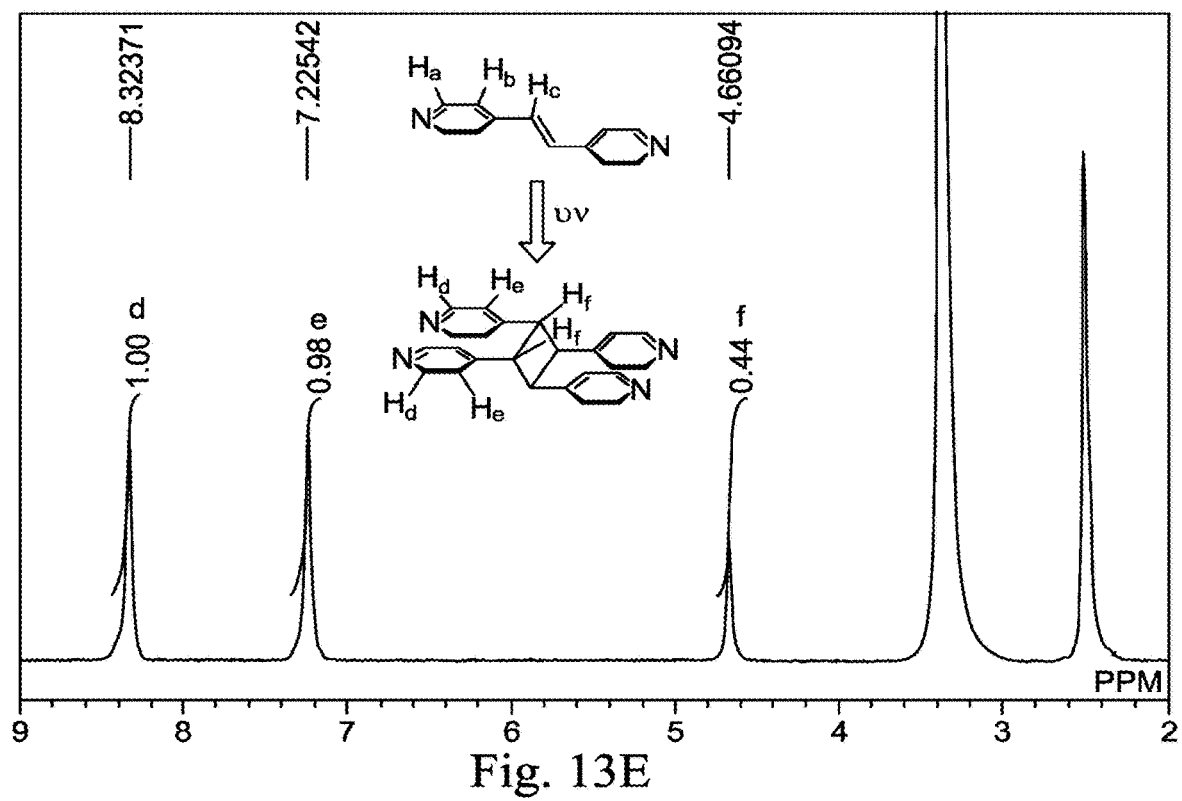
FIG. 13E shows an ¹H-NMR spectrum in DMSO-d₆ of a powder sample of ground crystals of compound (4) after 50 hours of UV irradiation.

The ¹H-NMR spectra in FIG. 12A to 12C show a decrease in intensity of a, b and c signals, which belong to photochemically unreacted bpe, and appearance of d, e and f signals, which belong to the product of the photochemical [2+2] cycloaddition, rctt-tpcb.

The percent conversion of bpe to rctt-tpcb within the compound (4) MOF was calculated in an analogous manner to above for the ¹H-NMR spectra in FIG. 12A to 12C, indicating about 40% at 5 hours, 62% at 20 hours, and 67% at 50 hours of UV irradiation. The maximum percent conversion was found to be 67% after 50 hours of UV irradiation of compound (4), as seen in FIG. 12C.

Grinding-Assisted Photodimerization

Based on the reported lattice structure in FIG. 11A, the maximum possible percent conversion was believed to be incapable of exceeding 67%. The use of mechanical forces, such as grinding, have been reported for different systems to force partially photodimerizing systems to increase their conversions, even to 100%, for example, in *Chem. Eur. J.* 2008, 14(17), 5329-5334. However, such techniques have never been reported for ladder-like structures.

Given this unpredictability, the crystals of the MOF of compound (4) were manually grinded for 10 minutes to a fine powder and its photoreactivity was explored for possible effects. The ground samples of the compound (4) MOF were UV irradiated for 5, 10, 20, 30, and 50 hours as above, then ¹H-NMR spectra were recorded and percent conversions were calculated for each spectrum. FIG. 13A to 13E show ¹H-NMR spectra of UV irradiated ground samples of compound (4) for 5, 10, 15, 30 and 50 hours, and the peak integrals.

The percent conversion of bpe to rctt-tpcb within the MOF of UV irradiated ground samples of compound (4) was calculated by integrating the relative peaks areas for both bpe and rctt-tpcb in the ¹H-NMR spectra obtained. Table 3 summarizes the percent conversion of bpe to rctt-tpcb in each UV irradiated sample for both crystals and powder samples of compound (4).

TABLE 3

Exposure time and percent (%) conversion for single crystals and ground samples of compound (4).

| Nature of the sample | Time of exposure, h | rctt isomer, % | Unreacted bpe, % | Bpe peaks total area | rctt isomer peaks total area | Total area of both |
|---|---|---|---|---|---|---|
| Single Crystal | 0 | 0 | 100 | 6 | 0 | 6 |
| | 5 | 39.16 | 60.84 | 2.47 | 1.59 | 4.06 |
| | 20 | 62.38 | 37.62 | 2.43 | 4.03 | 6.46 |
| | 50 | 67.29 | 32.71 | 2.43 | 5 | 7.43 |
| 10 min. Grinding | 0 | 0.0 | 100.0 | 6 | 0 | 6 |
| | 5 | 64.7 | 35.3 | 2.52 | 4.62 | 7.14 |
| | 10 | 75.1 | 24.9 | 2.41 | 7.27 | 9.68 |
| | 20 | 94.4 | 5.5 | 6.26 | 107.19 | 113.45 |
| | 30 | 97.0 | 3.0 | 2.5 | 80.34 | 82.84 |
| | 50 | 100.0 | 0.0 | 0 | 2.42 | 2.42 |

Figure 14:
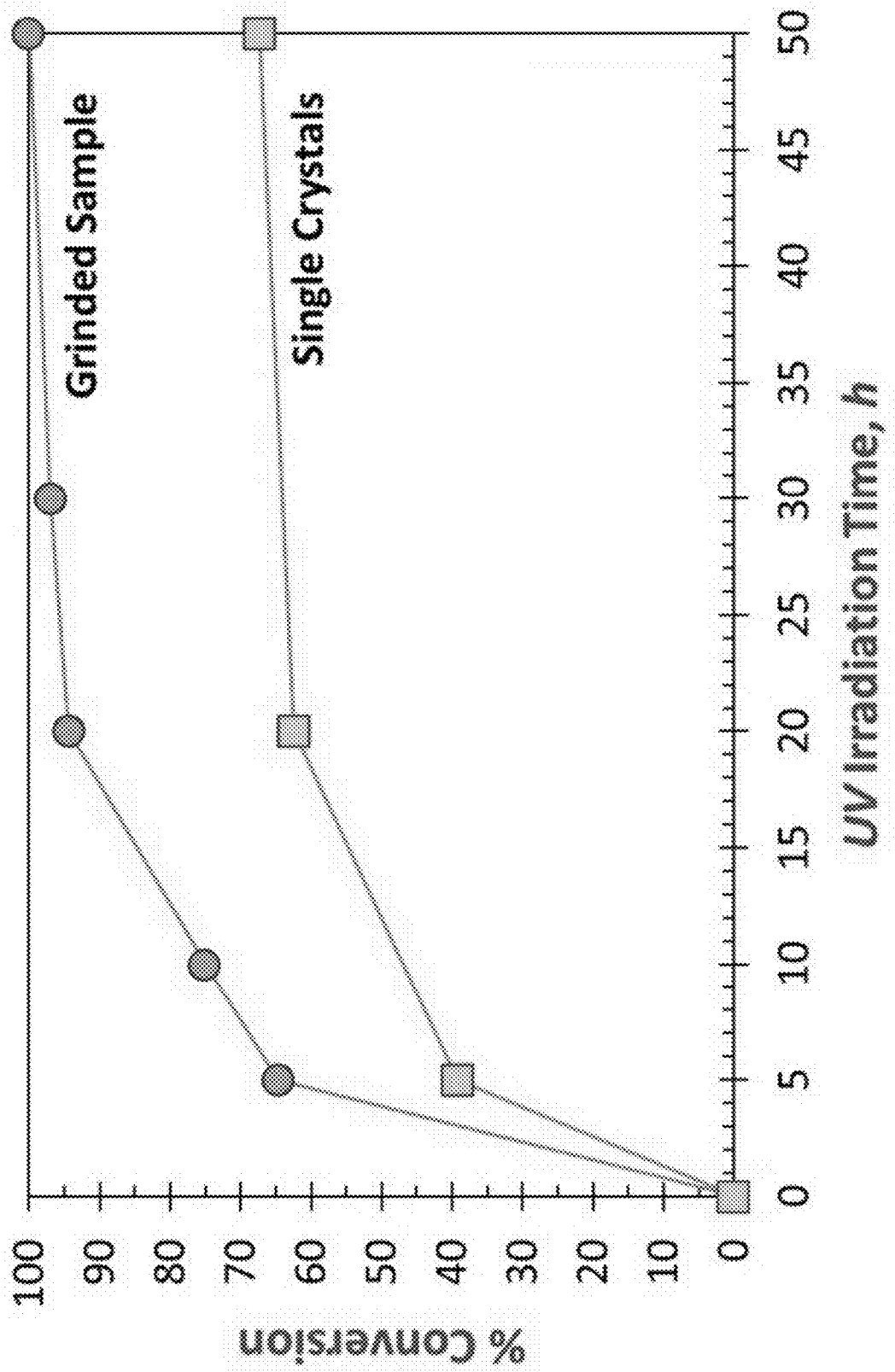
FIG. 14 shows a plot of the percent conversion of bpe to rctt-tpcb in the MOF of compound (4) over time for grinded (above) and crystalline (below) samples.

The ¹H-NMR spectra obtained for compound (4) in FIG. 13A to 13E show that the crystal grinding has boosted the percent conversion of the bpe ligands to rctt-tpcb within the MOF dramatically. After only 5 hours of UV irradiation, the compound (4) system achieved almost 67% conversion, which is the maximum conversion of the crystals samples. Furthermore, the maximum percent conversion obtained was found to be 100% after 50 hours of UV irradiation. FIG. 14 shows a comparison between the photochemical behavior between the crystals (below) and ground (above) samples.

Figure 11B:
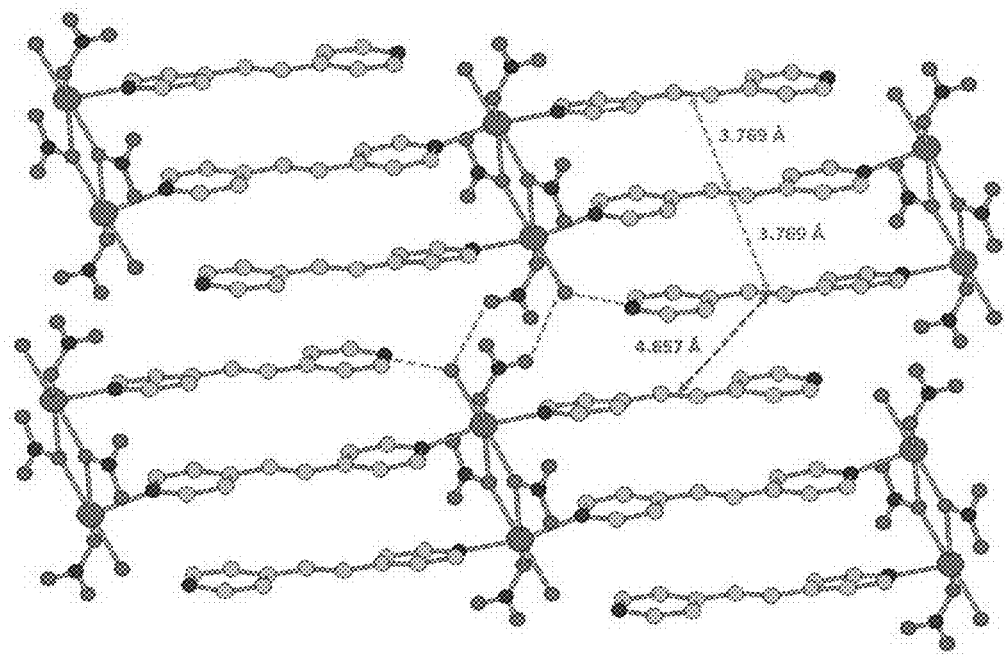
FIG. 11B shows crystal structure packing of compound (4)
Figure 15:
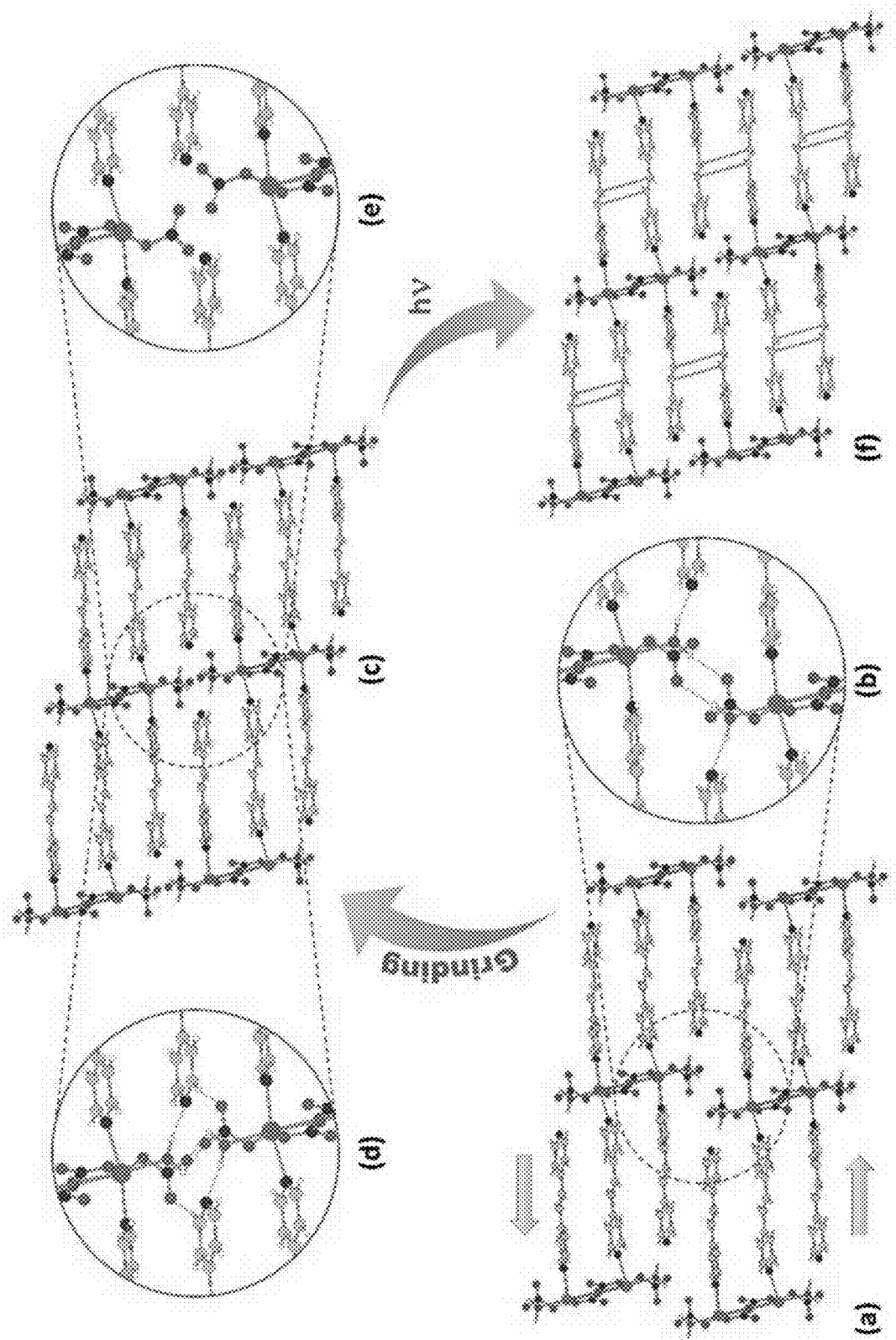
FIG. 15 shows a representation of proposed behavior of the MOF of compound (4) due to grinding its dinuclear triple-strand-like 1D photoreactive ladder structure based on a cadmium analog.

This observed photochemical behavior of compound (4) may be explained by large internal molecular movement within the lattice structure of the MOF upon grinding. The proposed mechanism for this is mechanical alignment is shown in FIG. 15. The mechanism may be rationalized based on a crystal structural analysis of compound (4). The crystal structure of compound (4) contains adjacent, slightly misaligned ladder structures held together by hydrogen bonding. Each ladder structure contains sets of three aligned bpe, held by strong coordination bonds through four Cd(II) centers, two from each side, reinforced by π-π interactions between the aligned pyridyl rings, as shown in FIG. 11B.

The distance between each aligned pair of C═C double bonds in the MOF of compound (4) is 3.77 Å, which is well within the theoretical range in which cyclobutane can be formed photochemically. Of the three bpe in each crystal set, only two can theoretically undergo photodimerization, which may explain the 67% conversion for single crystal samples of compound (4). The distance between a pair of C═C double bonds from adjacent ladder structures is 4.66 Å. Thus, a pair of C═C double bonds from adjacent ladder structures within compound (4) cannot undergo photochemical reaction to form cyclobutane according to Schmidt's postulate.

The mechanical forces of grinding may have caused slightly misaligned ladder structures within compound (4) to move in opposite directions (portion "a" of FIG. 15) and align (portion "c" of FIG. 15). Thus, a structure with infinite bpe ligands, parallel and perfectly aligned, may be produced by grinding-induced internal molecular movements (portion "c" of FIG. 15). The distance between C═C double bonds from two adjacent ladder structures can ostensibly be reduced to less than 4.2 Å, which should allow photochemical [2+2] cycloaddition to occur between the two adjacent ladder structures. Therefore, complete photodimerization (100% conversion) of all bpe ligands within compound (4) may be achieved (portion "f" of FIG. 15) as reported for ladder MOFs of different composition in the literature.

The driving force for such internal molecular movements can be the formation of stronger molecular interactions. Initially, each of these ladder structures contain repeating patterns of three aligned bpe, which exhibit π-π stacking to produce four π-π interactions in total for the three aligned bpe, i.e., one between each two pyridyl rings, as seen in portion "a" of FIG. 15. Moreover, each dual ladder structure may be held together by two hydrogen bonds, as seen in portion "b" of FIG. 15. The first hydrogen bond would be between a hydrogen atom from a coordinated water molecule and an oxygen atom from a coordinated nitrate of a neighboring ladder structure, while the second one is the other way around.

When crystals are grinded, adjacent ladder structures may slide to opposite directions and possibly align six bpe ligands, as shown in portion "c" of FIG. 15. Four new π-π interactions would then occur between the two-adjacent ladder structures, which is 20% increase in π-π interactions. These new interactions may be at least partially responsible for the internal molecular movement and lattice repacking. Newly formed packing may have a higher stability due to these interactions. Stability may also be gained by interactions between terminal water and nitrate ligands of each cadmium center. At least two possible scenarios may govern. The first scenario involves hydrogen bonding changing upon the realignment of adjacent ladder structures, with terminal water ligand hydrogens forming H-bonds with two oxygens of the terminal nitrate ligands from adjacent ladder structure, seen in portion "d" of FIG. 15. The first scenario may require the rotation of the coordination bond of terminal water to change its direction toward the metal center of an adjacent ladder. The second possible scenario is the loss of a water molecule from the coordination sphere, as shown in portion "e" of FIG. 15.

Certain (different) MOF structures were reportedly unaffected in photoreactivity by the loss of water, though the unpredictability of reactivity and/or properties in MOFs does not allow these results to be presumed for inventive MOFs. Thus, to gain more information on the driving impetus for grinding-based realignment, thermogravimetric analysis (TGA) may provide information on coordinated and free water molecules in lattice structures, which each have characteristic weight-loss temperature in coordinated or free form.

Figure 16A:
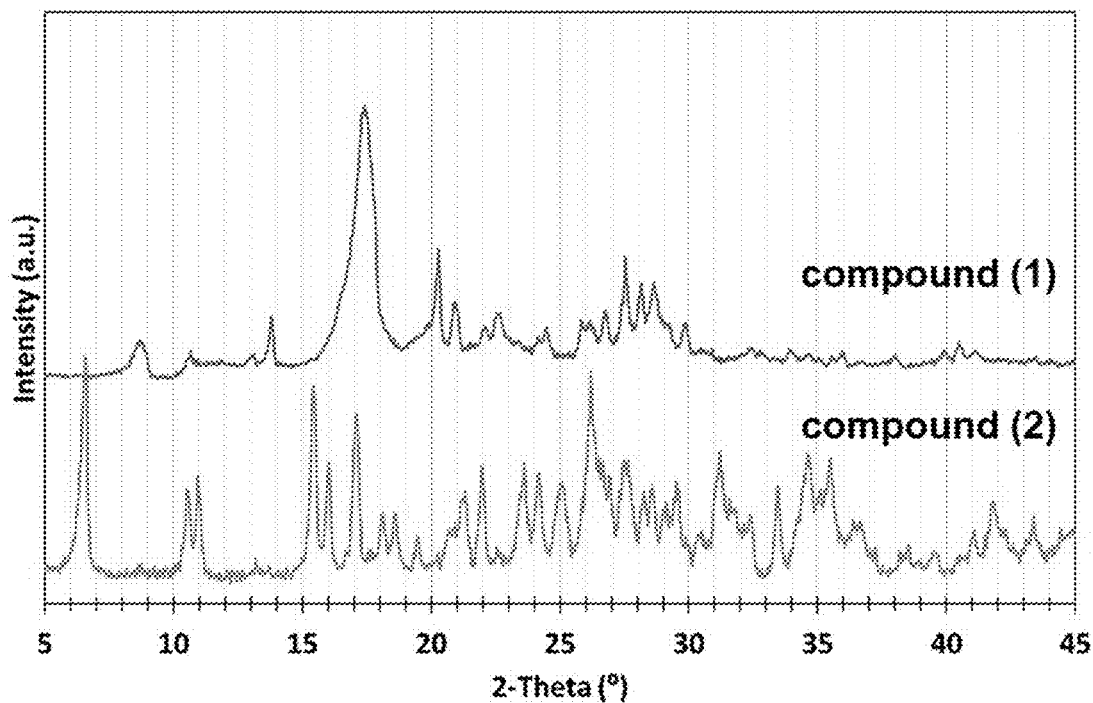
FIG. 16A shows PXRD patterns of compounds (1) and (2)
Figure 16B:
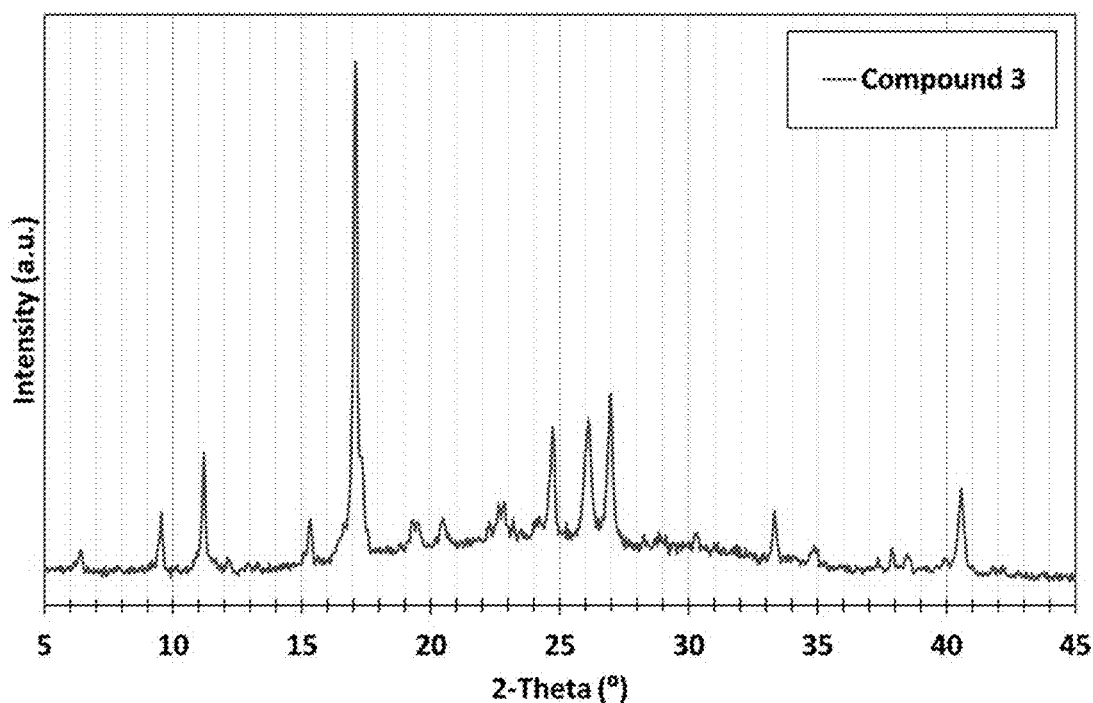
FIG. 16B shows a PXRD pattern of compound (3)

Powder x-ray diffraction (PXRD) can provide information phase identification and structure of crystalline materials. The collected patterns from compounds (1) to (3) provide structural information and synthetic confirmation of compound (4). FIGS. 16A and 16B show the PXRD patterns of compounds (1) to (3).

Although the same stoichiometric ratios of the metal ions and ligands were used during the synthesis process of compounds (1) and (2), FIG. 16A verifies that compounds (1) and (2) have different structures. Further structural information can also be deduced from collected PXRD patterns. The characteristic peak close to 5° (2θ) commonly appears for porous materials. Furthermore, the two peaks around 10° (2θ) usually appear for extended structures, such as MOFs. The presence of these three peaks for the PXRD patterns of compounds (2) and (3) in FIGS. 16A and 16B may indicate that these compounds are extended and/or repetitive structures, i.e., MOFs, as well as porous materials. However, dimensionality cannot be deduced from these PXRD patterns. The PXRD pattern for compound (1) shows only the presence of 10° (2θ) peaks, suggesting that compound (1) may not be porous, but may have an extended structure.

The possibility that compounds (1) or (2) might be isostructural to a known Mn(II)-based broken ladder-like 2D sheet MOF, $[Mn_2(\mu\text{-ox})_2(\mu\text{-bpe})(bpe)_2]_n$, is disproven by the PXRD patterns obtained for compounds (1) and (2) in FIG. 16A, showing that compounds (1) and (2) are not isostructural to $[Mn_2(\mu\text{-ox})_2(\mu\text{-bpe})(bpe)_2]_n$. The presence of a 5° (2θ) peak in the PXRD pattern of compound (2) indicates porosity, while the reported Mn(II) MOF is porous. Therefore, between compounds (1) or (2), only compound (1) may be analogous to the Mn(II) MOF. However, the PXRD pattern of compound (1) in FIG. 16A does not match the calculated powder pattern of $[Mn_2(\mu\text{-ox})_2(\mu\text{-bpe})(bpe)_2]_n$.

Figure 17A:
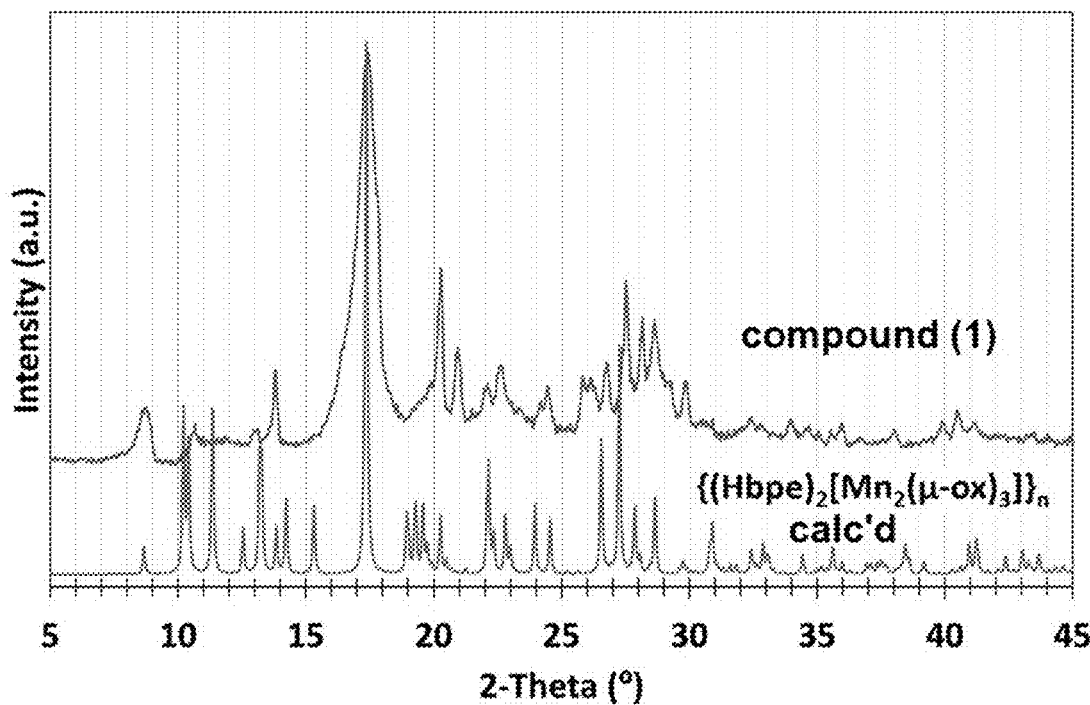
FIG. 17A shows an experimentally obtained PXRD pattern of exemplary compound (1), $\{(Hbpe)_2[Zn_2(ox)_3]\}_n \cdot (H_2O) \cdot 2.2(DMF)$, and a calculated PXRD pattern of $\{(Hbpe)_2[Mn_2(\mu\text{-}ox)_3]\}_n$.
Figure 17B:
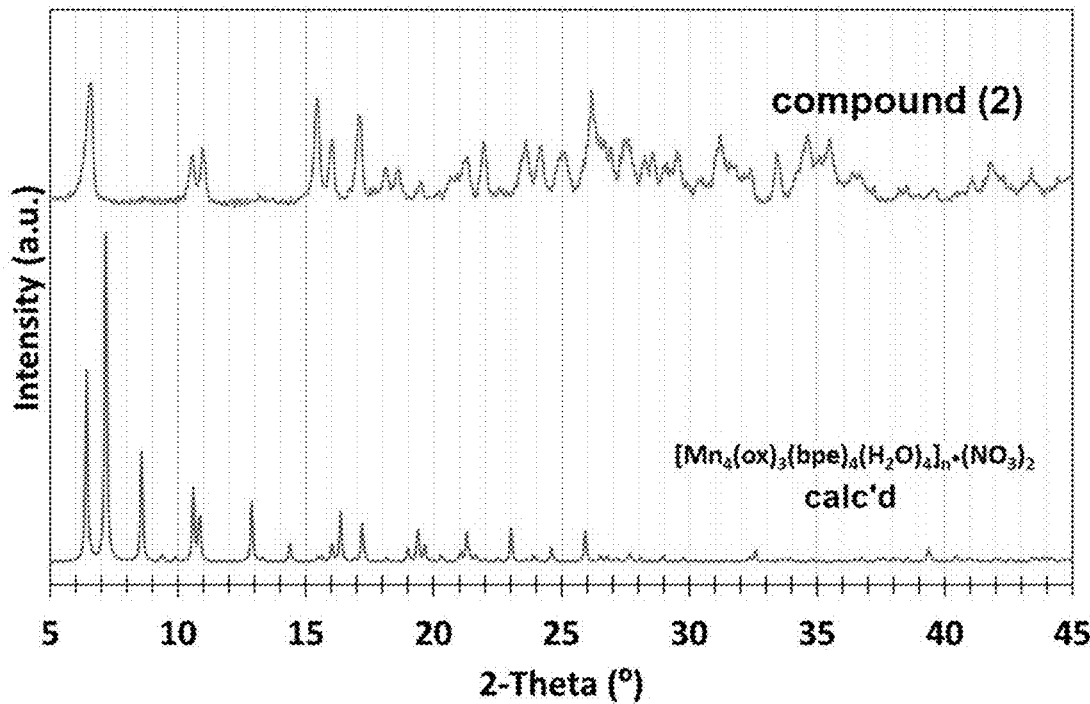
FIG. 17B shows an experimentally obtained PXRD pattern of exemplary compound (2), $[Pb_4(ox)_3(bpe)_4(H_2O)_4]_n \cdot (NO_3)_2$, and a calculated PXRD pattern of $[Mn_4(ox)_3 (bpe)_4(H_2O)_4]_n$.
Figure 17C:
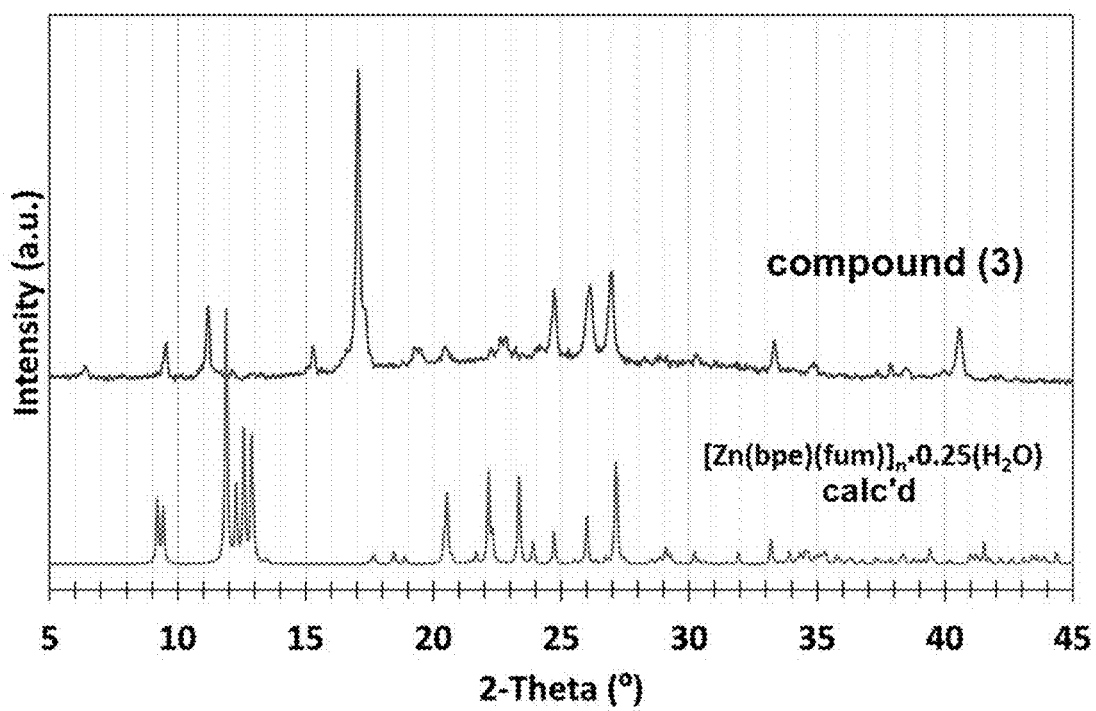
FIG. 17C shows an experimentally obtained PXRD pattern of exemplary compound (3), $[Pb(bpe)(fum)]_n \cdot 0.25 (H_2O)$, and a calculated PXRD pattern of $[Zn(bpe)(fum)]_n$.
Figure 17D:
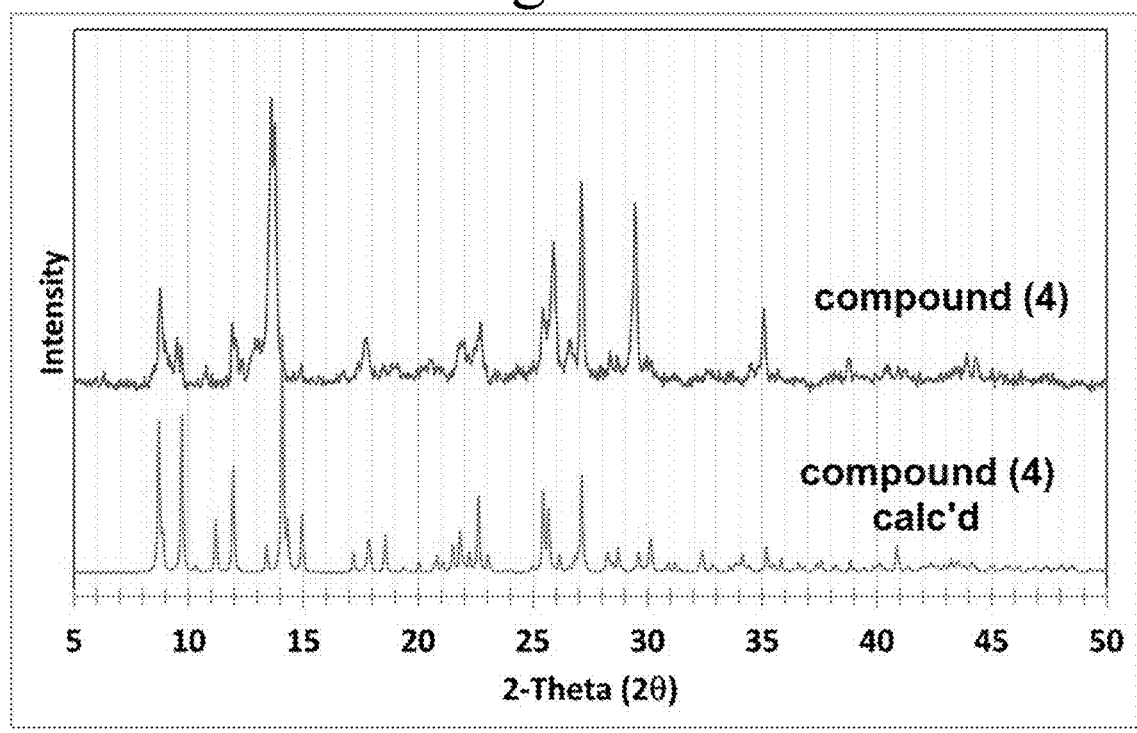
FIG. 17D shows an experimentally obtained PXRD pattern of exemplary compound (4) and a calculated PXRD pattern.

The PXRD patterns obtained for compounds (1) to (3) are compared to those of known MOFs in the art that contain the same ligands in FIG. 17A to 17C. The comparable patterns in FIG. 17A to 17C may indicate some lattice structure correlation, but the difference in peak intensity between experimental PXRD patterns and calculated PXRD patterns is due at least in part to the presence of different metal ions in compounds (1) to (3) from the calculated analogs. Thus, compounds (1) to (3) might have similar structures the analogous MOFs, thought the dissimilarities indicate differences in the orientations and contents of the crystals in the powder samples. The experimental and calculated PXRD pattern of compound (4) is shown in FIG. 17D.

Compound (1)

Figure 18:
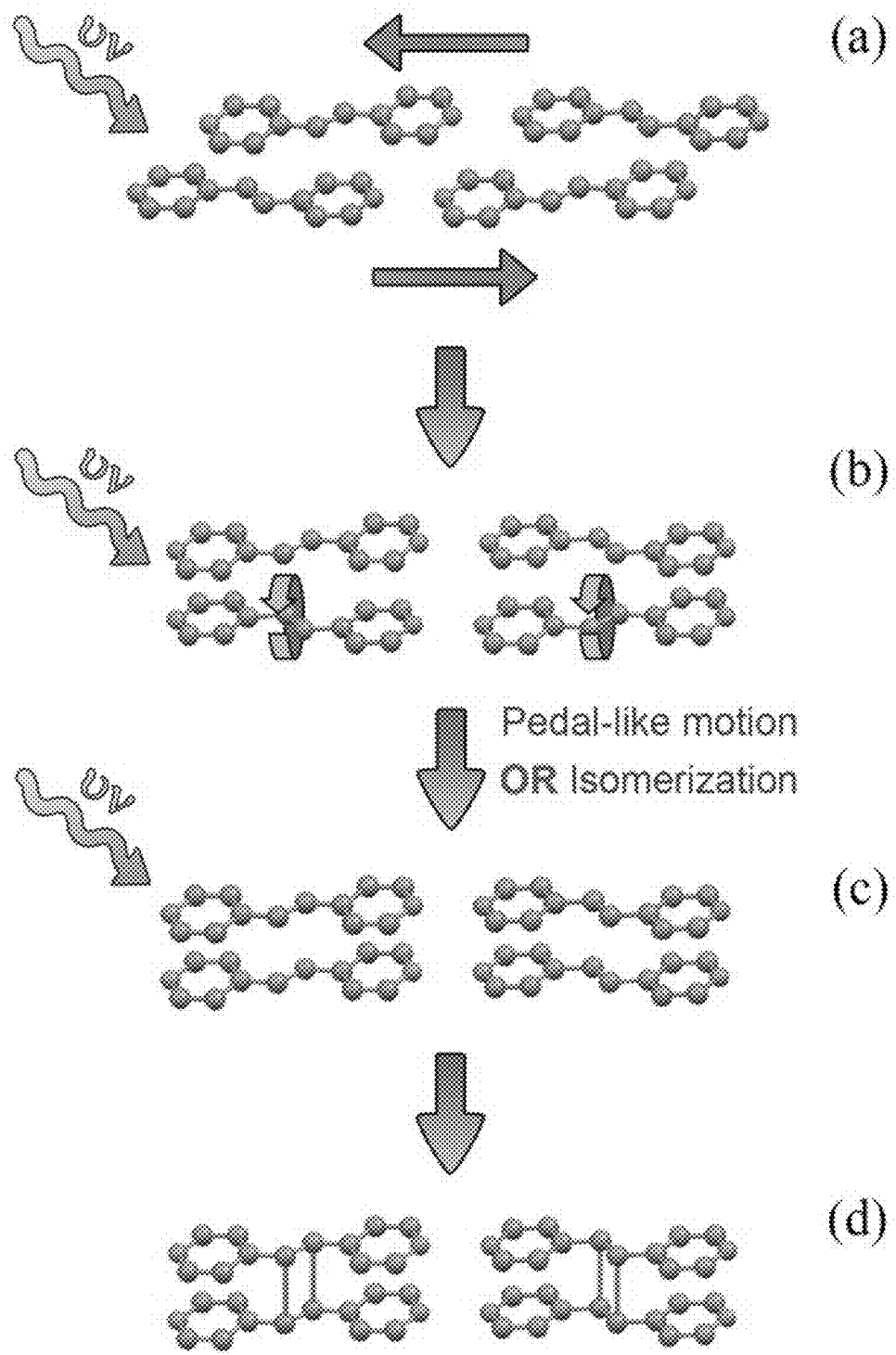
FIG. 18 shows theoretical possibilities for free bpe molecules to undergo large internal molecular motion to meet the right conditions for the photochemical [2+2]cycloaddition in compound (1)

The PXRD pattern of compound (1) was postulated to have some similarities to the calculated PXRD pattern of $\{(Hbpe)_2[Mn_2(\mu\text{-ox})_3]\}_n$. $\{(Hbpe)_2[Mn_2(\mu\text{-ox})_3]\}_n$ includes alternating layers of free cationic bpe molecules and $[Mn_2(\mu\text{-ox})_3]_n^{2-}$ 2D sheets. The $[Mn_2(\mu\text{-ox})_3]_n^{2-}$ 2D sheets have a honeycomb topology, while the free cationic bpe molecules are held together by hydrogen bonding and π-π interactions. The lattice structure of compound (1) relative to the calculated PXRD pattern, indicates that the bpe molecules are not consistent with Schmidt topochemical criteria for photochemical [2+2] cycloadditions. The bpe ligands in compound (1) are not perfectly aligned and the distance between each pair of olefinic C=C double bonds is 4.769 Å, which is beyond the theoretical threshold for photochemical [2+2]cycloadditions to occur. In addition, the olefinic C=C double bonds in compound (1) are not aligned in parallel but instead criss-cross. Nevertheless, compound (1) has been shown to be photochemically active and capable of photochemical [2+2] cycloaddition, indicating that compound (1)'s bpe may either undergo sufficient internal molecular motion due to UV irradiation to meet the right topochemical conditions for the photochemical reaction, as presented in FIG. 18, or the actual alignment in compound (1) differs from the alignment of the $\{(Hbpe)_2[Mn_2(\mu\text{-ox})_3]\}_n$. FIG. 18 shows a proposed mechanism for bpe molecules in compound (1) to undergo photochemical [2+2] cycloaddition if the bpe alignment assumed to be like that in Mn-MOF. Because the bpe molecules are free, they can move inside the lattice structure if enough energy is provided and if void space is available. UV irradiation may provide sufficient energy for such behavior.

The proposed mechanism in FIG. 18 for photochemically activating intra-lattice ligand movements includes several steps. In a first step, bpe molecules slide in opposite directions along the x-axis and align their pyridyl rings perfectly, as seen in portion "a" of FIG. 18. The first step may occur due to increased π-π interactions between pyridyl rings and olefinic C=C double bonds contributing to a thermodynamically more stable structure. In a second step, bpe molecules undergo trans-trains isomerization or pedal-like motion to form parallel alignment of the olefinic C=C double bonds, as seen in portion "b" of FIG. 18. The driving force of the second step may be the initiation of photochemical process that causes the rotation of HOMO and LUMO orbitals of the two alkene olefinic C=C double bonds to achieve preferred symmetry through suprafacial orientation. In a last step of the mechanism, the photochemical [2+2] cycloaddition reaction occurs, forming a rctt-tpcb product, as seen in portion "c" and "d" of FIG. 18.

Compound (2)

The PXRD pattern of compound (2) was postulated to have some similarities to the calculated PXRD pattern of $[Mn_4(ox)_3(bpe)_4(H_2O)_4]_n \cdot (NO_3)_2$, a 3D framework with 1D pores. The lattice structure of $[Mn_4(ox)_3(bpe)_4(H_2O)_4]_n \cdot (NO_3)_2$ includes 2D sheets connected by bpe ligands to construct a cationic 3D network, $[Mn_4(ox)_3(bpe)_4(H_2O)_4]_n^{2+}$. Each repeating unit in $[Mn_4(ox)_3(bpe)_4(H_2O)_4]_n \cdot (NO_3)_2$ has four Mn(II) metal centers connected to each other through three oxalate ligands. The Mn(II) metal centers in $[Mn_4(ox)_3(bpe)_4(H_2O)_4]_n \cdot (NO_3)_2$ are hepta-coordinated in pentagonal bipyramidal geometry, with two bidentate oxalate ligands and one water molecule in equatorial orientations and two bpe ligands in axial positions. The repeating unit of $[Mn_4(ox)_3(bpe)_4(H_2O)_4]_n \cdot (NO_3)_2$ also has four bpe ligands, coordinated to axial positions in the four Mn(II) metal centers. The Mn(II) metal centers are connected through oxalate ligands to form 2D sheets, $[Mn_4(ox)_3(H_2O)_4]_n^{2+}$.

The 2D sheets in $[Mn_4(ox)_3(bpe)_4(H_2O)_4]_n \cdot (NO_3)_2$ contain hollow spaces formed by eight Mn(II) centers connected by eight oxalate ligands. Vacant channels are formed by the alignment of multiple sheets within the lattice structure of $[Mn_4(ox)_3(bpe)_4(H_2O)_4]_n \cdot (NO_3)_2$ to construct the 1D pores within the MOF. Furthermore, four coordinated water molecules are directed inwards these hallow spaces, which renders the MOF hydrophilic.

Since compound (2) is postulated to correlate to the lattice structure of $[Mn_4(ox)_3(bpe)_4(H_2O)_4]_n \cdot (NO_3)_2$, the most important attribute of this lattice structure for photochemical [2+2] cycloaddition reaction is bpe alignment. The bpe ligands are coordinated from both sides to two Mn(II) metal centers in axial position from two different 2D sheets and pillaring the layers of these sheets to form 3D framework. Each (two) bpe ligands coordinated to adjacent Mn(II) centers are aligned to each other with very slight misalignment in angle. This small misalignment can be overcome by rotation of the coordination bonds Mn—N. Therefore, the misalignment should not prevent photochemical [2+2] cycloaddition from occurring. The distance between the centers of two olefinic C=C double bonds from aligned bpe ligands was measured to be 3.995 Å, which is within the theorized range in which the photochemical [2+2] cycloaddition reaction can occur.

Compound (3)

The PXRD pattern of compound (3) was postulated to have some similarities to the calculated PXRD pattern of $[Zn(bpe)(fum)]_n \cdot 0.25(H_2O)$. $[Zn(bpe)(fum)]_n \cdot 0.25(H_2O)$ is an interpenetrated 3D network having 2D sheets pillared by bpe ligands that exhibit α-Po topology. The Zn(II) metal centers of $[Zn(bpe)(fum)]_n \cdot 0.25(H_2O)$ are penta-coordinated in a trigonal bipyramidal geometry. Each metal center in $[Zn(bpe)(fum)]_n \cdot 0.25(H_2O)$ is coordinated to two bpe in axial orientations and three fumarate ligands in equatorial orientations. However, the 2D sheets of $[Zn(bpe)(fum)]_n \cdot 0.25(H_2O)$ have a different topology from $[Mn_4(ox)_3(bpe)_4(H_2O)_4]_n \cdot (NO_3)_2$, above, and the connectivity of the sheets of $[Zn(bpe)(fum)]_n \cdot 0.25(H_2O)$ through bpe is parallel/anti-parallel bpe pairs connected through orthogonal 1D fumarate chains.

The bpe ligands in $[Zn(bpe)(fum)]0.25(H_2O)$ are coordinated through both nitrogen atoms to two Zn(II) centers from two different layers in the lattice structure. Each of the two bpe ligands in $[Zn(bpe)(fum)]_n \cdot 0.25(H_2O)$ are aligned to each other through coordination to adjacent Zn(II) metal centers. Every pair of olefinic C=C double bonds in the adjacent bpe ligands within $[Zn(bpe(fum)]0.25(H_2O)$ are parallelly aligned and have a distance of 3.992 Å, which should allow the photochemical [2+2] cycloaddition to occur. The pair-wise distribution of bpe ligands within the $[Zn(bpe)(fum)]_n \cdot 0.25(H_2O)$ lattice structure may explain why 100% conversion of bpe ligands to the rctt-tpcb product by photochemical [2+2]cycloaddition, consistent with theory on similar lattice structure of compound (3) to the $[Zn(bpe)fum)]_n \cdot 0.25(H_2O)$ MOF based on its analogous PXRD pattern.

Compound (4)

The PXRD pattern obtained for compound (4) was postulated to have some similarities to the calculated PXRD pattern of $[Cd(bpe)_{1.5}(NO_3)_2(H_2O)]_n$, having a dinuclear triple-strand-like 1D ladder photoreactive cadmium-based MOF, as seen in FIG. 17D.

Thermogravimetric Analysis (TGA) of Compounds (1) to (4)

Figure 19A:
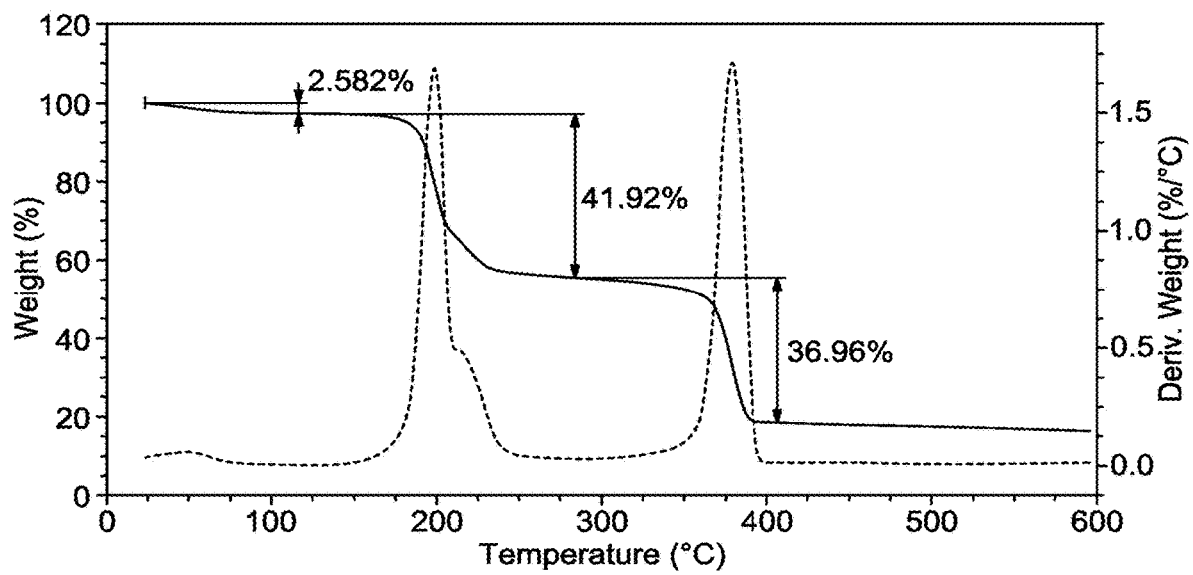
FIG. 19A shows a thermogravimetric analysis (TGA) plot of compound (1)
Figure 19B:
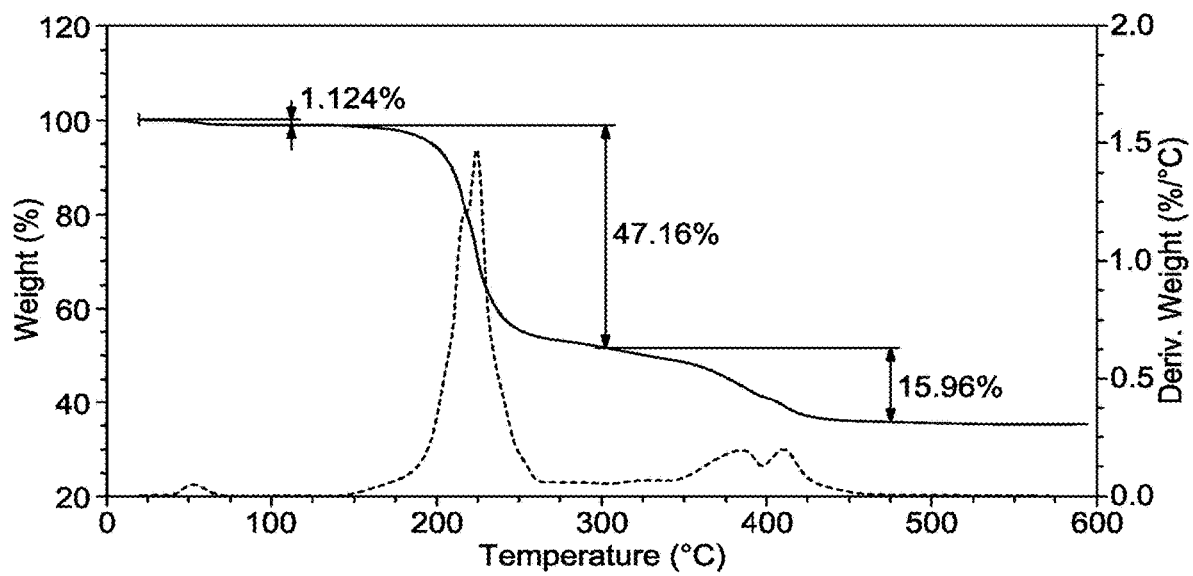
FIG. 19B shows a TGA plot of compound (2)
Figure 19C:
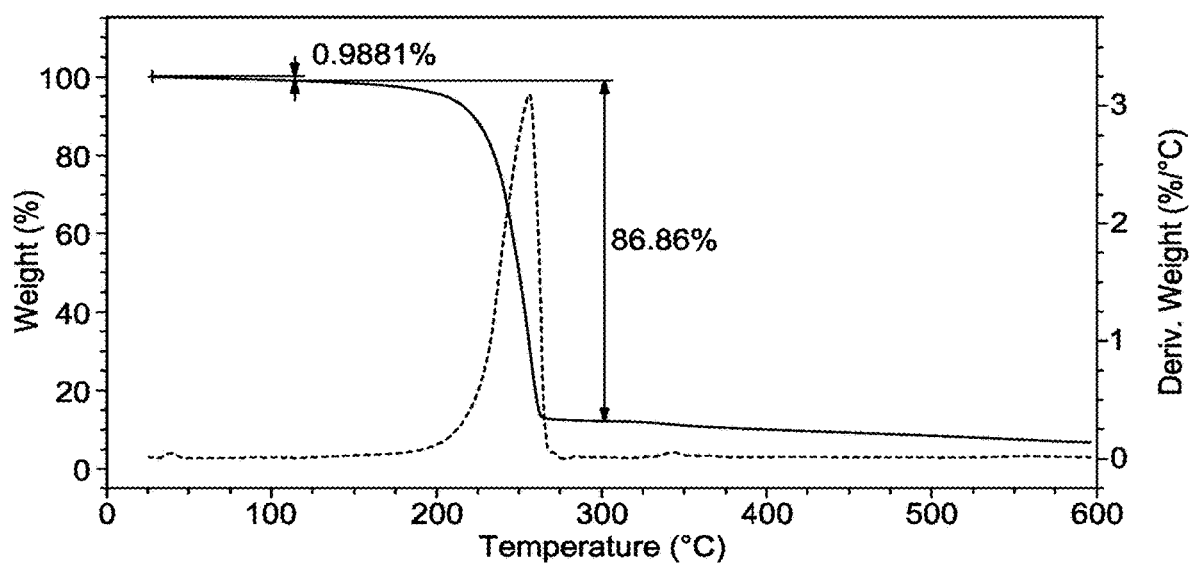
FIG. 19C shows a TGA plot of compound (3)
Figure 20A:
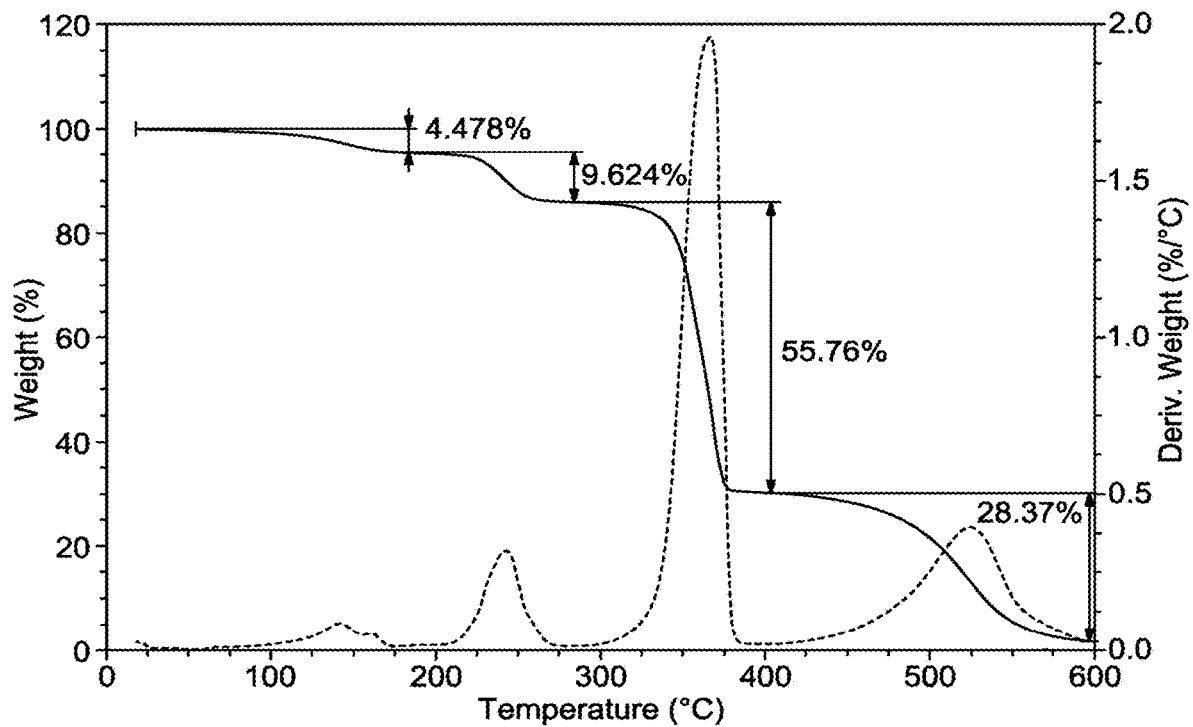
FIG. 20A shows a TGA plot of a single crystal sample of compound (4) before UV irradiation.
Figure 20B:
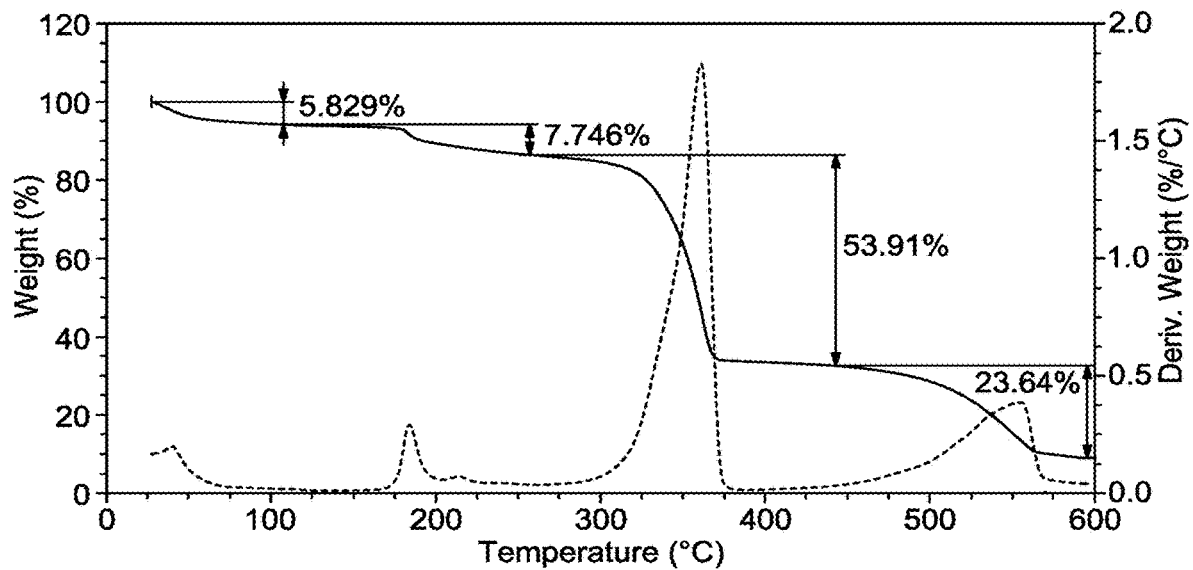
FIG. 20B shows a TGA of a 10-minute ground crystal sample of compound (4) before UV irradiation.
Figure 20C:
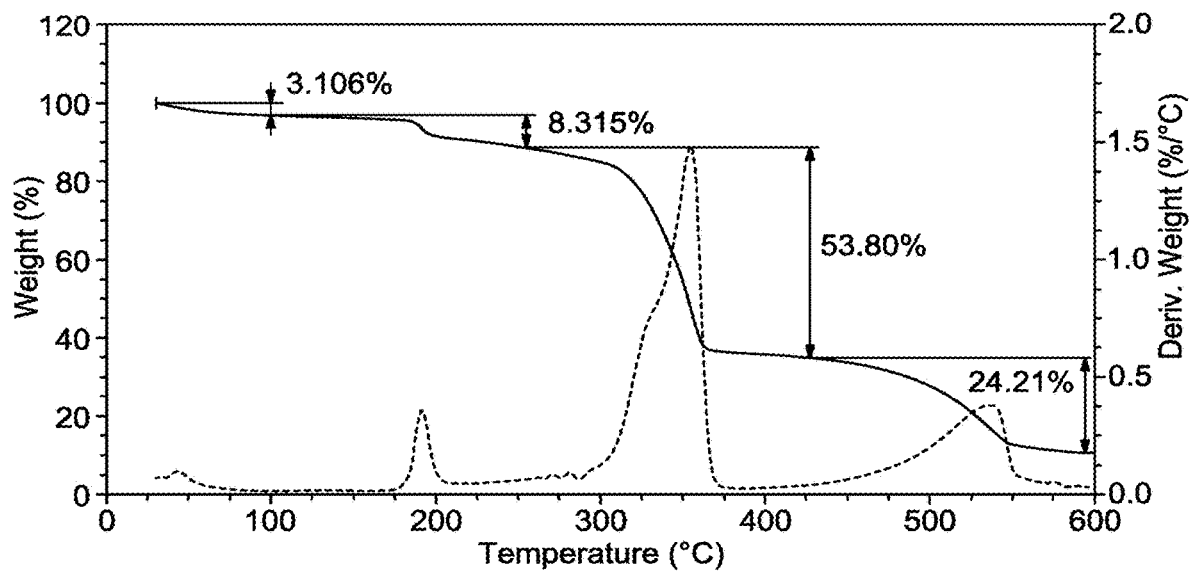
FIG. 20C shows a TGA of a 20-minute ground crystal sample of compound (4) before UV irradiation.
Figure 20D:
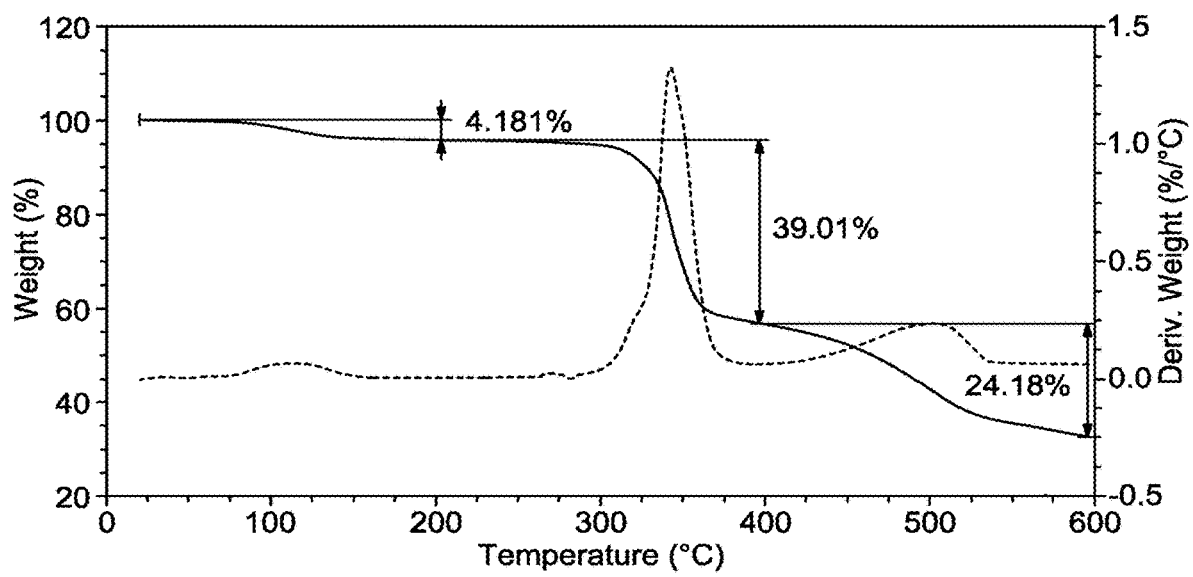
FIG. 20D shows a TGA plot of a single crystal sample of compound (4) after 50 hours of UV irradiation.
Figure 20E:
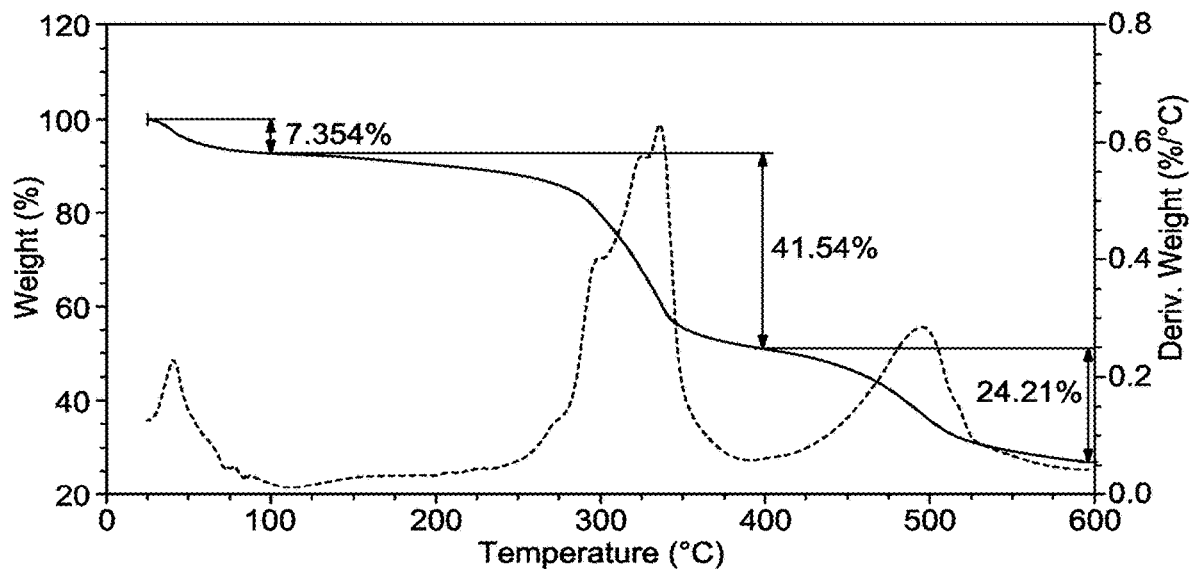
FIG. 20E shows a TGA of a 10-minute ground crystal sample of compound (4) after 50 hours of UV irradiation.
Figure 20F:
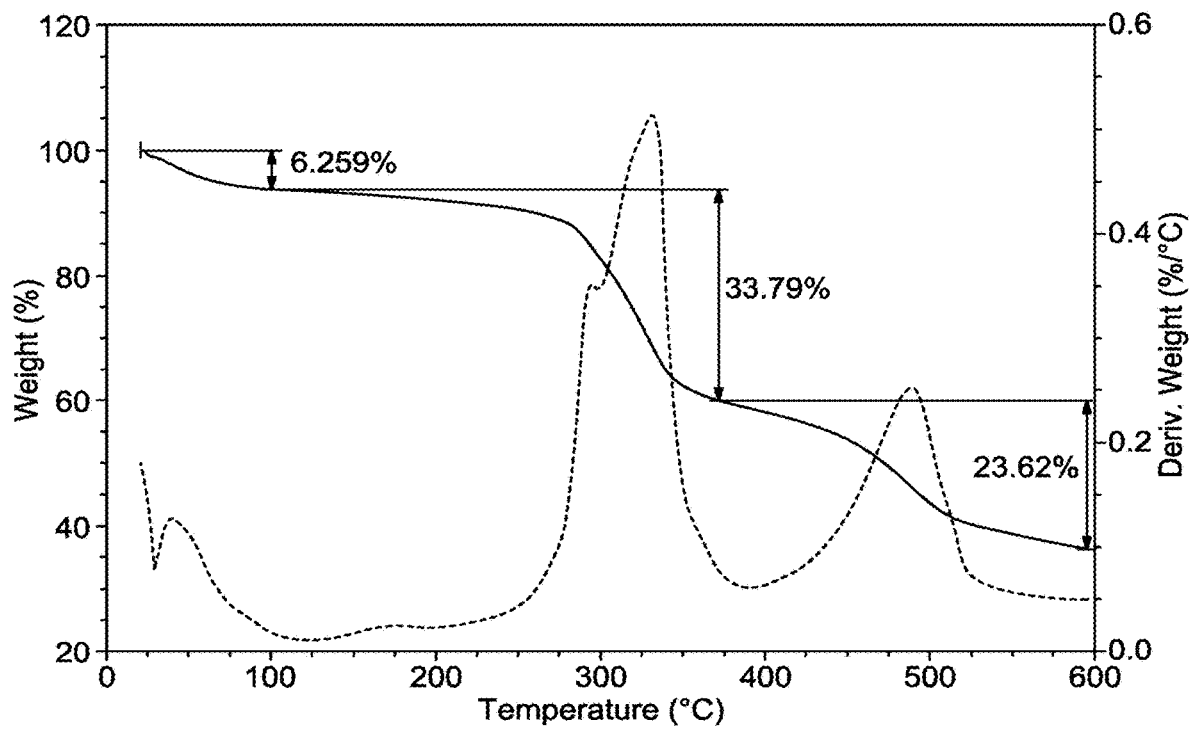
FIG. 20F shows a TGA of a 20-minute ground crystal sample of compound (4) after 50 hours of UV irradiation.

TGA technique was used on compounds (1) to (3) to confirm obtained structural information about their respective MOFs. FIG. 19A to 19C show TGA thermograms obtained for compounds (1) to (3).

The presence of two steps in the thermal decomposition for compound (1), seen in FIG. 19A, indicate the presence of two different types of bonded chemical species within the lattice structure. These chemical species are bpe, which decomposes in the first step, and oxalate, which decomposes in the second step due to the higher strength of the Zn—O bond. Furthermore, the 2.5% loss in weight % at around 100° C. corresponds to one water molecule predicted by elemental analysis (Table 1).

The situation is more complicated for compound (2) because the thermogram shows several changes in the slope during the thermal decay of compound (2), evident in FIG. 19B. These slope changes indicate inequivalent stability of chemical species within the lattice structure, as well as complexity in the MOF structure of compound (2). The first step in the thermogram in FIG. 19C belongs to four bpe and three oxalate ligands. The second step represents various decomposition steps for Pb. The residue in FIG. 19B is three $PbO_2$ in compound (2).

The TGA for compound (3) shown in FIG. 19C hides even more information since some MOF structures with 3D pores show integration of all chemical species decomposition on one large step. However, the 1% loss of water can be seen at low temperature, which matches reported TGAs for analogous Zn(II) MOF.

Thermogravimetric analysis (TGA) experiments were conducted to investigate the behavior of water molecules during grinding and its impact on the photoreactivity in compound (4). A total of six TGA experiments were conducted on three compound (4) samples, each before and after UV irradiation. The three samples of compound (4) are single crystals, 10-minute ground, and 20-minute ground samples. FIG. 20A to 20F show the TGA thermograms obtained for each sample before and after UV irradiation. Table 4 shows a summary of the percent (%) weight loss of water molecules obtained from TGA thermograms shown in FIG. 20A to 20F for compound (4).

TABLE 4

Percent (%) Weight loss of $H_2O$ molecules in Compound (4) from TGA

| Compound 4* | % Wt. Loss |
| --- | --- |
| Single Crystals | 4.48 |
| Single Crystals (UV Irradiated) | 4.18 |
| 10 min. Grinded Crystals | 5.83 |
| 10 min. Grinded Crystals (UV Irradiated) | 7.35 |
| 20 min. Grinded Crystals | 3.11 |
| 20 min. Grinded Crystals (UV Irradiated) | 6.23 |

*Expected weight loss for one water molecule is 3.41%

Figure 21:
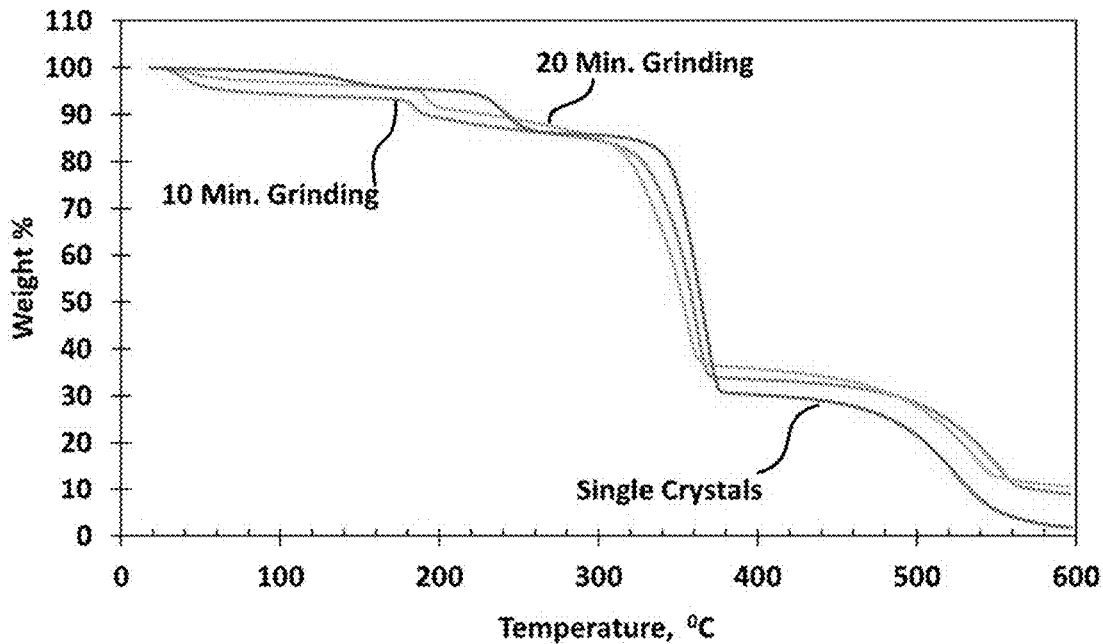
FIG. 21 shows a compilation of TGA thermograms of single crystal, 10-minute ground, and 20-minute ground samples of compound (4) before UV irradiation.
Figure 22:
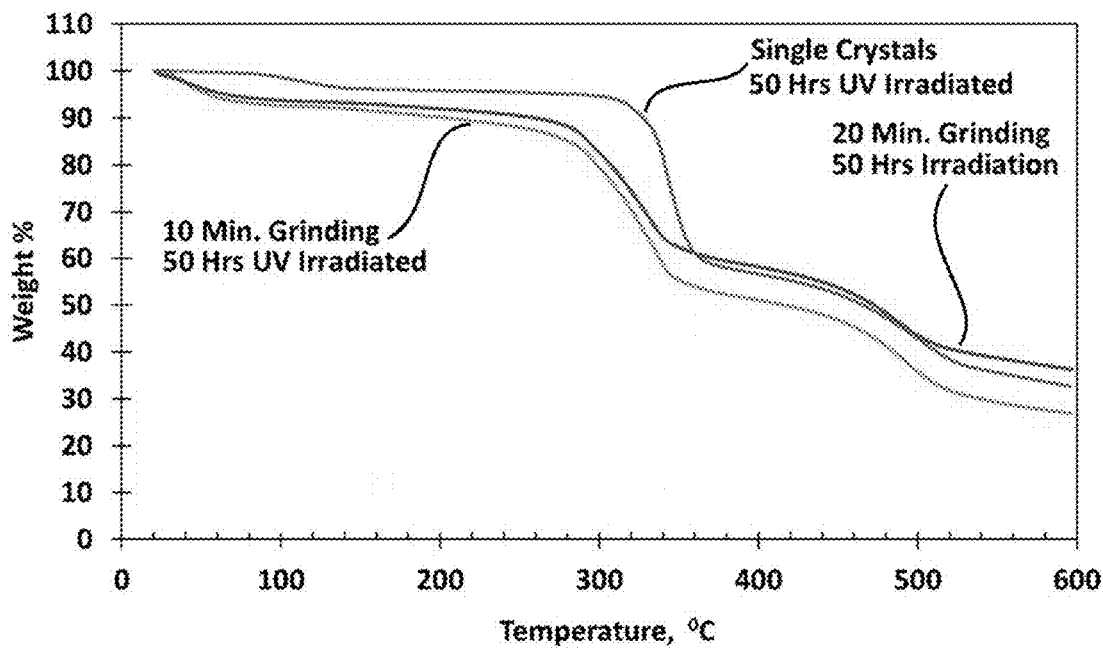
FIG. 22 shows a compilation of TGA thermograms of single crystal, 10-minute ground, and 20-minute ground samples of compound (4) after 50 hours of UV irradiation.

Although the expected weight loss for one water molecule in 4 is 3.41%, Table 4 shows 25% higher values in single crystals than the theoretically calculated values. This divergence may be due to the absorption of water molecules from the air. Ground crystals show even higher values, which may be due to their higher surface area. UV-irradiated samples have higher values of water % weight loss due to long exposure to the atmosphere while irradiating for 50 hours in a photoreactor. FIGS. 21 and 22 show compiled TGA thermograms obtained before and after UV irradiation for the three samples of compound (4).

The thermogravimetric analysis data compiled in FIGS. 21 and 22 show that little difference between 10 and 20 minutes of grinding for compound (4) samples as their TGA curves are almost identical. The ground samples also show that the temperature of water molecule loss does not change significantly between pre- and post-irradiation samples. However, the loss of water molecules in single crystals is above 110° C., while the water loss is near 50° C. for ground crystal samples.

The change in water loss temperature between single and ground crystals indicates these water molecules are coordinated in single crystals, while the water molecules are uncoordinated, i.e., free water molecules, within the lattice structure of ground crystal samples. These observations indicate that grinding may cause coordinated water molecules to break free from the coordination sphere. The change in water molecule bonding and arrangement within the lattice structure may have caused photoreactivity to increase. The grinding or other mechanical approaches may enhance the reactivity of inventive materials due to increases surface area and/or formation of crystal defects.

FT-IR Spectroscopy of Compounds (1) to (4)

Shifts in FT-IR peaks, as well as their appearance or disappearance can be interpreted in terms of coordination of the ligands to the metal ions. FT-IR spectra compounds (1) to (4) were taken to investigate the coordination of organic linkers through its carboxylic acid peaks, as well as other characteristic bands. FIG. 23A to 23H show the FT-IR spectra of compounds (1) to (4) before and after UV irradiation.

The disappearance of the carboxylic acid O—H stretching frequencies of oxalic or fumaric acid, a broad and strong peak from 2500 to 3300 $cm^{-1}$ in FIGS. 23A, 23C, 23E, and 23G, in the FT-IR spectra of the samples of compounds (1) to (4) prior to UV irradiation is believed to be a result of deprotonation of carboxylic acid functional groups, leading to coordination of the oxygen atoms to the metal ion in the respective MOFs.

Although a Zn—N stretching vibration can be observed below 500 $cm^{-1}$, Zn—O stretching also can be observed in the same region. The precise location of the Zn-based signals can vary depending on the electronic environment as well as the morphology of the compound. Two signals can be observed at 494.6 and 546.0 $cm^{-1}$ in the spectrum of compound (1) before UV irradiation (FIG. 23A), and these bands were assigned to O—Zn—O symmetrical and asymmetrical stretching vibrations. No Pb—O and Pb—N stretching bands can be seen in FIGS. 23C and 23F for compounds (2) and (3), as Pb—O and Pb—N stretching frequencies are respectively 272 and 213 $cm^{-1}$, i.e., beyond the detection range. Although compounds (1) to (3) have not been reported previously, the FT-IR spectrum of compound (4) in FIG. 23 matches reported results.

The photochemical [2+2] cycloaddition reaction forms cyclobutane derivative, which lead to the disappearance of alkene C—H stretching, slightly after 3000 $cm^{-1}$, in the FT-FR spectra taken of the samples of compounds (1) to (4) after UV irradiation. However, the alkene C—H stretching cannot be observed clearly due to interference of the aromatic C—H stretching bands with the hydrogens of the bpe rings. Moreover, the alkane C—H stretching, slightly before 3000 $cm^{-1}$, due to the photochemical [2+2] cycloaddition is barely visible, but can be seen for the FT-IR spectra of compounds (1), (2), and (4) in FIG. 23A to 23D, 23G, and 23H. Distinguishing alkene C=C stretching in IR for compounds (1) to (4) is also impractical due to the aromatic C=C stretching in the same region.

The broad peak observed around 3500 $cm^{-1}$ in the IR spectra (FIG. 23B to 23G) can be attributed to the presence of water molecules within the lattice structure of compounds 1-4, as well as absorption of moisture from the air. However, the presence of hydrogen bonding might also contribute to the appearance of this broad peak.

CHN analysis indicated that compound (1) may contain DMF solvent molecules in its lattice. This hypothesis is supported by the presence of characteristic DMF signals in the FT-IR spectrum of compound (1) in FIGS. 23A and 23B. The main functional groups of DMF identifiable by FT-IR are the $sp^3$ C—H stretching vibrations from methyl groups, and carbonyl and C—N stretching bands. Although $sp^3$ C—H stretching bands near 3000 $cm^{-1}$ can be seen in FIGS. 23A and 23B, they are relatively weak. However, the carbonyl band is strong and can be seen clearly at 1625 $cm^{-1}$ in FIG. 23A. The C—N stretching band of amide generally appears near 1400 $cm^{-1}$, and may be assigned to the medium-intensity peak at 1382.1 $cm^{-1}$ in FIG. 23A.

Figure 23A:
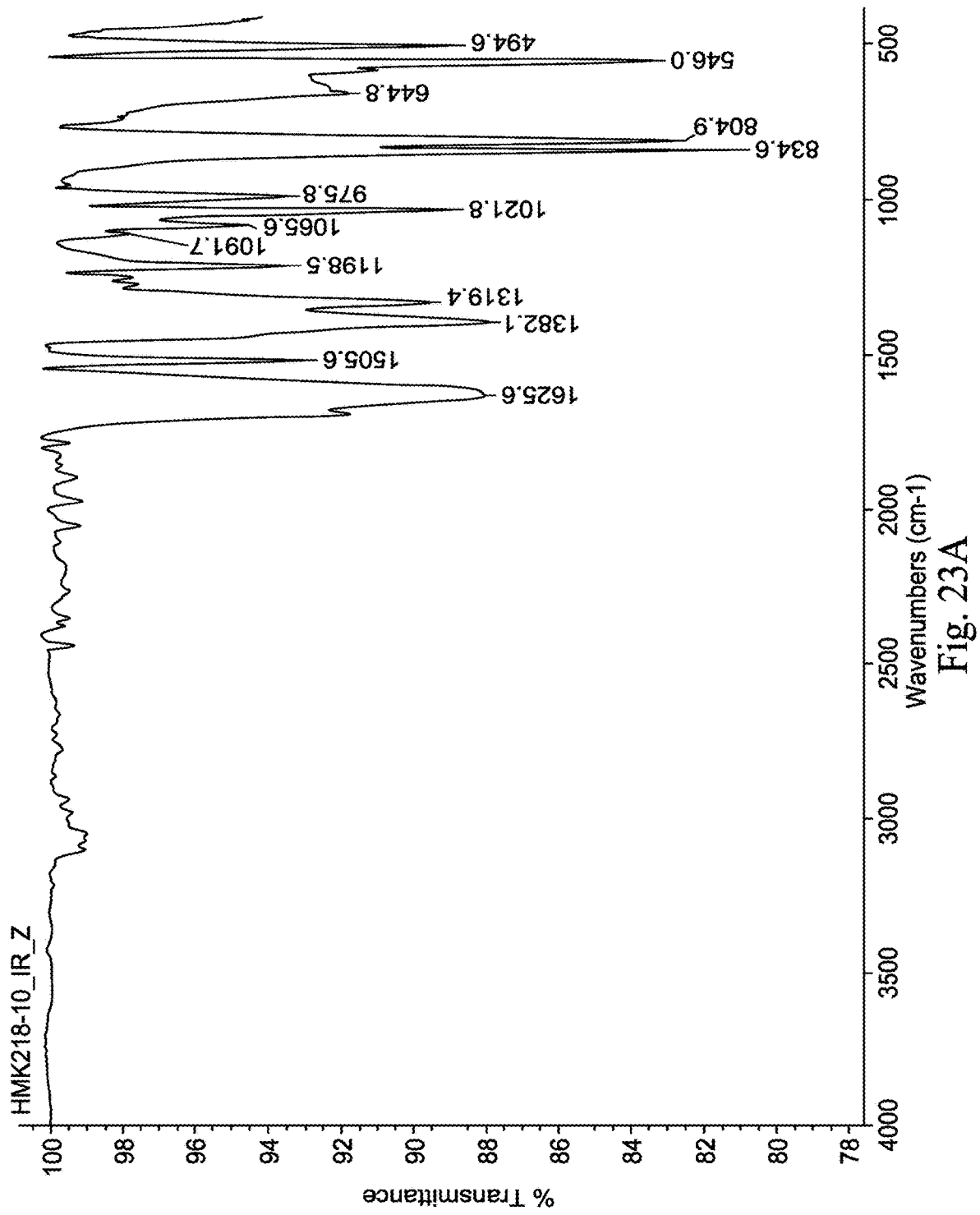
FIG. 23A shows a Fourier-transform infrared (FT-IR) spectrum of compound (1) before UV irradiation.
Figure 23B:
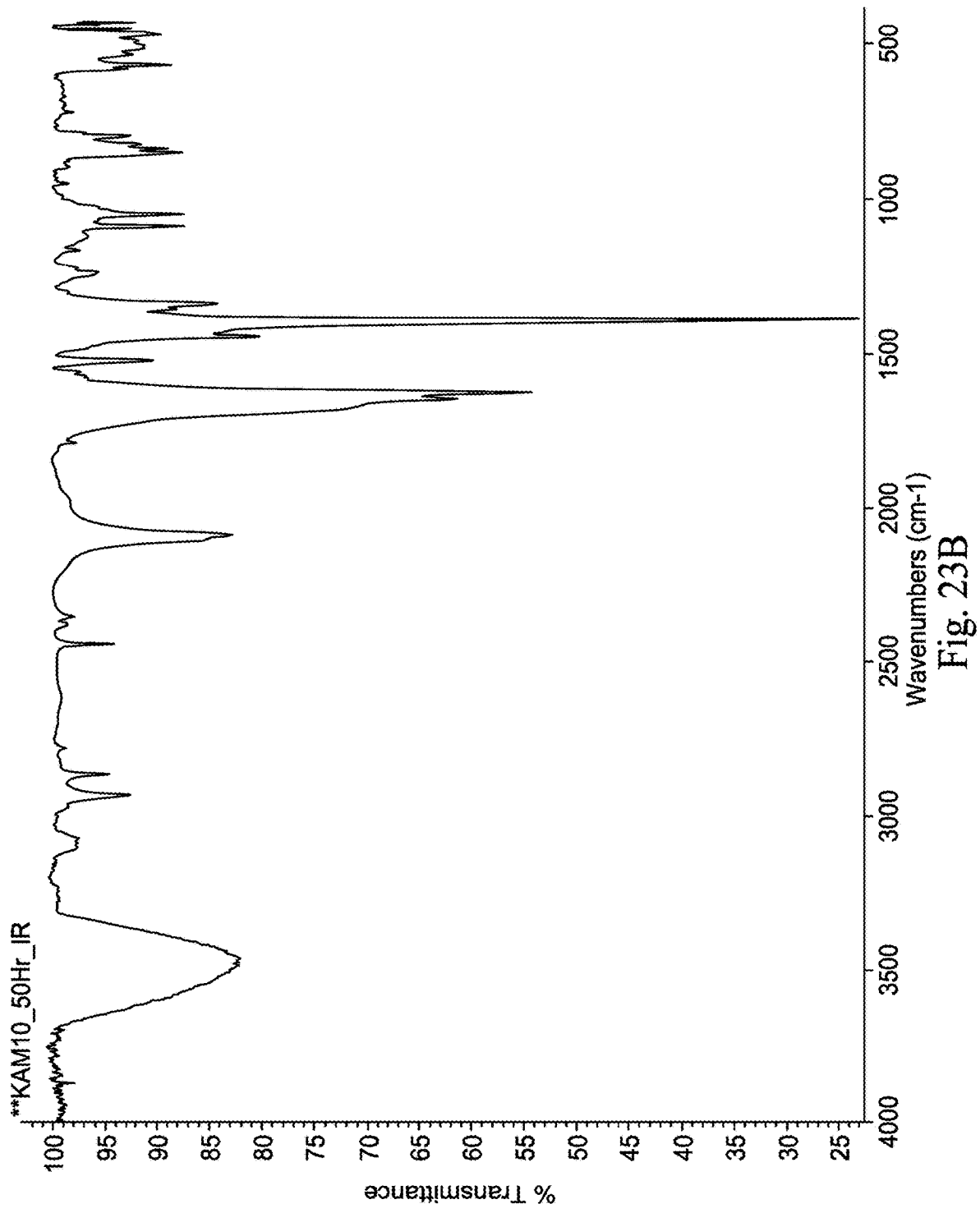
FIG. 23B shows an FT-IR spectrum of compound (1) after 50 hours of UV irradiation.
Figure 23C:
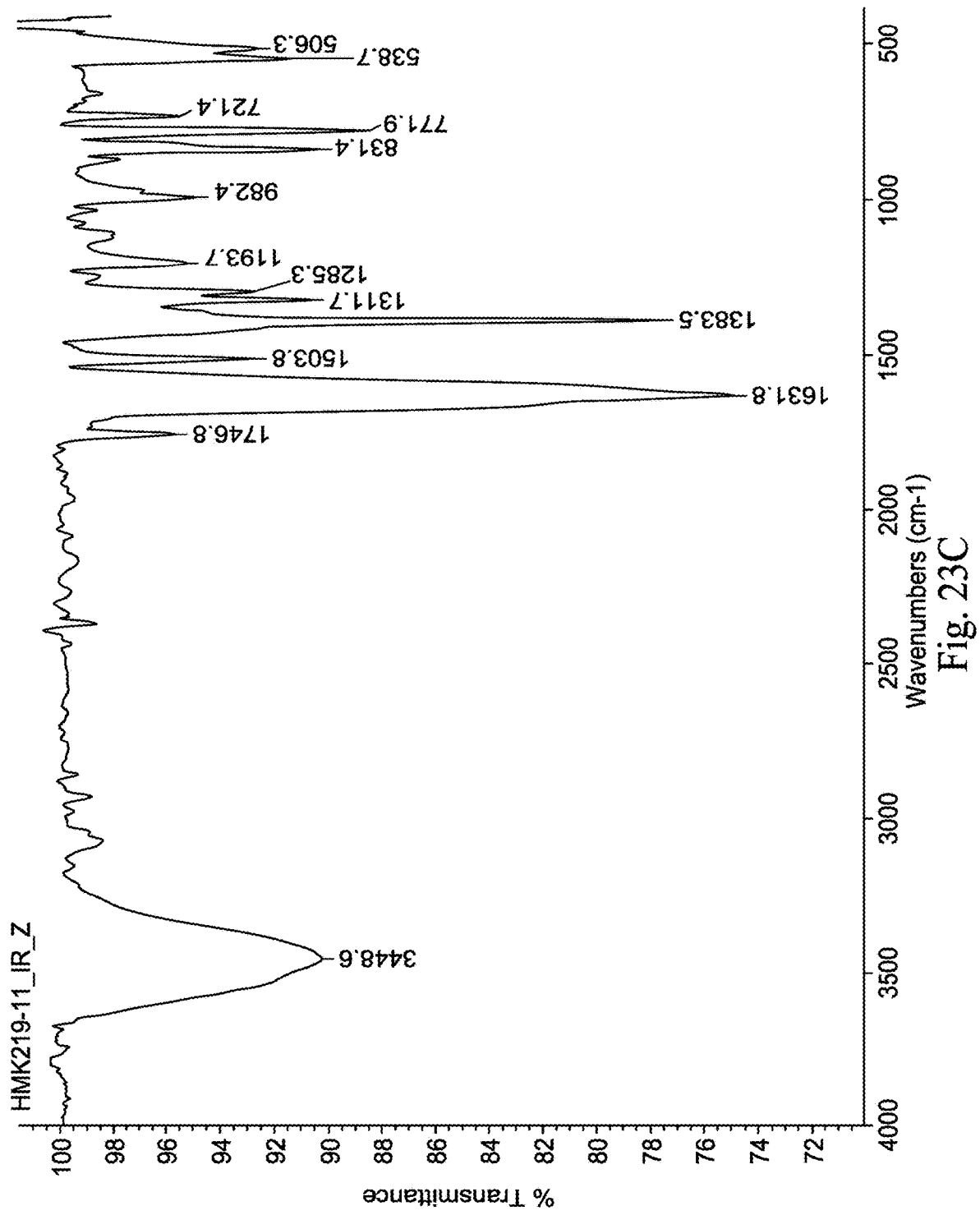
FIG. 23C shows an FT-IR spectrum of compound (2) before UV irradiation.
Figure 23D:
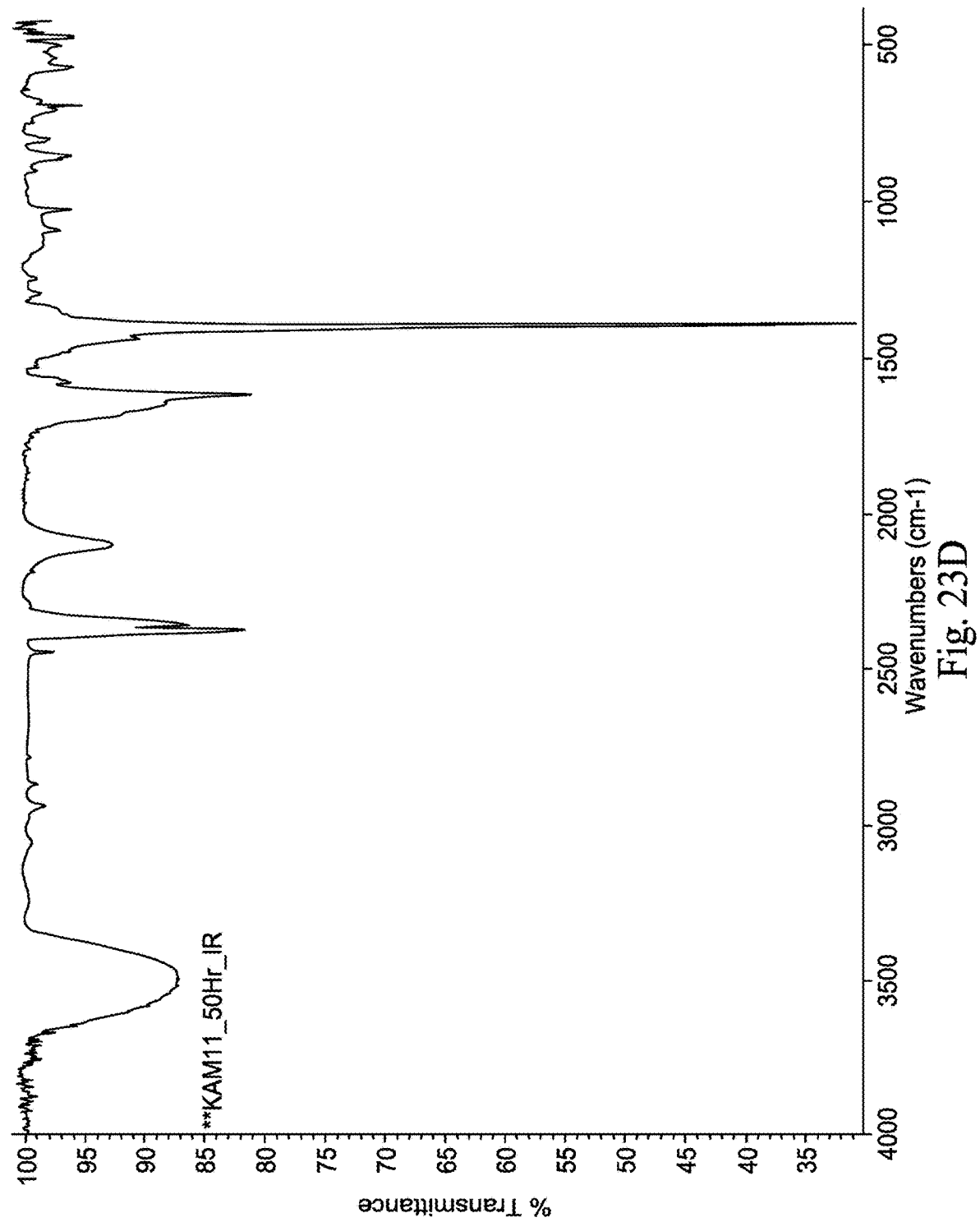
FIG. 23D shows an FT-IR spectrum of compound (2) after 50 hours of UV irradiation.
Figure 23E:
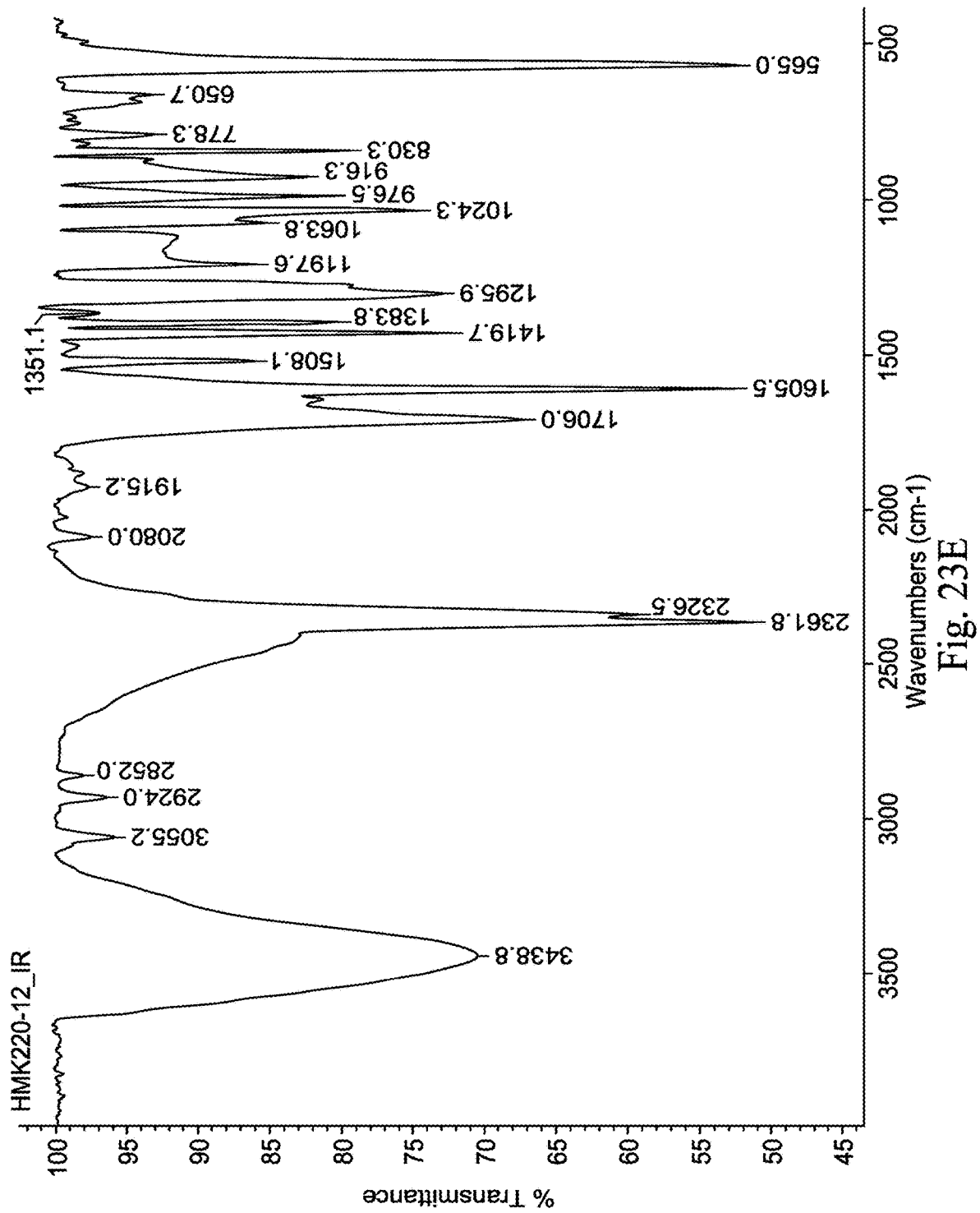
FIG. 23E shows an FT-IR spectrum of compound (3) before UV irradiation.
Figure 23F:
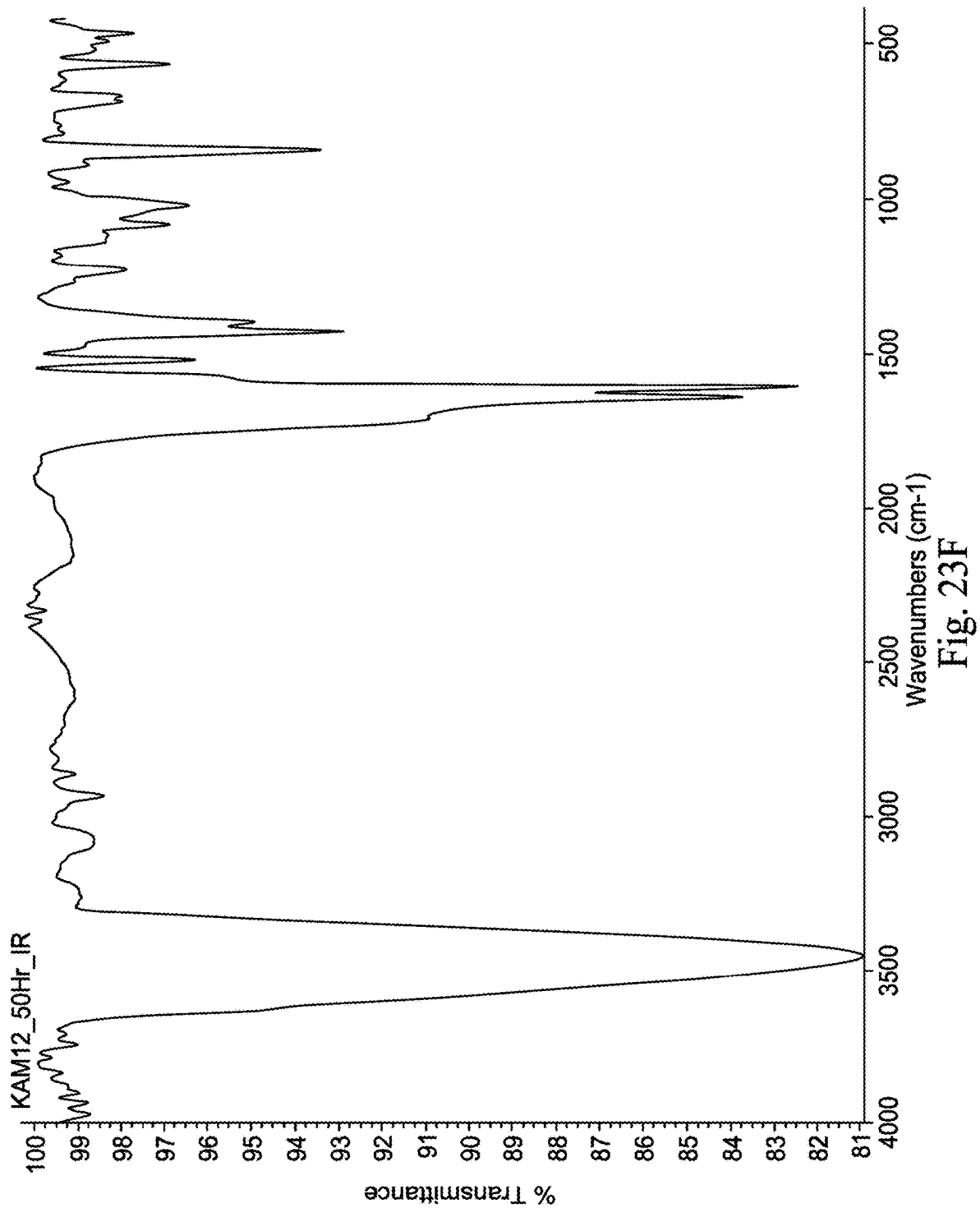
FIG. 23F shows an FT-IR spectrum of compound (3) after 50 hours of UV irradiation.
Figure 23G:
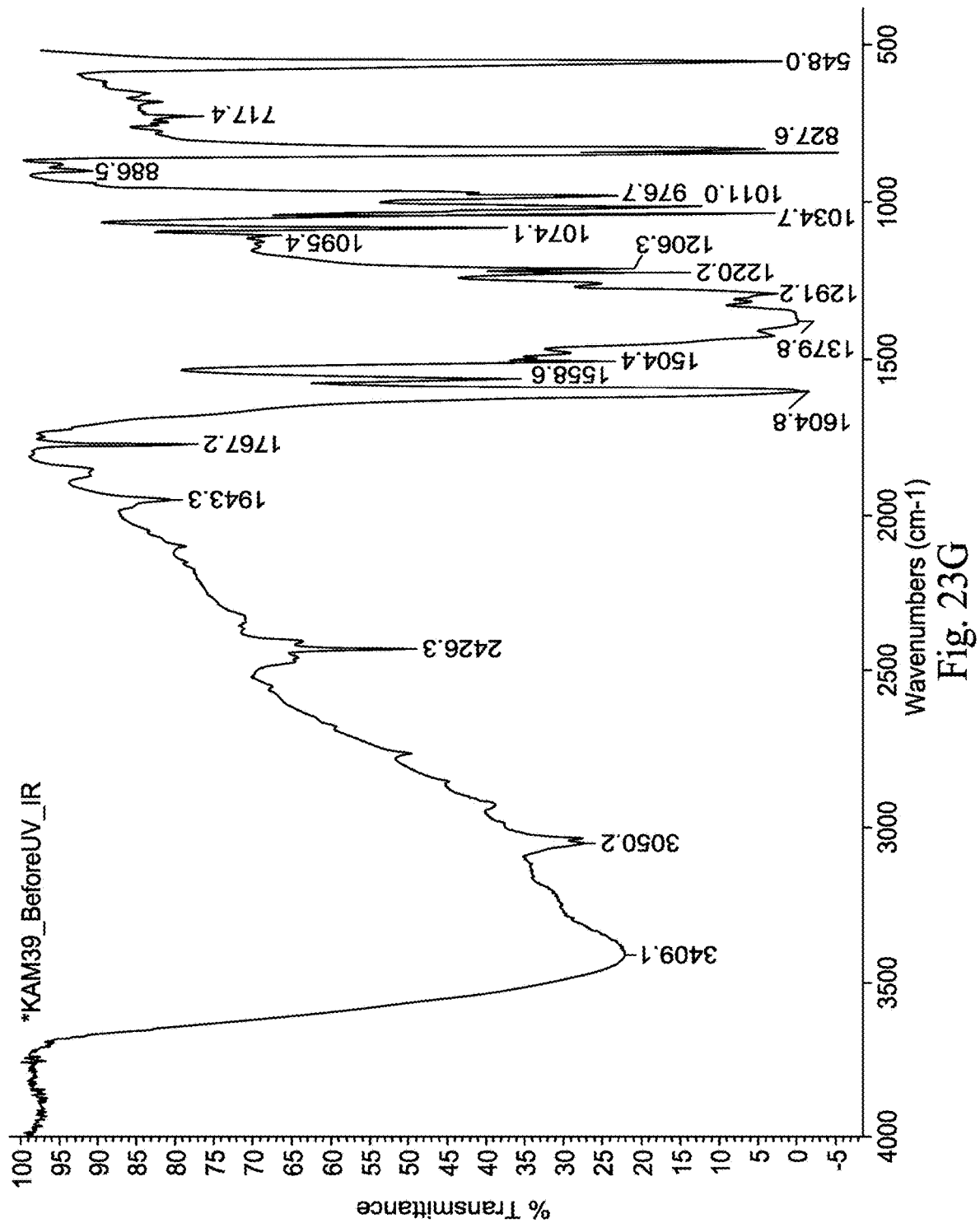
FIG. 23G shows an FT-IR spectrum of compound (4) before UV irradiation.
Figure 23H:
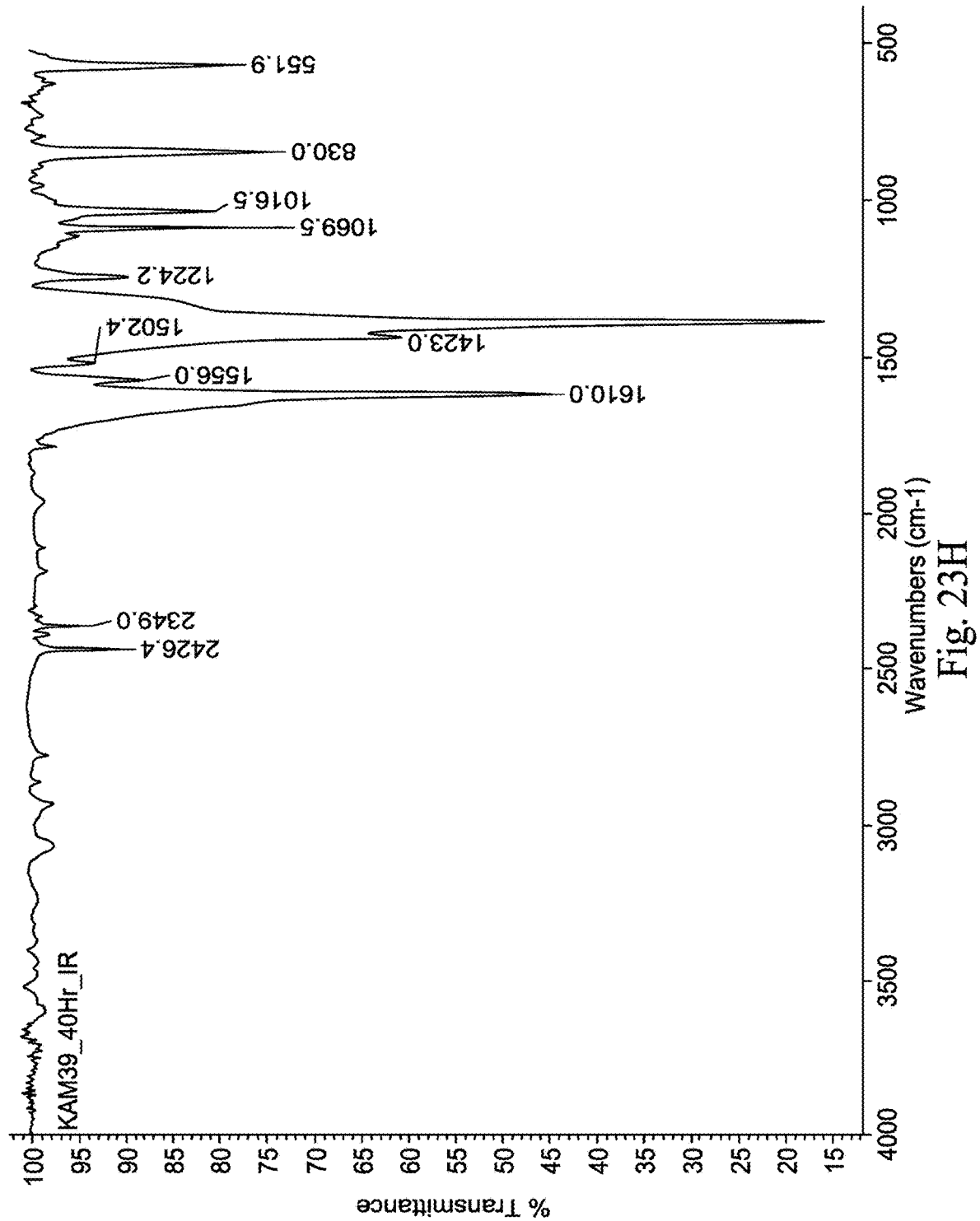
FIG. 23H shows an FT-IR spectrum of compound (4) after 40 hours of UV. irradiation.

The presence of $NO_3^-$ anion in compounds (2) and (4) can identified by FT-IR with two characteristic peaks range between 800 to 860 and 1340 to 1410 $cm^{-1}$. In FIG. 23C, characteristic signals can be seen at 831.4 and 1383.5 $cm^{-1}$ for compound (2), which is consistent with the proposed formula in the CHN elemental analysis. However, the signals at 831.4 and 1383.5 $cm^{-1}$ are less apparent after UV irradiation, as indicated in FIG. 23D. These two peaks also can be identified for compound (4) before and after UV irradiation FIGS. 23G and 23H at around 830 and 1380 $cm^{-1}$, indicating successful synthesis of target compound.

Based on comparable powder XRD patterns, the proposed structure of compound (1) was believed have free misaligned bpe ligands capable of undergoing internal molecular motion to overcome misalignment by mechanism including three steps: sliding; isomerization; and bond formation. Compound (2) and (3) were hypothesized to be 3D frameworks of 2D sheets with different topologies pillared by bpe ligands.

The photoreactivity of these compounds can be monitored by $^1$H-NMR spectroscopy for successful photochemical [2+2] cycloaddition. About 90%, i.e., ±1, 2.5, 5, or 7.5%, conversions of bpe ligands within compounds (1) and (2) have photochemically reacted to yield rctt-tpcb within 50 hours of UV irradiation for compound (1) and 15 hours for compound (2), while 100% conversion can be achieved after only 5 hours of UV irradiation for compound (3). Inventive materials, such as compound (2), can undergo reversible photochemical [2+2] cycloaddition, which may make them suitable for photo-switching, sensing, and optical data recording.

MOFs of analogous structures to compound (4) may be inventively boosted in photoreactivity by initiation of internal molecular movement via grinding. The amount of increase in photoreactivity, based on photochemical [2+2] cycloadditions converting bpe to ret-tpcb, may be increased, for example by at least 10, 15, 20, 25, 35, 45, 50%, or more, and/or up to 100, 90, 80, 75, 65, 60, or 55%, by such grinding, e.g., upon at least 10, 15, 20, 25, 35, 45, or 50 hours and/or up to 100, 90, 80, 70, 60, 55, or 50 hours of UV irradiation of ground crystals.

Numerous modifications and variations of the present invention are possible in light of the above teachings. It is therefore to be understood that within the scope of the appended claims, the invention may be practiced otherwise than as specifically described herein.

The invention claimed is:

1. A method of increasing the conversion of a [2+2] cycloaddition, the method comprising:
    grinding a metal organic framework (MOF) to obtain a ground MOF, the MOF optionally being a hydrate and/or nitrate; and
    irradiating an olefinic substrate in the presence of the ground MOF with UV light,
    wherein the MOF has repeating structural units, each structural unit comprising:
        Zn(II), Pb(II), and/or Cd(II) as a metal ion;
        a 4,4'-bipyridylethylene(bpe) ligand as a first ligand; and
        fumaric acid (fum) and/or oxalic acid (ox) as a second ligand,
    wherein the 4,4'-bipyridylethylene ligands are stacked in the MOF, and
    wherein a distance between two consecutive 4,4'-bipyridylethylene ligands is less than 5 Angstroms, and
    wherein the first ligand is protonated.

2. The method of claim 1, wherein the metal ion of the MOF comprises the Pb(II) in each MOF unit.

3. The method of claim 1, wherein the metal ion of the MOF comprises a first and a second of the Zn(II) per MOF unit.

4. The method of claim 1, wherein the MOF comprises a first, second, and third of the oxalic acid as the second ligand per MOF unit.

5. The method of claim 1, wherein the metal ion of the MOF comprises a first, second, third, and fourth of the Pb(II) per MOF unit.

6. The method of claim 1, wherein the structural unit of the MOF has a formula:

[Pb$_4$(ox)$_3$(bpe)$_4$(H$_2$O)$_4$].

7. The method of claim 1, wherein the structural unit of the MOF has a formula:

[Pb$_4$(ox)$_3$(bpe)$_4$(H$_2$O)$_4$].(NO$_3$)$_2$.

8. The method of claim 1, wherein the structural unit of the MOF has a formula:

[Pb(bpe)(fum)].

9. The method of claim 1, wherein the structural unit of the MOF has a formula:

[Pb(bpe)(fum)].0.25(H$_2$O).

10. The method of claim 1, wherein the irradiating causes the olefinic substance to undergo a [2+2] cycloaddition reaction and form a compound with a cyclobutane moiety.

11. The method of claim 1, wherein the olefinic substance consists of a single olefinic compound and the [2+2] cycloaddition reaction is a photodimerization of the single olefinic compound.

12. The method of claim 1, wherein the [2+2] cycloaddition reaction proceeds stereospecifically to form a product that is at least 75% of a single isomer.

* * * * *